(12) United States Patent
Albertsen et al.

(10) Patent No.: US 12,146,148 B2
(45) Date of Patent: Nov. 19, 2024

(54) FERTILITY RESTORATION IN PLANTS

(71) Applicant: PIONEER HI-BRED INTERNATIONAL, INC., Johnston, IA (US)

(72) Inventors: Marc C Albertsen, Grimes, IA (US); Tim Fox, Des Moines, IA (US); Manjit Singh, Johnston, IA (US); Mark E Williams, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 17/275,111

(22) PCT Filed: Sep. 13, 2019

(86) PCT No.: PCT/US2019/051019
§ 371 (c)(1),
(2) Date: Mar. 10, 2021

(87) PCT Pub. No.: WO2020/056259
PCT Pub. Date: Mar. 19, 2020

(65) Prior Publication Data
US 2022/0056472 A1    Feb. 24, 2022

Related U.S. Application Data

(60) Provisional application No. 62/832,716, filed on Apr. 11, 2019, provisional application No. 62/815,261, filed on Mar. 7, 2019, provisional application No. 62/731,252, filed on Sep. 14, 2018.

(51) Int. Cl.
*C12N 15/82*    (2006.01)

(52) U.S. Cl.
CPC ..... *C12N 15/8289* (2013.01); *C12N 15/8213* (2013.01)

(58) Field of Classification Search
None
See application file for complete search history.

(56) References Cited

U.S. PATENT DOCUMENTS

| | | | |
|---|---|---|---|
| 7,154,024 | B2 | 12/2006 | Albertsen et al. |
| 10,028,460 | B2 | 7/2018 | Weissmann et al. |
| 2018/0010145 | A1 | 1/2018 | Cigan |
| 2018/0100145 | A1 | 4/2018 | Lau et al. |
| 2018/0201946 | A1 | 7/2018 | Cigan et al. |

FOREIGN PATENT DOCUMENTS

| WO | WO-9851142 | A1 | 11/1998 |
|---|---|---|---|
| WO | WO-2005059121 | A2 | 6/2005 |
| WO | WO-2012047595 | A2 | 4/2012 |
| WO | WO-2014039815 | A2 | 3/2014 |
| WO | WO-2014164961 | A2 | 10/2014 |
| WO | WO-2015135940 | A1 | 9/2015 |
| WO | WO-2019043082 | A1 | 3/2019 |

OTHER PUBLICATIONS

Cigan, Phenotypic complementation of ms45 maize requires tapetal expression of MS45, Sexual Plant Reproduction, (2001) 14:135-142 (Year: 2001).*
Hossain, Fertility Compensation of Cornerstone Male Sterility of Wheat by Rye, Genetics Society of America, 1983 (Year: 1983).*
Zeven, Wheats with Purple and blue grains: a review, Euphytica, 1991 (Year: 1991).*
Whitford, Ryan, et al. "Hybrid breeding in wheat: technologies to improve hybrid wheat seed production." Journal of experimental botany 64.18 (2013): 5411-5428. (Year: 2013).*
Teare, M. Dawn, and Jennifer H. Barrett. "Genetic linkage studies." The Lancet 366.9490 (2005): 1036-1044. (Year: 2005).*
Poczai, Péter, et al. "Advances in plant gene-targeted and functional markers: a review." Plant methods 9 (2013): 1-32. (Year: 2013).*
Singh, Sudhir P., Rakesh Srivastava, and Jitendra Kumar. "Male sterility systems in wheat and opportunities for hybrid wheat development." Acta Physiologiae Plantarum 37 (2015): 1-13. (Year: 2015).*
Sunil, L., and Nandini P. Shetty. "Biosynthesis and regulation of anthocyanin pathway genes." Applied Microbiology and Biotechnology 106.5-6 (2022): 1783-1798. (Year: 2022).*
Whitford, Hybrid breeding in wheat: technologies to improve hybrid wheat seed production, Journal of Experimental Botany, col. 64, No. 18, pp. 5411-5428, 2013 (Year: 2013).*
Li, N.; et al.: "ThMYC4E, candidate Blue Aleurone 1 gene controlling the associated trait in *Triticum aestivum*," PLOS One, Jul. 13, 2017 (Jul. 13, 2017), vol. 12, No. 7, pp. 1-13.
Tucker, E.J.; et al.: "Molecular identification of the wheat male fertility gene Ms1 and its prospects for hybrid breeding," Nature, Oct. 11, 2017 (Oct. 11, 2017), vol. 8, No. 869, p. 6.

(Continued)

*Primary Examiner* — Weihua Fan
*Assistant Examiner* — Brian James Sullivan

(57) ABSTRACT

Provided herein are methods and compositions for restoring fertility and maintaining sterility in plants. In particular, one method disclosed includes introducing into a male-sterile plant, wherein the plant comprises one or more homozygous mutations in a male-fertility gene, a plant restoration donor chromosomal component comprising a plant-derived polynucleotide that confers a plant phenotypic marker linked to a male-fertility restoration locus that functionally complements the male-sterility phenotype from the one or more homozygous mutations in the male-sterile plant. In some examples, the plant-derived polynucleotide that confers a plant phenotypic marker and the male-fertility restoration locus are linked to each other and located on the same chromosomal arm on the plant restoration donor chromosomal component. In some examples, the plant-derived polynucleotide that confers a plant phenotypic marker, the male-fertility restoration locus, or both are modified.

9 Claims, 4 Drawing Sheets
Specification includes a Sequence Listing.

(56) References Cited

OTHER PUBLICATIONS

Wu, Y.; et al.: "Development of a novel recessive genetic male sterility system for hybrid seed production in maize and other cross-pollinating crops," Plant Biotechnology Journal, Mar. 2016 (Mar. 2016), vol. 14, No. 3, pp. 1046-1054.
International Search Report and Written Opinion for International Application No. PCT/US19/51019, Mailed Jan. 22, 2020.
Petition for Nonregulated Status No. DP-32138 (Jan. 2011). United States Department of Agriculture (USDA) Animal and Plant Health Inspection Service (APHIS).
Extended European Search Report for European Application No. 19858811.3, mailed Apr. 22, 2022, 07 Pages.
International Preliminary Report on Patentability for International Application No. PCT/US2019/051019, mailed Mar. 25, 2021, 17 Pages.
Zhou K., et al., "The 4E-ms System of Producing Hybrid Wheat," Crop Science, Jan. 24, 2006, vol. 46, No. 1, pp. 250-255.

* cited by examiner

SEQUENCE LISTING

<160> NUMBER OF SEQ ID NOS: 42

<210> SEQ ID NO 1
<211> LENGTH: 1857
<212> TYPE: DNA
<213> ORGANISM: triticum aestivum

<400> SEQUENCE: 1

```
atggagagat cccgccgcct gctgctggtg gcgggcctgc tcgccgcgct gctcccggcg      60
gcggcggccg ccttcgggca gcagccgggg gcgccgtgcg agcccacgct gctggcgacg     120
caggtggcgc tcttctgcgc gcccgacatg cccaccgcgc agtgctgcga gcccgtcgtc     180 gccgcgtcg acctcggcgg cggggtcccc tgcctctgcc gcgtcgccgc ggagccgcag     240
ctcgtcatgg cgggcctcaa cgccacccac ctcctcacgc tctacagctc ctgcggcggc     300
ctccgtcccg gcggcgccca cctcgccgcc gcctgcgaag gtacgcgcac gttcaccgcc     360
ctccgtccct ccctctctct gtctacgtgc agattttctg tgctctcttt cctgcttgcc     420
tagtacgtag tgttccatgg cctctcgggc cgctagcgct ccgatttgcg ttggtttcct     480
tgctgttctg ccggatctgt tggcacggcg cgcggcgtcg ggttctcgcc gtctcccgtg     540
gcgagcgacc tgcgcagcgc gcgcggcctg gctagcttca taccgctgta ccttgagata     600
cacggagcga tttagggtct actctgagta tttcgtcatc gtaggatgca tgtgccgctc     660
gcgattgttt catcgatttg agatctgtgc ttgttcccgc gagttaagat ggatctagcg     720
ccgtacgcag atgcagagtc tgttgctcga gttaccttat ctaccgtcgt tcgactatgg     780
tatttgcctg cttcctttg gctgggttta tcgtgcagta gtagtagaca tgtggacgcg     840
ttcttcttat tttgtgccga ccatcgtcga gatactttc ctgctacagc gtttcatcgc     900
ctgcaccatc ccgttcgtga tagcactttt gtgtcaaacc gcaacgcagc tttgctttct     960
gcggtatctt ctgccttgtt tgtcgccttg cttggtcaaa actgagaact cttgctgttt    1020
gatcgaccga gggcagaggc agagcaagag cctgccgtgc ttttggctct gcagtgcgtc    1080
gtctctgcct cctttgccaa acatttccat gttgatcctc tgggggcact gcttttttcgc    1140 atgcggtttc cgtagccttc ctctttcatg aaaaaaggtt tgggtcaaat caaatggatc    1200
gcctattggc agagcagcag cagatagctg gctgtctcac agctttggca gaatcggtct    1260
gttgcctgcc accgtgtctc ttatcttgcc tgccaccgtg tctctttct tgttgcgcac    1320 gtcgtcacct cctcctactt cttttccagt tttgtttact tttgatgaaa tacggacgaa    1380
```

-continued

```
cggctggtaa tcattaactt tggttgctgt tgttactgtg gattttggac gcaggacccg    1440 ctccccggc cgccgtcgtc agcagccccc cgccccgcc accgtcgacc gcacctcgcc      1500
gcaagcagcc agcgcgtgcg tacctctccc tctcgcccgc atctcgctcc gtattaactg    1560
attgtgtctg catactgacg tgtgctttgg ctttggatct gtttcgcaga cgacgcacca    1620
ccgccgccgc cgccgtccag cgacaagccg tcgtccccgc cgccgtccca ggaacacgac    1680
ggcgccgctc cccacgccaa ggcgccccc gcccaggcgg ctacctcccc gctcgcgccc     1740
gctgctgcca tcgccccgcc gccccaggcg ccacactccg ccgcgcccac ggcgtcatcc    1800
aaggcggcct tcttcttcgt cgccacggcc atgctcggcc tctacatcat cctctga      1857
```

<210> SEQ ID NO 2
<211> LENGTH: 222
<212> TYPE: PRT
<213> ORGANISM: triticum aestivum

<400> SEQUENCE: 2

```
Met Glu Arg Ser Arg Arg Leu Leu Leu Val Ala Gly Leu Leu Ala Ala
1               5                   10                  15

Leu Leu Pro Ala Ala Ala Ala Ala Phe Gly Gln Gln Pro Gly Ala Pro
                20                  25                  30

Cys Glu Pro Thr Leu Leu Ala Thr Gln Val Ala Leu Phe Cys Ala Pro
            35                  40                  45

Asp Met Pro Thr Ala Gln Cys Cys Glu Pro Val Val Ala Ala Val Asp
        50                  55                  60

Leu Gly Gly Val Pro Cys Leu Cys Arg Val Ala Ala Glu Pro Gln
65                  70                  75                  80

Leu Val Met Ala Gly Leu Asn Ala Thr His Leu Leu Thr Leu Tyr Ser
                85                  90                  95

Ser Cys Gly Gly Leu Arg Pro Gly Gly Ala His Leu Ala Ala Ala Cys
                100                 105                 110

Glu Gly Pro Ala Pro Pro Ala Ala Val Val Ser Pro Pro Pro Pro
            115                 120                 125

Pro Pro Ser Thr Ala Pro Arg Arg Lys Gln Pro Ala His Asp Ala Pro
        130                 135                 140

Pro Pro Pro Pro Ser Ser Asp Lys Pro Ser Ser Pro Pro Ser
145                 150                 155                 160

Gln Glu His Asp Gly Ala Ala Pro His Ala Lys Ala Ala Pro Ala Gln
                165                 170                 175

Ala Ala Thr Ser Pro Leu Ala Pro Ala Ala Ala Ile Ala Pro Pro
            180                 185                 190

Gln Ala Pro His Ser Ala Ala Pro Thr Ala Ser Ser Lys Ala Ala Phe
        195                 200                 205

Phe Phe Val Ala Thr Ala Met Leu Gly Leu Tyr Ile Ile Leu
    210                 215                 220
```

<210> SEQ ID NO 3
<211> LENGTH: 1856
<212> TYPE: DNA
<213> ORGANISM: triticum aestivum

<400> SEQUENCE: 3

```
atggagagat cccgcgggct gctgctggtg gcggggctgc tggcggcgct gctgccggcg    60
gcggcggcgc agccgggggc gccgtgcgag ccgcgctgc tggcgacgca ggtggcgctc    120
ttctgcgcgc ccgacatgcc gacggcccag tgctgcgagc ccgtcgtcgc cgccgtcgac    180
```

-continued

```
ctcggcggcg gggtgccctg cctctgccgc gtcgccgccg agccgcagct cgtcatggcg    240
ggcctcaacg ccaccacct cctcacgctc tacagctcct gcggcggcct ccgcccggc     300 ggcgcccacc tcgccgccgc ctgcgaaggt acgttgtccg cctcctcccc tccctccctc    360
cctccctctc tctctacgtg ctcgctttcc tgcttaccta gtagtacgta gtttcccatg    420
ccttcttgac tcgctagaag tgctccggtt tgggtctgtt aatttcctcg ctgtactacc    480
ggatctgtcg tcggcacggc gcgcggcgtc gggtcctcgc cttctcccgt ggcgaccgac    540
ctgcgcagcg cgcgcgcggc ctagctagct tcataccgct gtacctcgac atacacggag    600
cgatctatgg tctactctga gtatttcctc atcgtagaac gcatgcgccg ctcgcgattg    660
tttcgtcgat tctagatccg tgcttgttcc cgcgagttag tatgcatctg cgtgcatatg    720
ccgtacgcac gcagatgcag agtctgttgc tcgagttatc tactgtcgtt cgctcgacca    780
tatttgcctg ttaatttcct gttcatcgtg catgcagtag tagtagccat gtccacgcct    840
tcttgttttg aggcgatcat cgtcgagatc catggctttg cttctgcac tatcttctgc     900 cttgttttgt tctccgcagt acgtacgtct tgcttggtca aaactgaaaa acgctttgct    960
gtttgtttga tcggcaagag ctggccgtgc ttttggcacc gcagtgcgtc gcctctgccg   1020
cttttgcgaa acatttccat gttgatcctc tggcggaact acttttttcgc gtgcggtttg   1080 cgtggccttc ctctctcgtg aaaagaggtc gggtcaaacc aaatggatcg cctcttggca   1140
gagcagcggc agcagatagc tggccgtctc gcagctttgg cagaaccggt ctgtggccat   1200
ctgtcgccgc ctgccaccgt ttccctgatg tttgtttctc tctcgcctgc cactgtttct   1260
tttcttgttg cgcacgtacg tcgtcacctc ctcctacttt tttgccagtt tgtttactt    1320 ttgatgaaat atacggatga atcggctggt gattaacttt ggctgctgct gttaattact   1380
gtggattttg gatgcaggac ccgctccccc ggccgccgtc gtcagcagcc ccccgccccc   1440
gcctccaccg tccgccgcac ctcgccgcaa gcagccagcg cgtaagaacc tctccctctc   1500
cctctctctc tccctctcgc ctgcatctcg ctatgtttat ccatgtccat atgttgatca   1560
gccttgttta gttactaaca tgtgcaccgg atcgggttct cgcagacgac gcaccaccgc   1620
cgccaccgcc gtcgagcgag aagccgtcgt ccccgccgcc gtcccaggac cacgacggcg   1680 ccgcccccg cgccaaggcc gcgcccgccc aggcggccac ctccacgctc gcgcccgccg    1740
ccgccgccac cgccccgccg ccccaggcgc cgcactccgc cgcgcccacg cgccgtcca    1800 aggcggcctt cttcttcgtc gccacggcca tgctcggcct ctacatcatc ctctga       1856
```

<210> SEQ ID NO 4
<211> LENGTH: 220
<212> TYPE: PRT
<213> ORGANISM: triticum aestivum

<400> SEQUENCE: 4

Met Glu Arg Ser Arg Gly Leu Leu Val Ala Gly Leu Leu Ala Ala
1               5                   10                  15

Leu Leu Pro Ala Ala Ala Ala Gln Pro Gly Ala Pro Cys Glu Pro Ala
            20                  25                  30

Leu Leu Ala Thr Gln Val Ala Leu Phe Cys Ala Pro Asp Met Pro Thr
        35                  40                  45

Ala Gln Cys Cys Glu Pro Val Val Ala Val Asp Leu Gly Gly Gly
    50                  55                  60

Val Pro Cys Leu Cys Arg Val Ala Ala Glu Pro Gln Leu Val Met Ala
65                  70                  75                  80

```
Gly Leu Asn Ala Thr His Leu Leu Thr Leu Tyr Ser Ser Cys Gly Gly
                85                  90                  95

Leu Arg Pro Gly Gly Ala His Leu Ala Ala Cys Glu Gly Pro Ala
            100                 105                 110

Pro Pro Ala Ala Val Val Ser Ser Pro Pro Pro Pro Pro Pro Ser
            115                 120                 125

Ala Ala Pro Arg Arg Lys Gln Pro Ala His Asp Ala Pro Pro Pro
    130                 135                 140

Pro Pro Ser Ser Glu Lys Pro Ser Ser Pro Pro Ser Gln Asp His
145                 150                 155                 160

Asp Gly Ala Ala Pro Arg Ala Lys Ala Ala Pro Ala Gln Ala Ala Thr
                165                 170                 175

Ser Thr Leu Ala Pro Ala Ala Ala Ala Thr Ala Pro Pro Gln Ala
            180                 185                 190

Pro His Ser Ala Ala Pro Thr Ala Pro Ser Lys Ala Ala Phe Phe Phe
        195                 200                 205

Val Ala Thr Ala Met Leu Gly Leu Tyr Ile Ile Leu
    210                 215                 220

<210> SEQ ID NO 5
<211> LENGTH: 1895
<212> TYPE: DNA
<213> ORGANISM: triticum aestivum

<400> SEQUENCE: 5
atggagagat cccgcggcct gctgctggcg gcgggcctgc tggcggcgct gctgccggcg     60
gcggcggccg cgttcgggca gcagccgggg gcgccgtgcg agcccacgct gctggcgacg    120
caggtggcgc tcttctgcgc gcccgacatg cccacggccc agtgctgcga gcccgtcgtc    180
gccgccgtcg acctcggcgg cggggtgccc tgcctctgcc gcgtcgccgc ggagccgcag    240
ctcgtcatgg cgggcctcaa cgccacccac tccctcacgc tctacggctc ctgcggcggc    300
ctccgtcccg gcggcgccca cctcgccgcc gcctgcgaag gtacgtcgcg cacgttcacc    360
gcctccctcc ctccctcgct ctctctctct ctctctctct ctctctctac gtgccgattc    420
tctgtgttcg cttccctgct tacctagcac gtagttttcc atggcttctc gactcgctgg    480
tcctccgatt tgggtcggtt aatttcctcg ctgtactacc ggatctgtcg cacggcgcg    540 cggcgtcggg ttctcgccgt ctcccgtggc gagcgacctg cgcagcgcgc gcgcggccta    600
gctagcttca taccgctgta ccttcagata cacggagcga tttagggtct actctgagta    660
tttcgtcatc gtaggatgca tgtggcagtc gcgattgttt catcgatttt agatctgtgc    720
ttgttcccgc gagttaagat ggatctagcc cgtacgcag acgcagatgg tcttgctgtc    780
tctgttgctc gagttatctt atctactgtc gttcgagtat atttgcctgc ttccttttga    840
tctgtgttta tcgtgcagta gcagtagcca tgtccacgcc ttcttgtttc gaggcgatca    900
tcgtcgagat agcgctttgt ttcaaaccgc aacgcagcct ttgctttctg cggtatcttc    960
tgccttgttt ttgttctgtg cagtacgtct tgcttggtca aaagtaaaaa ctcttgctgt   1020
tcgatcgacc gaggcctgat gcagagcaag agctggccgt gcttttcgct gcagtgca    1080 tcgcctctgc ctcttttggcc aaacatttcc atgttgatcc tctggtgtgg tactactttt   1140
ttgcatgcgg tttgcgtagc cttcctcttt cgtgaaaaaa ggtcgggtcg cctattggca   1200
gagcagcagc agcagcaaca gatagctggc tgtctcgcag ctttgacaga accggtctgt   1260
ggccatctgt cgccgcctgc caccgtttcc ctgatgtttg tttctctcgt ctcatctcgc   1320
```

```
ctgccactgt tctttttctt gttgcgcacg tcgtcacctc ctcctacttt tttttccagt   1380
tttgtttact tttgagatac ggacgaacgg ctggtaatta ctaactttgg ttgctgttgt   1440
tactgtggat tttggacgca ggacccgctc ccccggccgc catcgtcagc agcccccgc    1500 ccccgccacc accgtccgcc gcacctcgcc gcaagcagcc agcgcgtacg aacctctccc   1560
tccctctctc tcgcctgcat ctcgctctgt attagctgat tgtgtttact tactgacgtg   1620
tgctttggct ttggatctgt ttcgcagacg acgcaccgcc gccgccgccg ccgtctagcg   1680
agaagccgtc gtccccgccg ccgtcccagg agcacgacgg cgccgccccc cgcgccaagg   1740
ccgcgcccgc ccaggcgacc acctcccgc tcgcgcccgc tgccgccatc gccccgccgc    1800
cccaggcgcc acactccgcg gcgcccacgg cgtcgtccaa ggcggccttc ttcttcgtcg   1860
ccacggccat gctcggcctc tacatcatcc tctga                              1895
```

<210> SEQ ID NO 6
<211> LENGTH: 223
<212> TYPE: PRT
<213> ORGANISM: triticum aestivum

<400> SEQUENCE: 6

```
Met Glu Arg Ser Arg Gly Leu Leu Leu Ala Ala Gly Leu Leu Ala
1               5                   10                  15

Leu Leu Pro Ala Ala Ala Ala Phe Gly Gln Gln Pro Gly Ala Pro
            20                  25                  30

Cys Glu Pro Thr Leu Leu Ala Thr Gln Val Ala Leu Phe Cys Ala Pro
            35                  40                  45

Asp Met Pro Thr Ala Gln Cys Cys Glu Pro Val Val Ala Ala Val Asp
        50                  55                  60

Leu Gly Gly Gly Val Pro Cys Leu Cys Arg Val Ala Ala Glu Pro Gln
65                  70                  75                  80

Leu Val Met Ala Gly Leu Asn Ala Thr His Leu Leu Thr Leu Tyr Gly
                85                  90                  95

Ser Cys Gly Gly Leu Arg Pro Gly Gly Ala His Leu Ala Ala Ala Cys
            100                 105                 110

Glu Gly Pro Ala Pro Pro Ala Ala Ile Val Ser Ser Pro Pro Pro
            115                 120                 125

Pro Pro Pro Ser Ala Ala Pro Arg Arg Lys Gln Pro Ala His Asp Ala
        130                 135                 140

Pro Pro Pro Pro Pro Ser Ser Glu Lys Pro Ser Ser Pro Pro Pro
145                 150                 155                 160

Ser Gln Glu His Asp Gly Ala Ala Pro Arg Ala Lys Ala Ala Pro Ala
                165                 170                 175

Gln Ala Thr Thr Ser Pro Leu Ala Ala Ala Ile Ala Pro Pro
            180                 185                 190

Pro Gln Ala Pro His Ser Ala Ala Pro Thr Ala Ser Ser Lys Ala Ala
        195                 200                 205

Phe Phe Phe Val Ala Thr Ala Met Leu Gly Leu Tyr Ile Ile Leu
    210                 215                 220
```

<210> SEQ ID NO 7
<211> LENGTH: 1694
<212> TYPE: DNA
<213> ORGANISM: triticum aestivum

<400> SEQUENCE: 7

| | |
|---|---|
| atggccccca ccgccctcct catcgtcgtc ctcgccgtcg ctgccctcca cgccccgcc | 60 |
| gcctccgccg cgttgtccca ggagccacca gcgacgccgt gcgcggcagc catcgtgtcc | 120 |
| ttctcgccgt gcctggcgca cgtcgcggtg gtggcgccgc ccgccctgcc ctcgcccgcg | 180 |
| cccaccagcg cctgctgcgc ggcgttcctg cgcgccgttt cctccgggga cggcgaaggc | 240 |
| ggcggagggg agggatgctt ctgccacctg ctccgcaacc cgctcctcct cggcttcccc | 300 |
| gtcgacgccg cgcgcctcgg cactctcctc cccacctgcg cctccgcgaa acctccgcc | 360 |
| gccacggccg ccgaggccga ggccctcttc gccgacaagt gccgaggtga aaatctgtc | 420 |
| ccttcgtgct ccctatttat gctcgtgcaa tatgtatgct tcgatcaatt ctcgtgcgcc | 480 |
| atatgcgcgt gctgtcgcgt tcctgttgtt gatcgccgat cgaagcaaat tttactctgc | 540 |
| aaagtcctaa ctactgttgt tctcatgatc cttgtacaac tactttcgta atggttggtt | 600 |
| gtaatgcgga ttactgacga gctctgaatg ctactaggga tattagcact tgcattactg | 660 |
| aactagtgga atgggggaga aacaccgcgg gattttcctt ttgttattaa ggagaagata | 720 |
| ctgagtggcc cagacttact tctgcgtttt tgctgcgatt tgtcatgatt accgttgatt | 780 |
| taagcagttt gttgggttgc ttgtttgata gtagtagtaa tttcacaaaa tattggcgat | 840 |
| atttataaat agctaagggc ttcgttactt ggtggtttct ctcaaagagt tcacaaaagt | 900 |
| caattattaa attcaattaa gggggcaagt attagtagta ctggctaact ccatttgcca | 960 |
| tttgccaatt gaaacagagc tcaagtcact gcctgagatg cattttacac ctccatcgcc | 1020 |
| acctcccgca ccaaaacttt ctccaggtaa atgttctgct gcttgtctaa tgattccata | 1080 |
| gcttgttaaa aaaaatgatt ccataaatct gtgcccagta atgctatttc ggatttcggt | 1140 |
| tgaatgaacc aattggcatt tgggcagaca tgtcatatgt cctctcctac caaatgaaac | 1200 |
| ttgaacttgt tttatcttgt ggtgctccat ccatttcgtg ttctatgcca caactgtaca | 1260 |
| ggttcaaatg atagtagaac aactaatttt gcatcggata ctctctgcag cctctgttct | 1320 |
| gttcctacta attgcaggac cgagtctgtc tttgtgatac tatctgcttt gcgtgcactg | 1380 |
| ctcttttagg ttgcagctgc accttctatt tgttcacct gagcattcca ttttggtcga | 1440 |
| ctgaacaccg caagtcctga atatctttct tgaatcgtcg gtcttacttg gtgtgcacta | 1500 |
| gttaaactgc tgtgtatgcc cttgcagctg ccgttacaga accagcgtcc ccgactccga | 1560 |
| agatggagga gcattcgacc tcgacgacgc ctgtgtcgga tgatcggtcg ggatccgatg | 1620 |
| ccttgtgtgc ctgccgggtc ttccttgtgg ccttggtctt gggagcagca gtcttgatca | 1680 |
| cgctgcagtt ctga | 1694 |

<210> SEQ ID NO 8
<211> LENGTH: 213
<212> TYPE: PRT
<213> ORGANISM: triticum aestivum

<400> SEQUENCE: 8

Met Ala Pro Thr Ala Leu Leu Ile Val Val Leu Ala Val Ala Ala Leu
1               5                   10                  15

His Ala Pro Ala Ala Ser Ala Ala Leu Ser Gln Glu Pro Pro Ala Thr
            20                  25                  30

Pro Cys Ala Ala Ala Ile Val Ser Phe Ser Pro Cys Leu Ala His Val
        35                  40                  45

Ala Val Val Ala Pro Pro Ala Leu Pro Ser Pro Ala Pro Thr Ser Ala
    50                  55                  60

Cys Cys Ala Ala Phe Leu Arg Ala Val Ser Ser Gly Asp Gly Glu Gly

```
                65                  70                  75                  80
Gly Gly Gly Glu Gly Cys Phe Cys His Leu Leu Arg Asn Pro Leu Leu
                    85                  90                  95

Leu Gly Phe Pro Val Asp Ala Ala Arg Leu Gly Thr Leu Leu Pro Thr
            100                 105                 110

Cys Ala Ser Ala Lys Thr Ser Ala Ala Thr Ala Ala Glu Ala Glu Ala
        115                 120                 125

Leu Phe Ala Asp Lys Cys Arg Glu Leu Lys Ser Leu Pro Glu Met His
    130                 135                 140

Phe Thr Pro Pro Ser Pro Pro Ala Pro Lys Leu Ser Pro Ala Ala
145                 150                 155                 160

Val Thr Glu Pro Ala Ser Pro Thr Pro Lys Met Glu Glu His Ser Thr
                165                 170                 175

Ser Thr Thr Pro Val Ser Asp Asp Arg Ser Gly Ser Asp Ala Leu Cys
            180                 185                 190

Ala Cys Arg Val Phe Leu Val Ala Leu Val Leu Gly Ala Ala Val Leu
        195                 200                 205

Ile Thr Leu Gln Phe
    210

<210> SEQ ID NO 9
<211> LENGTH: 1629
<212> TYPE: DNA
<213> ORGANISM: triticum aestivum

<400> SEQUENCE: 9 atgccccca   ccgccctcct  cctcgtcgtc  ctcgccgtcg  ccgccctcca  cgccctgcc      60 gcctccgccg  cgttgtccca  ggagccacca  gcgacgccgt  gcgcggcggc  catcgtgtcc    120
ttctcgccgt  gcctggcgcc  gtcgcggtgg  tggcgccgcc  cgccctgccc  tctcccgcgc    180
ccaccagcgc  ctgctgcgcg  cgttcctgc   gcgccgtttc  cgccggggac  ggcgaaggcg    240
gcggagggga  gggatgcttc  tgccacctgc  tccgcgaccc  gctcctcctc  ggcttccccg    300
tcgacgccgc  cgcgcctcggc gctctcctcc  ccacctgcgc  ctccgcgaaa  acctccgccg    360
ccacggccgt  cgaggctgag  gccctcttcg  ccgacaagtg  ccgaggtgag  aaatctgtcc    420
cttcgtgctc  cctatttatg  ctcgtgcaat  atgcatgctt  cgatcaattc  tcgtgcgcca    480
tatgcgcgag  ctgtcgcgtt  cctgttgttg  atcgccgatc  gaaacaaatc  ttactctgca    540
aagccctaac  tactgttgtt  ctcatgatcc  ttgtacaact  actttcgtaa  tggttggttg    600
taatgcggat  tactgacgag  ctctggatgc  tactagggat  attagtactt  gcatttctga    660
actagttgaa  tgggggagaa  acaccgcggg  attttctttt  tgtggcccag  acttacttct    720 gcattttgc   tgcgatttgt  catgattacc  gttcagttaa  gcagtttgtt  gggttgcttg    780
tttgatagta  gtaatttcac  aaaatattgg  cgatatttat  aaatagctaa  aggcttcgtt    840
acttggtggt  ttctctcaaa  gagttcacaa  aagtcaatca  ttaaatcaat  taaggggca    900 agtattagta  gtactggcta  actccatttg  ccattgaaac  agagctcaag  tcactgcctg    960
agatgcattt  tacacctcca  tcgccacctc  ccgccaccaaa actttctcca  ggtaaacgtt  1020
ctccctcttg  tctaatgatt  tgataaatct  gtgcccagtc  tattcgggtt  tcggttgaat  1080
aaaccaattg  gcatttgggc  agcatgttat  atggtctctc  ctcatcccaa  ataaaacttg  1140
aacttgtttt  atcttgccgt  gctccgtcca  ttttgtgctc  tatgccgcaa  ttgcacaggt  1200
tcaatgatag  tagaacacct  agttttgcat  cgcatactct  ctgcagcctc  tgttctgttc  1260
```

```
ctgctaattg cagtatcgtg tctgtctttg tgatactatc tcctttgcat gcactgcact    1320
tttaggttgc agttgcacgt ttgattctag tttgttcacc tgagcattcc attttggtcg    1380
actgaacacc gcaagtcctg aatatctttc ttgaatcgtc ggtcgtactt cgtgtgcact    1440
agttaaactg ctgtctatgc ccttgcagct gccgttccag aaccagcgtc cccgaagatg    1500
gaggagcatt cgacctcagc gacgcctgtg ccggatgatc ggtcgggatc cgatgccttg    1560
tgtgcctgcc gggtcttcct tgtggccttg gtcttgggag cagcagtctt gatcacgctg    1620
cagttctga                                                            1629
```

<210> SEQ ID NO 10
<211> LENGTH: 205
<212> TYPE: PRT
<213> ORGANISM: triticum aestivum

<400> SEQUENCE: 10

```
Met Pro Pro Thr Ala Leu Leu Val Val Leu Ala Val Ala Ala Leu
1               5                   10                  15

His Ala Pro Ala Ala Ser Ala Ala Leu Ser Gln Glu Pro Pro Ala Thr
                20                  25                  30

Pro Cys Ala Ala Ala Ile Val Ser Phe Ser Pro Cys Leu Ala Pro Ser
            35                  40                  45

Arg Trp Trp Arg Arg Pro Pro Cys Pro Leu Pro Arg Pro Pro Ala Pro
    50                  55                  60

Ala Ala Arg Arg Ser Cys Ala Pro Phe Pro Pro Gly Thr Ala Lys Ala
65                  70                  75                  80

Ala Glu Gly Arg Asp Ala Ser Ala Thr Cys Ser Ala Thr Arg Ser Ser
                85                  90                  95

Ser Ala Ser Pro Ser Thr Pro Arg Ala Ser Ala Leu Ser Ser Pro Pro
            100                 105                 110

Ala Pro Pro Arg Lys Pro Pro Pro Arg Pro Ser Arg Leu Arg Pro
        115                 120                 125

Ser Ser Pro Thr Ser Ala Glu Ser Ser Ser His Cys Leu Arg Cys Ile
    130                 135                 140

Leu His Leu His Arg His Leu Pro His Gln Asn Phe Leu Gln Leu Pro
145                 150                 155                 160

Phe Gln Asn Gln Arg Pro Arg Arg Trp Arg Ser Ile Arg Pro Gln Arg
                165                 170                 175

Arg Leu Cys Arg Met Ile Gly Arg Asp Pro Met Pro Cys Val Pro Ala
            180                 185                 190

Gly Ser Ser Leu Trp Pro Trp Ser Trp Glu Gln Ser
        195                 200                 205
```

<210> SEQ ID NO 11
<211> LENGTH: 107
<212> TYPE: PRT
<213> ORGANISM: triticum aestivum

<400> SEQUENCE: 11

```
Met Ala Pro Thr Ala Leu Leu Val Val Leu Ala Val Ala Ala Leu
1               5                   10                  15

His Ala Pro Ala Ala Ser Ala Ala Leu Ser Gln Glu Pro Pro Ala Met
                20                  25                  30

Arg Asp Phe Ser Phe Ser Ser His Cys Leu Arg Cys Ile Leu His
            35                  40                  45

Leu His Arg His Leu Pro His Gln Asn Phe Leu Gln Leu Pro Phe Gln
```

```
            50                  55                  60
Asn Gln Arg Pro Arg Trp Arg Ser Ile Arg Pro Gln Arg Arg Leu
 65                  70                  75                  80

Cys Arg Met Ile Gly Arg Asp Pro Met Pro Cys Val Pro Ala Gly Ser
                 85                  90                  95

Ser Leu Trp Pro Trp Ser Trp Glu Gln Gln Ser
            100                 105
```

<210> SEQ ID NO 12
<211> LENGTH: 1665
<212> TYPE: DNA
<213> ORGANISM: triticum aestivum

<400> SEQUENCE: 12

| | | | | | |
|---|---|---|---|---|---|
| atggccccca | ccgccctcct | cctcgtcgtc | ctcgccgtcg | ccgccctcca | cgccccgcc | 60 |
| gccaacgccg | cgttgtccca | ggagccacca | gcgaccccgt | gcgcggcggc | catcgtgtcc | 120 |
| ttctcgccgt | gcctggcgca | cgtcgcggtg | gtggcgccgc | ccgccctgcc | ctcgcccgcg | 180 |
| cccaccagcg | cctgctgcgc | ggcgttcctg | cgcgccgttt | ccgccgggga | cggcgaaggc | 240 |
| ggcggagggg | agggatgcct | ctgccacctg | ctccgcgacc | cgctcctcct | cggcttcccc | 300 |
| gtcgacgccg | cgcgcctcgg | cgctctcctc | cccacctgcg | cctccgcgaa | acctccgcc | 360 |
| gccacgccg | tcgaggccga | ggccctcttc | gccgacaagt | gccgaggtga | gaaatctgtc | 420 |
| ccttcgtgct | ccctatttat | gctcgtgcaa | tatgtatgct | ccgatcaatt | ctcgtgcgcc | 480 |
| atatgcgcgt | gctgtcgcgt | tcctgttgtt | gatcgccgac | cgaaacaaat | tttactctgc | 540 |
| aaagtcctaa | ctactgttgt | tctcattatc | ctcgtacaac | tactttcgta | atggttggtt | 600 |
| gtaatgcgga | ttactgacga | gctctggatg | ctactaggga | tattagtact | tgcatttctg | 660 |
| aactagtgga | tggggagaa | agcgggattt | ttcttttgtg | gcccagactt | acttctgcat | 720 |
| ttttgctgcg | atttgtcatg | attaccgttc | agttaagcag | tttgctgggt | tgcctgtttg | 780 |
| atagtagtaa | tttcacaaaa | tattggcgat | atttataaat | agctaagggc | ttcgttactt | 840 |
| ggtggtttct | ctcaaagagt | tcacaaaagt | caatcattaa | attcaattaa | ggggcaagt | 900 |
| attagtagta | ctggctaact | ccatttgcca | tttgccaatt | gaaacagagc | tcaagtcact | 960 |
| gcctgagatg | cattttacac | ctccatcgcc | acctcccgca | ccaaaacttt | ctccaggtaa | 1020 |
| atgttctgct | gcttgtctaa | tgattccata | gctcgtcaaa | aaaaaaatga | ttccataaat | 1080 |
| ctgtgcccag | taatgctatt | tcggatttcg | gttgaatgaa | ccaattggca | tttgggcaga | 1140 |
| catgtcatat | ttctttcctc | ccaaatgaaa | cttgaacttg | ttttatcttg | tggtgctcca | 1200 |
| tccatttcgt | gctctatgcc | gcaactgtac | aggttgaaat | gatagtagaa | catctaattt | 1260 |
| tgcatcggat | actctctgca | gcctctgttc | tgtttctact | aattgcagga | tcgagtctgt | 1320 |
| ctttgtgata | ctatctgctt | tgcgtgcact | gctcttttag | gttgcagctg | caccttctat | 1380 |
| tttgttcacc | tgagcattcc | atttggtcg | actgaacacc | gcaagtcctg | aatatctttc | 1440 |
| ttgaatcgtc | ggtcgtactt | cgtgtgcact | agttaaactg | ctgtgtatgc | ccttgcagct | 1500 |
| gccgttccag | aaccagcgtc | cccgactccg | aagatggagg | agcattcgac | ctcgacgacg | 1560 |
| tccatgtcgg | atgatcggtc | gggatctgat | gccttgtgtg | cctgccgggt | cttccttgtg | 1620 |
| gccttggtct | tgggagcagc | agtcttgatc | acgctgcagt | tctga | | 1665 |

<210> SEQ ID NO 13
<211> LENGTH: 213
<212> TYPE: PRT

<213> ORGANISM: triticum aestivum

<400> SEQUENCE: 13

```
Met Ala Pro Thr Ala Leu Leu Val Val Leu Ala Val Ala Leu
1               5                   10                  15

His Ala Pro Ala Ala Asn Ala Ala Leu Ser Gln Glu Pro Pro Ala Thr
            20                  25                  30

Pro Cys Ala Ala Ala Ile Val Ser Phe Ser Pro Cys Leu Ala His Val
        35                  40                  45

Ala Val Val Ala Pro Pro Ala Leu Pro Ser Pro Ala Pro Thr Ser Ala
    50                  55                  60

Cys Cys Ala Ala Phe Leu Arg Ala Val Ser Ala Gly Asp Gly Glu Gly
65                  70                  75                  80

Gly Gly Gly Glu Gly Cys Leu Cys His Leu Leu Arg Asp Pro Leu Leu
                85                  90                  95

Leu Gly Phe Pro Val Asp Ala Ala Arg Leu Gly Ala Leu Leu Pro Thr
            100                 105                 110

Cys Ala Ser Ala Lys Thr Ser Ala Ala Thr Ala Val Glu Ala Glu Ala
        115                 120                 125

Leu Phe Ala Asp Lys Cys Arg Glu Leu Lys Ser Leu Pro Glu Met His
    130                 135                 140

Phe Thr Pro Pro Ser Pro Pro Ala Pro Lys Leu Ser Pro Ala Ala
145                 150                 155                 160

Val Pro Glu Pro Ala Ser Pro Thr Pro Lys Met Glu Glu His Ser Thr
                165                 170                 175

Ser Thr Thr Ser Met Ser Asp Asp Arg Ser Gly Ser Asp Ala Leu Cys
            180                 185                 190

Ala Cys Arg Val Phe Leu Val Ala Leu Val Leu Gly Ala Ala Val Leu
        195                 200                 205

Ile Thr Leu Gln Phe
    210
```

<210> SEQ ID NO 14
<211> LENGTH: 1666
<212> TYPE: DNA
<213> ORGANISM: triticum aestivum

<400> SEQUENCE: 14

```
atggccccca ccgccctcct cctcgtcgtc ctcgccgtcg ccgccctcca cgccccgcc    60 gccaacgccg cgttgtcccc aggagccacc agcgaccccg tgcgcggcgg ccatcgtgtc   120
cttctcgccg tgcctggcgc acgtcgcggt ggtggcgccg ccgccctgc cctcgcccgc    180 gccaccagc gcctgctgcg cggcgttcct cgcgccgtt ccgccgggg acggcgaagg      240 cggcggaggg gagggatgcc tctgccacct gctccgcgac ccgctcctcc tcggcttccc   300
cgtcgacgcc gcgcgcctcg gcgctctcct ccccacctgc gcctccgcga aaacctccgc   360
cgccacggcc gtcgaggccg aggccctctt cgccgacaag tgccgaggtg agaaatctgt   420
cccttcgtgc tccctattta tgctcgtgca atatgtatgc tccgatcaat tctcgtgcgc   480
catatgcgcg tgctgtcgcg ttcctgttgt tgatcgccga ccgaaacaaa ttttactctg   540
caaagtccta actactgttg ttctcattat cctcgtacaa ctactttcgt aatggttggt   600
tgtaatgcgg attactgacg agctctggat gctactaggg atattagtac ttgcatttct   660
gaactagtgg atgggggaga aagcgggatt tttcttttgt ggcccagact tacttctgca   720
tttttgctgc gatttgtcat gattaccgtt cagttaagca gtttgctggg ttgcctgttt   780
```

```
gatagtagta atttcacaaa atattggcga tatttataaa tagctaaggg cttcgttact    840
tggtggtttc tctcaaagag ttcacaaaag tcaatcatta aattcaatta aggggggcaag   900
tattagtagt actggctaac tccatttgcc atttgccaat tgaaacagag ctcaagtcac    960
tgcctgagat gcattttaca cctccatcgc cacctcccgc accaaaactt tctccaggta   1020
aatgttctgc tgcttgtcta atgattccat agctcgtcaa aaaaaaaatg attccataaa   1080
tctgtgccca gtaatgctat ttcggatttc ggttgaatga accaattggc atttgggcag   1140
acatgtcata tttctttcct cccaaatgaa acttgaactt gttttatctt gtggtgctcc   1200
atccatttcg tgctctatgc cgcaactgta caggttgaaa tgatagtaga acatctaatt   1260
ttgcatcgga tactctctgc agcctctgtt ctgtttctac taattgcagg atcgagtctg   1320
tctttgtgat actatctgct ttgcgtgcac tgctcttta  ggttgcagct gcaccttcta   1380
ttttgttcac ctgagcattc cattttggtc gactgaacac cgcaagtcct gaatatcttt   1440
cttgaatcgt cggtcgtact tcgtgtgcac tagttaaact gctgtgtatg cccttgcagc   1500
tgccgttcca gaaccagcgt ccccgactcc gaagatggag gagcattcga cctcgacgac   1560
gtccatgtcg gatgatcggt cgggatctga tgccttgtgt gcctgccggg tcttccttgt   1620
ggccttggtc ttgggagcag cagtcttgat cacgctgcag ttctga               1666
```

<210> SEQ ID NO 15
<211> LENGTH: 141
<212> TYPE: PRT
<213> ORGANISM: triticum aestivum

<400> SEQUENCE: 15

Met Ala Pro Thr Ala Leu Leu Leu Val Val Leu Ala Val Ala Ala Leu
1               5                   10                  15

His Ala Pro Ala Ala Asn Ala Ala Leu Ser Pro Gly Ala Thr Ser Asp
                20                  25                  30

Pro Val Arg Gly Gly His Arg Val Leu Leu Ala Val Pro Gly Ala Arg
            35                  40                  45

Arg Gly Gly Gly Ala Ala Arg Pro Ala Leu Ala Arg Ala His Gln Arg
        50                  55                  60

Leu Leu Arg Gly Val Pro Ala Arg Arg Phe Arg Arg Gly Arg Arg Arg
65                  70                  75                  80

Arg Arg Arg Gly Gly Met Pro Leu Pro Pro Ala Pro Arg Pro Ala Pro
                85                  90                  95

Pro Arg Leu Pro Arg Arg Arg Arg Ala Pro Arg Ser Pro Pro His
            100                 105                 110

Leu Arg Leu Arg Glu Asn Leu Arg Arg His Gly Arg Arg Gly Arg Gly
        115                 120                 125

Pro Leu Arg Arg Gln Val Pro Arg Ala Gln Val Thr Ala
    130                 135                 140

<210> SEQ ID NO 16
<211> LENGTH: 1525
<212> TYPE: DNA
<213> ORGANISM: triticum aestivum

<400> SEQUENCE: 16
atggggcggc cgccgtgctg cgacaaggcc aacgtgaaga aggggccgtg gacggcggag     60
gaggacgcca agctgctggc ctacacctcc aaccatggcc ccgcaactg gacctctgtt    120
ccccagaggg caggtcggaa ccctctcccc cggccggccg gatcggcgtc tggcatcgaa    180

-continued

```
atggtgttgg ttttgcatgg tttctggctg atgtgtgttg cgtcatggat gggtgcgtgc      240
tgcagggctg aagcggtgcg ggaagagctg caggctgagg tacaccaact acctgaggcc      300
caacctcaag cacgagaact tcacgcagga ggaggaggag ctcatcgtca ccctccatgc      360
catgctggga agcaggtgca tctctgtaca tgcatgtcat ccatcggtta ctttctcgat      420
tttgtcatca gttttcggt gaatgcgaaa ctttgctatg acagactac tgtttctgtc        480
atcattcctg ctataaactt tgcatccata tactctagcg tacgttcaga tcttatagat      540
ttatggaagt tctaaaaacc tcacgttggt gtatcattca dacaattgct catacaccgg      600
aaatcacgtc ctacttctat tcaagaattt actttagccg ttcattcata agtagaaac       660
aaatgtagtt taatccagta accagtctcg tgtctacggt tcttctgaat atattctgtt      720
tcctggtaga atgtagtgaa aagctgaata ttgggtgaag aacagatctg aatagctgtc      780
ttaaattgat agtgtttgac agaaaatact ccacactgag cgtaatataa catgaaagta      840
cgtgtacgtg ttgggtgcat gcaggtggtc tctgatcgcg aaccagctgc cggggcggac      900
ggacaacgac gtcaagaatt actggaacac caagctgagc aagaagctgc ggcagcgggg      960
catcgacccc atcacccatc gccccatcgc cgacctcatg cagagcatcg gcaccctccc     1020
catccgcccg ccgcccagcg ccgcgggtgc ctcctcgtcc tctacatcc ccgtgaaccc      1080
agcggcggcg ccggggctcc agccgctgca cgacgacgtc aaataccacg cagtcctgaa     1140
ccaccaccag cagcaggtca tcacgctcct cgacccagac gcgccagggg cggcggcgtc     1200
cccggaccac cagctcaagt ggagcgactt ccttgccgac gacgccgccg ccttcgaggc     1260
ggcgccgcag gtggttcttg gtcagtacca ggaggccgcg gtggctggtg gcggagcagc     1320
gtatggagac actgatagta ttgcagccga tggtgtcggc gggggcgggg aggatagcgc     1380
agcgtcagcg ttcatcgacg cgatgctgga cagcgacaaa aagatgggcg tggaccagct     1440
catcgccgac ctgctcgccg acccggcata ctactacggc ggaggctctt cctcttcgac     1500
gtcggagctg gggcggggcg gttga                                          1525
```

<210> SEQ ID NO 17
<211> LENGTH: 307
<212> TYPE: PRT
<213> ORGANISM: triticum aestivum

<400> SEQUENCE: 17

```
Met Gly Arg Pro Pro Cys Cys Asp Lys Ala Asn Val Lys Lys Gly Pro
1               5                   10                  15

Trp Thr Ala Glu Glu Asp Ala Lys Leu Leu Ala Tyr Thr Ser Asn His
            20                  25                  30

Gly Thr Gly Asn Trp Thr Ser Val Pro Gln Arg Ala Gly Leu Lys Arg
        35                  40                  45

Cys Gly Lys Ser Cys Arg Leu Arg Tyr Thr Asn Tyr Leu Arg Pro Asn
    50                  55                  60

Leu Lys His Glu Asn Phe Thr Gln Glu Glu Glu Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110

Ser Lys Lys Leu Arg Gln Arg Gly Ile Asp Pro Ile Thr His Arg Pro
        115                 120                 125
```

```
Ile Ala Asp Leu Met Gln Ser Ile Gly Thr Leu Pro Ile Arg Pro Pro
    130                 135                 140

Pro Ser Ala Ala Gly Ala Ser Ser Ser Tyr Ile Pro Val Asn Pro
145                 150                 155                 160

Ala Ala Ala Pro Gly Leu Gln Pro Leu His Asp Asp Val Lys Tyr His
                165                 170                 175

Ala Val Leu Asn His His Gln Gln Val Ile Thr Leu Leu Asp Pro
            180                 185                 190

Asp Ala Pro Gly Ala Ala Ala Ser Pro Asp His Gln Leu Lys Trp Ser
            195                 200                 205

Asp Phe Leu Ala Asp Ala Ala Ala Phe Glu Ala Ala Pro Gln Val
    210                 215                 220

Val Leu Gly Gln Tyr Gln Glu Ala Ala Val Ala Gly Gly Ala Ala
225                 230                 235                 240

Tyr Gly Asp Thr Asp Ser Ile Ala Ala Asp Gly Val Gly Gly Gly
                245                 250                 255

Glu Asp Ser Ala Ala Ser Ala Phe Ile Asp Ala Met Leu Asp Ser Asp
            260                 265                 270

Lys Lys Met Gly Val Asp Gln Leu Ile Ala Asp Leu Leu Ala Asp Pro
            275                 280                 285

Ala Tyr Tyr Tyr Gly Gly Gly Ser Ser Ser Ser Thr Ser Glu Leu Gly
    290                 295                 300

Arg Gly Gly
305

<210> SEQ ID NO 18
<211> LENGTH: 1530
<212> TYPE: DNA
<213> ORGANISM: triticum aestivum

<400> SEQUENCE: 18
atggggcggc cgccgtgctg cgacaaggcc aacgtgaaga aggggccgtg gacggcggag      60
gaggacgcca agctgctcgc ctacacctcc aaccatggca ccggcaactg gacctctgtt     120
ccccagaggg caggtcggaa ccctcccccc ggcggccgg atcgacgtcc gtcatggaaa     180
tggtgttggt cttgcatggt ttctggctga tgtgtgttgc atcatggatg cgtgcgtgct     240
gcagggctga gcggtgcgg gaagagctgc aggctgaggt acaccaacta cctgaggccc     300
aacctcaagc acgagaactt cacgcaggag gaggaggagc tcatcgtcac cctccatgcc     360
atgctgggaa gcaggtgcgt ctctctgtgt agtacatgca tgtttctgcc atcagttact     420
ttctcgattt tgtcatcaag ttttcggtga atgcgaaact ttgctatgga ccgactgctg     480
tttctgtcat cattcctgct ataaaccttg catccatata ctctagcgtt cagatcttat     540
agatttatgg aagttctgaa tatctcacgt tggtgtatca gacaattgct catataccgg     600
aaatcacgtc ctacttctat tcaagaattt acttcagtcg ttcgttcaaa aatagaaaga     660
aatgtagttt agtccagtga ccagtctcgt gtctacgtac ggttcttctg aatatatata     720
ttctgtttcc tggtagaatg tagtgaaaag ctgaaaattc ggtgaagaac atatctgaat     780
agctgtctta aattgatagt gtttgacaga aaatactcca cactgagcgt aacgtgaaag     840
tgcgtgtacg tgttgggtgc atgcaggtgg tctctgatcg cgaaccagct gccggggcgg     900
acggacaacg acgtcaagaa ctactggaac accaagctga gcaagaagct gaggcagcgg     960
ggcatcgacc catcacccca ccgccccatc gccgatctca tgcagagcat cggcacccte    1020 gccatccgcc cgccaccgag cgccgcgggt gcctcctcct cctcctacct ccccgtgaac    1080
```

-continued

```
ccaccggcgg cgccggggct ccagccgctg cacgacgacg tcaaatacca cacagtcctg    1140
aaccagcagc agcagcaggt catcacgctc ctcgaccccg acgcgccagg ggcggcggcg    1200
tccccggagc accagctcaa gtggagcgac ttcctcgcgg acgacgccgc ggccctcgag    1260
gcggcgccag aggtcgttct tggtcagtac caggaggcca cggtcgctgg tggcggagca    1320
cacgcgtatg gcgacactga cagtactgca gccgatggtg tcggcggggg cggggacgat    1380
agcgcagcgt cagcgttcat cgacgcgatg ctggacagcg acaagaagat gggcgtggac    1440
cagctcatcg ccgacctgct cgccgacccg gcatactact acggcggagg ctcttcctct    1500
tcgacgtcgg agctggggtg gggctgttga                                     1530
```

<210> SEQ ID NO 19
<211> LENGTH: 308
<212> TYPE: PRT
<213> ORGANISM: triticum aestivum

<400> SEQUENCE: 19

```
Met Gly Arg Pro Pro Cys Cys Asp Lys Ala Asn Val Lys Lys Gly Pro
1               5                   10                  15

Trp Thr Ala Glu Glu Asp Ala Lys Leu Leu Ala Tyr Thr Ser Asn His
            20                  25                  30

Gly Thr Gly Asn Trp Thr Ser Val Pro Gln Arg Ala Gly Leu Lys Arg
        35                  40                  45

Cys Gly Lys Ser Cys Arg Leu Arg Tyr Thr Asn Tyr Leu Arg Pro Asn
    50                  55                  60

Leu Lys His Glu Asn Phe Thr Gln Glu Glu Glu Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110

Ser Lys Lys Leu Arg Gln Arg Gly Ile Asp Pro Ile Thr His Arg Pro
        115                 120                 125

Ile Ala Asp Leu Met Gln Ser Ile Gly Thr Leu Ala Ile Arg Pro Pro
    130                 135                 140

Pro Ser Ala Ala Gly Ala Ser Ser Ser Tyr Leu Pro Val Asn Pro
145                 150                 155                 160

Ala Ala Ala Pro Gly Leu Gln Pro Leu His Asp Asp Val Lys Tyr His
                165                 170                 175

Ala Val Leu Asn Gln Gln Gln Gln Val Ile Thr Leu Leu Asp Ala
            180                 185                 190

Asp Ala Pro Gly Ala Ala Ala Ser Pro Asp His Pro Leu Lys Trp Ser
        195                 200                 205

Asp Phe Leu Ala Asp Asp Ala Ala Phe Glu Ala Ala Pro Gln Val
    210                 215                 220

Val Leu Gly Gln Tyr Gln Asp Ala Ala Val Ala Gly Gly Gly Ala His
225                 230                 235                 240

Ala Tyr Gly Asp Thr Asp Ser Thr Ala Ala Asp Gly Val Gly Val Gly
                245                 250                 255

Gly Glu Asp Ser Ala Ala Ser Ala Phe Ile Asp Ala Met Leu Asp Ser
            260                 265                 270

Asp Lys Lys Met Gly Val Asp Gln Leu Ile Ala Asp Leu Leu Ala Asp
        275                 280                 285
```

Pro Ala Tyr Tyr Tyr Gly Gly Gly Ser Ser Ser Thr Ser Asp Leu
        290                 295                 300

Gly Trp Gly Cys
305

<210> SEQ ID NO 20
<211> LENGTH: 1530
<212> TYPE: DNA
<213> ORGANISM: triticum aestivum

<400> SEQUENCE: 20

| | | | | | |
|---|---|---|---|---|---|
| atgggcggc | cgccgtgctg | cgacaaggcc | aacgtgaaga | aggggccgtg | gacggcggag | 60 |
| gaggacgcca | agctgctcgc | ctacacctcc | aaccatggca | ccggcaactg | gacctctgtt | 120 |
| ccccagaggg | caggtcggaa | ccctcccccc | ggccggccgg | atcgacgtcc | gtcatggaaa | 180 |
| tggtgttggt | cttgcatggt | ttctggctga | tgtgtgttgc | atcatggatg | cgtgcgtgct | 240 |
| gcagggctga | gcggtgcgg | gaagagctgc | aggctgaggt | acaccaacta | cctgaggccc | 300 |
| aacctcaagc | acgagaactt | cacgcaggag | gaggaggagc | tcatcgtcac | cctccatgcc | 360 |
| atgctgggaa | gcaggtgcgt | ctctctgtgt | agtacatgca | tgtttctgcc | atcagttact | 420 |
| ttctcgattt | tgtcatcaag | ttttcggtga | tgcgaaact | ttgctatgga | ccgactgctg | 480 |
| tttctgtcat | cattcctgct | ataaaccttg | catccatata | ctctagcgtt | cagatcttat | 540 |
| agatttatgg | aagttctgaa | tatctcacgt | tggtgtatca | gacaattgct | catataccgg | 600 |
| aaatcacgtc | ctacttctat | tcaagaattt | acttcagtcg | ttcgttcaaa | aatagaaaga | 660 |
| aatgtagttt | agtccagtga | ccagtctcgt | gtctacgtac | ggttcttctg | aatatatata | 720 |
| ttctgtttcc | tggtagaatg | tagtgaaaag | ctgaaaattc | ggtgaagaac | atatctgaat | 780 |
| agctgtctta | aattgatagt | gtttgacaga | aaatactcca | cactgagcgt | aacgtgaaag | 840 |
| tgcgtgtacg | tgttgggtgc | atgcaggtgg | tctctgatcg | cgaaccagct | gccggggcgg | 900 |
| acggacaacg | acgtcaagaa | ctactggaac | accaagctga | gcaagaagct | gaggcagcgg | 960 |
| ggcatcgacc | ccatcaccca | ccgccccatc | gccgatctca | tgcagagcat | cggcaccctc | 1020 |
| gccatccgcc | cgccaccgag | cgccgcgggt | gcctcctcct | cctcctacct | ccccgtgaac | 1080 |
| ccaccggcgg | cgccggggct | ccagccgctg | cacgacgacg | tcaaatacca | cacagtcctg | 1140 |
| aaccagcagc | agcagcaggt | catcacgctc | ctcgaccccg | acgcgccagg | ggcggcggcg | 1200 |
| tccccggagc | accagctcaa | gtggagcgac | ttcctcgcgg | acgacgccgc | ggccctcgag | 1260 |
| gcggcgccgc | aggtcgttct | tggtcagtac | caggaggccg | cggtcgctgg | tggcggagca | 1320 |
| cacgcgtatg | gcgacactga | cagtactgca | gccgatggtg | tcggcggggg | cggggacgat | 1380 |
| agcgcagcgt | cagcgttcat | cgacgcgatg | ctggacagcg | acaagaagat | gggcgtggac | 1440 |
| cagctcatcg | ccgacctgct | cgccgacccg | gcatactact | acggcggagg | ctcttcctct | 1500 |
| tcgacgtcgg | agctggggtg | gggctgttga | | | | 1530 |

<210> SEQ ID NO 21
<211> LENGTH: 308
<212> TYPE: PRT
<213> ORGANISM: triticum aestivum

<400> SEQUENCE: 21

Met Gly Arg Pro Pro Cys Cys Asp Lys Ala Asn Val Lys Lys Gly Pro
1               5                   10                  15

Trp Thr Ala Glu Glu Asp Ala Lys Leu Leu Ala Tyr Thr Ser Asn His
            20                  25                  30

Gly Thr Gly Asn Trp Thr Ser Val Pro Gln Arg Ala Gly Leu Lys Arg
            35                  40                  45

Cys Gly Lys Ser Cys Arg Leu Arg Tyr Thr Asn Tyr Leu Arg Pro Asn
        50                  55                  60

Leu Lys His Glu Asn Phe Thr Gln Glu Glu Glu Leu Ile Val Thr
65                  70                  75                  80

Leu His Ala Met Leu Gly Ser Arg Trp Ser Leu Ile Ala Asn Gln Leu
                85                  90                  95

Pro Gly Arg Thr Asp Asn Asp Val Lys Asn Tyr Trp Asn Thr Lys Leu
            100                 105                 110

Ser Lys Lys Leu Arg Gln Arg Gly Ile Asp Pro Ile Thr His Arg Pro
        115                 120                 125

Ile Ala Asp Leu Met Gln Ser Ile Gly Thr Leu Ala Ile Arg Pro Pro
    130                 135                 140

Pro Ser Ala Ala Gly Ala Ser Ser Ser Tyr Leu Pro Val Asn Pro
145                 150                 155                 160

Pro Ala Ala Pro Gly Leu Gln Pro Leu His Asp Asp Val Lys Tyr His
                165                 170                 175

Thr Val Leu Asn Gln Gln Gln Gln Val Ile Thr Leu Leu Asp Pro
            180                 185                 190

Asp Ala Pro Gly Ala Ala Ala Ser Pro Glu His Gln Leu Lys Trp Ser
        195                 200                 205

Asp Phe Leu Ala Asp Ala Ala Leu Glu Ala Pro Gln Val
    210                 215                 220

Val Leu Gly Gln Tyr Gln Glu Ala Ala Val Ala Gly Gly Gly Ala His
225                 230                 235                 240

Ala Tyr Gly Asp Thr Asp Ser Thr Ala Ala Asp Gly Val Gly Gly Gly
                245                 250                 255

Gly Asp Asp Ser Ala Ala Ser Ala Phe Ile Asp Ala Met Leu Asp Ser
            260                 265                 270

Asp Lys Lys Met Gly Val Asp Gln Leu Ile Ala Asp Leu Leu Ala Asp
        275                 280                 285

Pro Ala Tyr Tyr Tyr Gly Gly Gly Ser Ser Ser Thr Ser Glu Leu
    290                 295                 300

Gly Trp Gly Cys
305

<210> SEQ ID NO 22
<211> LENGTH: 414
<212> TYPE: DNA
<213> ORGANISM: triticum aestivum

<400> SEQUENCE: 22
atgttgagga tgcagcagca ggtggagggc gtggtgggcg gcggcatcgt ggccgaggcg      60
gaggaggcgg cggtgtacga gcgggtggct cgcatggcca cgcaacgc cgtggtcgtc      120 ttcagcgcca gcggctgctg catgtgccac gtcgtcaagc gcctcctgct tggcctggga      180
gtcggcccca ccgtctacga gttggaccag atgggcggcg ccgggcggga gatccaggcg      240
gccctggcgc agctgctgcc ccccggaccc ggcgccggcc accaccagca gccgccggtg      300
cccgtggtgt tcgtcggcgg gaggctcctg ggaggcgtgg agaaggtgat ggcgtgccac      360
atcaacggca cgctcgtccc gctcctcaag gacgccggcg cgctctggct ctga           414

<210> SEQ ID NO 23

<211> LENGTH: 137
<212> TYPE: PRT
<213> ORGANISM: triticum aestivum

<400> SEQUENCE: 23

```
Met Leu Arg Met Gln Gln Gln Val Glu Gly Val Val Gly Gly Gly Ile
1               5                   10                  15

Val Ala Glu Ala Glu Glu Ala Ala Val Tyr Glu Arg Val Ala Arg Met
            20                  25                  30

Ala Ser Gly Asn Ala Val Val Phe Ser Ala Ser Gly Cys Cys Met
        35                  40                  45

Cys His Val Val Lys Arg Leu Leu Gly Leu Gly Val Gly Pro Thr
    50                  55                  60

Val Tyr Glu Leu Asp Gln Met Gly Gly Ala Gly Arg Glu Ile Gln Ala
65              70                  75                  80

Ala Leu Ala Gln Leu Leu Pro Pro Gly Pro Gly Ala Gly His His Gln
            85                  90                  95

Gln Pro Pro Val Pro Val Val Phe Val Gly Gly Arg Leu Leu Gly Gly
            100                 105                 110

Val Glu Lys Val Met Ala Cys His Ile Asn Gly Thr Leu Val Pro Leu
            115                 120                 125

Leu Lys Asp Ala Gly Ala Leu Trp Leu
            130             135
```

<210> SEQ ID NO 24
<211> LENGTH: 414
<212> TYPE: DNA
<213> ORGANISM: triticum aestivum

<400> SEQUENCE: 24

```
atgttgagga tgcagcagca ggtggagggc gtggtgggcg gcggcatcgt ggcggaggcg    60
gaggaggcgg cggtgtacga gagggtggct cgcatggcca gcggcaacgc ggtggtcgtc   120
ttcagcgcca gcggctgctg catgtgccac gtcgtcaagc gcctcctgct tggcctggga   180
gtcggcccca ccgtgtacga gttggaccag atgggcggcg ccgggcggga gatccaggcg   240
gccctggcgc agctgctgcc ccccggaccc ggcgccggcc accaccagca gccgccggtg   300
cccgtggtgt tcgttggcgg gaggctcctg ggcggcgtgg agaaggtgat ggcgtgccac   360
atcaacggca cgctcgtccc gctcctcaag gacgccggcg cgctctggct ctga         414
```

<210> SEQ ID NO 25
<211> LENGTH: 137
<212> TYPE: PRT
<213> ORGANISM: triticum aestivum

<400> SEQUENCE: 25

```
Met Leu Arg Met Gln Gln Gln Val Glu Gly Val Val Gly Gly Gly Ile
1               5                   10                  15

Val Ala Glu Ala Glu Glu Ala Ala Val Tyr Glu Arg Val Ala Arg Met
            20                  25                  30

Ala Ser Gly Asn Ala Val Val Phe Ser Ala Ser Gly Cys Cys Met
        35                  40                  45

Cys His Val Val Lys Arg Leu Leu Gly Leu Gly Val Gly Pro Thr
    50                  55                  60

Val Tyr Glu Leu Asp Gln Met Gly Gly Ala Gly Arg Glu Ile Gln Ala
65              70                  75                  80

Ala Leu Ala Gln Leu Leu Pro Pro Gly Pro Gly Ala Gly His His Gln
```

```
                    85                  90                  95
Gln Pro Pro Val Pro Val Val Phe Val Gly Gly Arg Leu Leu Gly Gly
                100                 105                 110

Val Glu Lys Val Met Ala Cys His Ile Asn Gly Thr Leu Val Pro Leu
        115                 120                 125

Leu Lys Asp Ala Gly Ala Leu Trp Leu
    130                 135

<210> SEQ ID NO 26
<211> LENGTH: 414
<212> TYPE: DNA
<213> ORGANISM: triticum aestivum

<400> SEQUENCE: 26
atgttgagga tgcagcagca ggtggagggc gtggtgggcg gcggcatcat ggcggaggcg      60
gaggaggcgg cggtgtacga gcgggtggct cgcatggcca gcggcaacgc ggtggtcgtc     120
ttcagcgcca gcggctgctg catgtgccac gtcgtcaagc gcctcctgct tggcctgggg     180
gtcggcccca ccgtctacga gttggaccag atgggcggcg ccgggcgaga gatccaggcg     240
gcgctggcgc agctgctgcc ccccggaccc ggcgccggcc accaccagca gccgccagtg     300
cccgtggtgt tcgtcggcgg gaggctcctg ggcggcgtgg agaaggtgat ggcgtgccac     360
atcaacggca cgctcgtccc gctcctcaag gacgccggcg cgctctggct ctga           414

<210> SEQ ID NO 27
<211> LENGTH: 137
<212> TYPE: PRT
<213> ORGANISM: triticum aestivum

<400> SEQUENCE: 27

Met Leu Arg Met Gln Gln Gln Val Glu Gly Val Val Gly Gly Gly Ile
1               5                   10                  15

Met Ala Glu Ala Glu Glu Ala Ala Val Tyr Glu Arg Val Ala Arg Met
            20                  25                  30

Ala Ser Gly Asn Ala Val Val Val Phe Ser Ala Ser Gly Cys Cys Met
        35                  40                  45

Cys His Val Val Lys Arg Leu Leu Leu Gly Leu Gly Val Gly Pro Thr
    50                  55                  60

Val Tyr Glu Leu Asp Gln Met Gly Gly Ala Gly Arg Glu Ile Gln Ala
65                  70                  75                  80

Ala Leu Ala Gln Leu Leu Pro Pro Gly Pro Gly Ala Gly His His Gln
                85                  90                  95

Gln Pro Pro Val Pro Val Val Phe Val Gly Gly Arg Leu Leu Gly Gly
                100                 105                 110

Val Glu Lys Val Met Ala Cys His Ile Asn Gly Thr Leu Val Pro Leu
        115                 120                 125

Leu Lys Asp Ala Gly Ala Leu Trp Leu
    130                 135

<210> SEQ ID NO 28
<211> LENGTH: 1926
<212> TYPE: DNA
<213> ORGANISM: triticum aestivum

<400> SEQUENCE: 28
atgagcagcc ccatggagga agctcaccat ggcatgccgt cgacgacgac ggcgttcttc      60
ccgctggcag ggctccacaa gttcatggcc atcttcctcg tgttcctctc gtggatcttg     120
```

```
gtccactggt ggagcctgag gaagcagaag gggccgaggt catggccggt catcggcgcg      180
acgctggagc agctgaggaa ctactaccgg atgcacgact ggctcgtgga gtacctgtcc      240
aagcaccgga cggtcaccgt cgacatgccc ttcacctcct acacctacat cgccgacccg      300
gtgaacgtcg agcatgtgct caagaccaac ttcaacaatt accccaaggt gaaactgaaa      360
gaacccctca gccttgtgaa ttttttttgcc aaggttcaga agtttacact gacacaaatg     420
tctgaaattg tacgtgtagg gggaggtgta caggtcctac atggacgtgc tgctcggcga      480
cggcatcttc aacgccgacg gcgagctctg gaggaagcag aggaagacgg cgagcttcga      540
gttcgcttcc aagaacctga gagactttag cacgatcgtg ttcagggagt actccctgaa      600
gctgcgcagc atcctgagcc aggcttgcaa ggccggcaaa gtcgtggaca tgcaggtaac      660
cgaactcagt cccttggtca tctgaacatt gatttcttgg acaaaatttc aagattctga      720
cgcgagcgag cgaattcagg agctgtacat gaggatgacg ctggactcga tctgcaaggt      780
ggggttcggg gtcgagatcg gcacgctgtc gccggagctg ccggagaaca gcttcgcgca      840
ggcgttcgac gccgccaaca tcatcgtgac gctgcggttc atcgacccgc tgtggcgcgt      900
gaagaagttc ctgcacgtcg gctcggaggc gctgctggag cagagcatca agctcgtcga      960
cgagttcacc tacagcgtca tccgccggcg caaggccgag atcgtgcagg cccgggccag     1020
cggcaagcag gagaaggtgc gtacgtgatc gtcgtcgtca agctccggat cgctggtttg     1080
tgtaggtgcc attgatcact gacacactag ctgggtgcgc agatcaagca cgacatactg     1140
tcgcggttca tcgagctggg cgaggccggc ggggacgacg gcggcagcct gttcggggac     1200
gacaagggcc tccgcgacgt ggtgctcaac ttcgtgatcg ccgggcggga caccacggcc     1260
acgacgctct cctggttcac ctacatggcc atgacgcacc cggccgtggc cgagaagctc     1320
cgccgcgagc tggccgccct cgaggcggac cgcgcccgcg aggatggcgt cgcgctggtc     1380
ccctgcagcg actcagacgg cgacggctcc gacgaggcct tcgccgcccg cgtggcgcag     1440
ttcgcggggc tgctgagcta cgacgggctc gggaagctgg tgtacctcca cgcgtgcgtg     1500
acggagacgc tgcgcctgta cccggcggtg ccgcaggacc ccaagggcat cgcggaggac     1560
gacgtgctcc cggacggcac caaggtgcgc gccggcggga tggtgacgta cgtgccctac     1620
tccatggggc ggatggagta caactggggc cccgacgccg ccagcttccg gccggagcgg     1680
tggatcggcg acgacggcgc gttccgcaac gcgtcgccgt tcaagttcac ggcgttccag     1740
gcggggccgc ggatctgcct cggcaaggac tcggcgtacc tgcagatgaa gatggcgctg     1800
gccatcctgt gcaggttctt caggttcgag ctcgtggagg ccaccccgt caagtaccgc      1860 atgatgacca tcctctccat ggcgcacggc ctcaaggtcc gcgtctccag ggcgccgctc     1920
gcctga                                                                1926
```

<210> SEQ ID NO 29
<211> LENGTH: 554
<212> TYPE: PRT
<213> ORGANISM: triticum aestivum

<400> SEQUENCE: 29

```
Met Ser Ser Pro Met Glu Glu Ala His His Gly Met Pro Ser Thr Thr
1               5                   10                  15

Thr Ala Phe Phe Pro Leu Ala Gly Leu His Lys Phe Met Ala Ile Phe
            20                  25                  30

Leu Val Phe Leu Ser Trp Ile Leu Val His Trp Trp Ser Leu Arg Lys
        35                  40                  45
```

```
Gln Lys Gly Pro Arg Ser Trp Pro Val Ile Gly Ala Thr Leu Glu Gln
 50                  55                  60

Leu Arg Asn Tyr Tyr Arg Met His Asp Trp Leu Val Glu Tyr Leu Ser
 65                  70                  75                  80

Lys His Arg Thr Val Thr Val Asp Met Pro Phe Thr Ser Tyr Thr Tyr
                 85                  90                  95

Ile Ala Asp Pro Val Asn Val Glu His Val Leu Lys Thr Asn Phe Asn
                100                 105                 110

Asn Tyr Pro Lys Gly Glu Val Tyr Arg Ser Tyr Met Asp Val Leu Leu
            115                 120                 125

Gly Asp Gly Ile Phe Asn Ala Asp Gly Glu Leu Trp Arg Lys Gln Arg
130                 135                 140

Lys Thr Ala Ser Phe Glu Phe Ala Ser Lys Asn Leu Arg Asp Phe Ser
145                 150                 155                 160

Thr Ile Val Phe Arg Glu Tyr Ser Leu Lys Leu Arg Ser Ile Leu Ser
                165                 170                 175

Gln Ala Cys Lys Ala Gly Lys Val Val Asp Met Gln Glu Leu Tyr Met
                180                 185                 190

Arg Met Thr Leu Asp Ser Ile Cys Lys Val Gly Phe Gly Val Glu Ile
                195                 200                 205

Gly Thr Leu Ser Pro Glu Leu Pro Glu Asn Ser Phe Ala Gln Ala Phe
210                 215                 220

Asp Ala Ala Asn Ile Ile Val Thr Leu Arg Phe Ile Asp Pro Leu Trp
225                 230                 235                 240

Arg Val Lys Lys Phe Leu His Val Gly Ser Glu Ala Leu Leu Glu Gln
                245                 250                 255

Ser Ile Lys Leu Val Asp Glu Phe Thr Tyr Ser Val Ile Arg Arg Arg
                260                 265                 270

Lys Ala Glu Ile Val Gln Ala Arg Ala Ser Gly Lys Gln Glu Lys Ile
                275                 280                 285

Lys His Asp Ile Leu Ser Arg Phe Ile Glu Leu Gly Glu Ala Gly Gly
                290                 295                 300

Asp Asp Gly Gly Ser Leu Phe Gly Asp Lys Gly Leu Arg Asp Val
305                 310                 315                 320

Val Leu Asn Phe Val Ile Ala Gly Arg Asp Thr Thr Ala Thr Thr Leu
                325                 330                 335

Ser Trp Phe Thr Tyr Met Ala Met Thr His Pro Ala Val Ala Glu Lys
                340                 345                 350

Leu Arg Arg Glu Leu Ala Ala Phe Glu Ala Asp Arg Ala Arg Glu Asp
                355                 360                 365

Gly Val Ala Leu Val Pro Cys Ser Asp Ser Asp Gly Asp Gly Ser Asp
                370                 375                 380

Glu Ala Phe Ala Ala Arg Val Ala Gln Phe Ala Gly Leu Leu Ser Tyr
385                 390                 395                 400

Asp Gly Leu Gly Lys Leu Val Tyr Leu His Ala Cys Val Thr Glu Thr
                405                 410                 415

Leu Arg Leu Tyr Pro Ala Val Pro Gln Asp Pro Lys Gly Ile Ala Glu
                420                 425                 430

Asp Asp Val Leu Pro Asp Gly Thr Lys Val Arg Ala Gly Gly Met Val
                435                 440                 445

Thr Tyr Val Pro Tyr Ser Met Gly Arg Met Glu Tyr Asn Trp Gly Pro
450                 455                 460
```

```
Asp Ala Ala Ser Phe Arg Pro Glu Arg Trp Ile Gly Asp Asp Gly Ala
465                 470                 475                 480

Phe Arg Asn Ala Ser Pro Phe Lys Phe Thr Ala Phe Gln Ala Gly Pro
                485                 490                 495

Arg Ile Cys Leu Gly Lys Asp Ser Ala Tyr Leu Gln Met Lys Met Ala
            500                 505                 510

Leu Ala Ile Leu Cys Arg Phe Phe Arg Phe Glu Leu Val Glu Gly His
        515                 520                 525

Pro Val Lys Tyr Arg Met Met Thr Ile Leu Ser Met Ala His Gly Leu
    530                 535                 540

Lys Val Arg Val Ser Arg Ala Pro Leu Ala
545                 550

<210> SEQ ID NO 30
<211> LENGTH: 1920
<212> TYPE: DNA
<213> ORGANISM: triticum aestivum

<400> SEQUENCE: 30
atgagcagcc ccatggagga agctcacctt ggcatgccgt cgacgacggc cttcttcccg      60
ctggcagggc tccacaagtt catggccgtc ttcctcgtgt tcctctcgtg gatcctggtc     120
cactggtgga gcctgaggaa gcagaagggg ccacggtcat ggccggtcat cggcgcgacg     180
ctggagcagc tgaggaacta ctaccggatg acgactggc tcgtggagta cctgtccaag     240
caccggacgg tcaccgtcga catgcccttc acctcctaca cctacatcgc gacccggtg     300 aacgtcgagc acgtgctcaa gaccaacttc aacaattacc ccaaggtgaa acaatccctcg    360 agatgtcagt caaggttcag tataatcggt actgacagtg ttacaaatgt ctgaaatctg     420
gaattgtgtg tgtaggggga ggtgtacagg tcctacatgg acgtgctgct cggcgacggc     480
atattcaacg ccgacggcga gctctggagg aagcagagga gacggcgag cttcgagttc      540 gcttccaaga acttgagaga cttcagcacg atcgtgttca gggagtactc cctgaagctg     600
tccagcatcc tgagccaggc ttgcaaggca ggcaaagttg tggacatgca ggtaactgaa     660
ctctttccct tggtcatatg aacgttgatt tcttggacaa atctcaaga ttctgacgcg      720 agcgagccaa ttcaggagct gtacatgagg atgacgctgg actcgatctg caaggtgggg    780
ttcggggtgg agatcggcac gctgtcgccg gagctgccgg agaacagctt cgcgcaggcc    840
ttcgacgccg ccaacatcat cgtgacgctg cggttcatcg acccgctgtg gcgcgtgaag    900
aaattcctgc acgtcggctc ggaggcgctg ctggagcaga gcatcaagct cgtcgacgag    960
ttcacctaca gcgtcatccg ccggcgcaag gccgagatcg tgcaagcccg gccagcggc    1020 aagcaggaga aggtgcgtac gtggtcatcg tcattcgtca agctcccgat cgctggtttg    1080
tgcagatgcc actgatcact gacacattaa ctgggcgcgc agatcaagca cgacatactg    1140
tcgcggttca tcgagctggg cgaggccggc ggcgacgacg gcggcagcct gttcggggac    1200
gacaagggcc tccgcgacgt ggtgctcaac ttcgtcatcg ccgggcggga cacgacggcc    1260
acgacgctct cctggttcac ctacatggcc atgacgcacc cggccgtggc cgagaagctc    1320
cgccgcgagc tggccgcctt cgagtccgag gcgccccgcg aggatggcgt cgctctggtc    1380
ccctgcagcg acggcgaggg ctccgacgag gccttcgccg cccgcgtggc gcagttcgcg    1440
ggactcctga gctacgacgg gctcgggaag ctggtgtacc tccacgcgtg cgtgacggag    1500 acgtccgcc tgtacccggc ggtgccgcag gaccccaagg gcatcgcgga ggacgacgtg    1560
ctcccggacg gcaccaaggt gcgcgccggc gggatggtga cgtacgtgcc ctactccatg    1620
```

```
gggcggatgg agtacaactg gggccccgac gccgccagct tccggccaga gcggtggatc    1680
ggcgacgacg gcgccttccg caacgcgtcg ccgttcaagt tcacggcgtt ccaggcgggg    1740
ccgcggatct gcctgggcaa ggactcggcg tacctgcaga tgaagatggc gctggccatc    1800
ctgtgcaggt tcttcaggtt cgagctcgtg gagggccacc ccgtcaagta ccgcatgatg    1860
accatcctct ccatggcgca cggcctcaag gtccgcgtct ccagggtgcc gctcgcctga    1920
```

<210> SEQ ID NO 31
<211> LENGTH: 551
<212> TYPE: PRT
<213> ORGANISM: triticum aestivum

<400> SEQUENCE: 31

```
Met Ser Ser Pro Met Glu Glu Ala His Leu Gly Met Pro Ser Thr Thr
1               5                   10                  15

Ala Phe Phe Pro Leu Ala Gly Leu His Lys Phe Met Ala Val Phe Leu
                20                  25                  30

Val Phe Leu Ser Trp Ile Leu Val His Trp Trp Ser Leu Arg Lys Gln
            35                  40                  45

Lys Gly Pro Arg Ser Trp Pro Val Ile Gly Ala Thr Leu Glu Gln Leu
        50                  55                  60

Arg Asn Tyr Tyr Arg Met His Asp Trp Leu Val Glu Tyr Leu Ser Lys
65                  70                  75                  80

His Arg Thr Val Thr Val Asp Met Pro Phe Thr Ser Tyr Thr Tyr Ile
                85                  90                  95

Ala Asp Pro Val Asn Val Glu His Val Leu Lys Thr Asn Phe Asn Asn
                100                 105                 110

Tyr Pro Lys Gly Glu Val Tyr Arg Ser Tyr Met Asp Val Leu Leu Gly
            115                 120                 125

Asp Gly Ile Phe Asn Ala Asp Gly Glu Leu Trp Arg Lys Gln Arg Lys
        130                 135                 140

Thr Ala Ser Phe Glu Phe Ala Ser Lys Asn Leu Arg Asp Phe Ser Thr
145                 150                 155                 160

Ile Val Phe Arg Glu Tyr Ser Leu Lys Leu Ser Ser Ile Leu Ser Gln
                165                 170                 175

Ala Cys Lys Ala Gly Lys Val Val Asp Met Gln Glu Leu Tyr Met Arg
            180                 185                 190

Met Thr Leu Asp Ser Ile Cys Lys Val Gly Phe Gly Val Glu Ile Gly
        195                 200                 205

Thr Leu Ser Pro Glu Leu Pro Glu Asn Ser Phe Ala Gln Ala Phe Asp
    210                 215                 220

Ala Ala Asn Ile Ile Val Thr Leu Arg Phe Ile Asp Pro Leu Trp Arg
225                 230                 235                 240

Val Lys Lys Phe Leu His Val Gly Ser Glu Ala Leu Leu Glu Gln Ser
                245                 250                 255

Ile Lys Leu Val Asp Glu Phe Thr Tyr Ser Val Ile Arg Arg Arg Lys
            260                 265                 270

Ala Glu Ile Val Gln Ala Arg Ala Ser Gly Lys Gln Glu Lys Ile Lys
        275                 280                 285

His Asp Ile Leu Ser Arg Phe Ile Glu Leu Gly Glu Ala Gly Gly Asp
    290                 295                 300

Asp Gly Gly Ser Leu Phe Gly Asp Asp Lys Gly Leu Arg Asp Val Val
305                 310                 315                 320
```

```
Leu Asn Phe Val Ile Ala Gly Arg Asp Thr Thr Ala Thr Thr Leu Ser
            325                 330                 335

Trp Phe Thr Tyr Met Ala Met Thr His Pro Ala Val Ala Glu Lys Leu
            340                 345                 350

Arg Arg Glu Leu Ala Ala Phe Glu Ser Glu Arg Ala Arg Glu Asp Gly
            355                 360                 365

Val Ala Leu Val Pro Cys Ser Asp Gly Glu Gly Ser Asp Glu Ala Phe
            370                 375                 380

Ala Ala Arg Val Ala Gln Phe Ala Gly Leu Leu Ser Tyr Asp Gly Leu
385                 390                 395                 400

Gly Lys Leu Val Tyr Leu His Ala Cys Val Thr Glu Thr Leu Arg Leu
            405                 410                 415

Tyr Pro Ala Val Pro Gln Asp Pro Lys Gly Ile Ala Glu Asp Asp Val
            420                 425                 430

Leu Pro Asp Gly Thr Lys Val Arg Ala Gly Gly Met Val Thr Tyr Val
            435                 440                 445

Pro Tyr Ser Met Gly Arg Met Glu Tyr Asn Trp Gly Pro Asp Ala Ala
            450                 455                 460

Ser Phe Arg Pro Glu Arg Trp Ile Gly Asp Asp Gly Ala Phe Arg Asn
465                 470                 475                 480

Ala Ser Pro Phe Lys Phe Thr Ala Phe Gln Ala Gly Pro Arg Ile Cys
            485                 490                 495

Leu Gly Lys Asp Ser Ala Tyr Leu Gln Met Lys Met Ala Leu Ala Ile
            500                 505                 510

Leu Cys Arg Phe Phe Arg Phe Glu Leu Val Glu Gly His Pro Val Lys
            515                 520                 525

Tyr Arg Met Met Thr Ile Leu Ser Met Ala His Gly Leu Lys Val Arg
            530                 535                 540

Val Ser Arg Val Pro Leu Ala
545                 550

<210> SEQ ID NO 32
<211> LENGTH: 1920
<212> TYPE: DNA
<213> ORGANISM: triticum aestivum

<400> SEQUENCE: 32
atgagcagcc ccatggagga agctcacggc ggcatgccgt cgacgacggc cttcttcccg      60
ctggcagggc tccacaagtt catggccatc ttcctcgtgt cctctcgtg gatcttggtc     120 cactggtgga gcctgaggaa gcagaagggg ccgaggtcat ggccggtcat ggcgcgacg     180 ctggagcagc tgaggaacta ctaccggatg cacgactggc tcgtggagta cctgtccaag     240
caccggacgg tgaccgtcga catgcccttc acctcctaca cctacatcgc cgacccggtg     300
aacgtcgagc atgtgctcaa gaccaacttc aacaattacc ccaaggtgaa acaatcctcg     360
agatgtcagt aaaggttcag tataatcggt actgacagtg ttacaaatgt ctgaaatctg     420
aaattgtatg tgtaggggga ggtgtacagg tcctacatgg acgtgctgct cggcgacggc     480
atattcaacg ccgacggcga gctctggagg aagcagagga gacggcgag cttcgagttc     540 gcttccaaga acttgagaga cttcagcacg atcgtgttca gggagtactc cctgaagctg     600
tccagcatac tgagccaggc ttgcaaggcc ggcaaagttg tggacatgca ggtaactgaa     660
ctcattccct tggtcatctg aacgttgatt tcttggacaa aatttcaaga ttctgacgcg     720
agcgagcgaa ttcaggagct gtatatgagg atgacgctgg actcgatctg caaagtgggg     780
```

```
ttcggagtcg agatcggcac gctgtcgccg gagctgccgg agaacagctt cgcgcaggcg    840
ttcgacgccg ccaacatcat cgtgacgctg cggttcatcg acccgctgtg gcgcgtgaag    900
aagttcctgc acgtcggctc ggaggcgctg ctggagcaga gcatcaagct cgtcgacgag    960
ttcacctaca cgtcatccg ccggcgcaag gccgagatcg tgcaggcccg ggccagcggc   1020
aagcaggaga aggtgcgtgc gtggtcatcg tcattcgtca agctcccggt cgctggtttg   1080
tgtagatgcc atgatcact gacacactaa ctgggcgcgc agatcaagca cgacatactg   1140
tcgcggttca tcgagctggg cgaggccggc ggcgacgacg gcggcagtct gttcggggac   1200
gacaagggcc tccgcgacgt ggtgctcaac ttcgtgatcg ccgggcggga caccacggcc   1260
acgacgctgt cctggttcac ctacatggcc atgacgcacc cggacgtggc cgagaagctc   1320
cgccgcgagc tggccgcctt cgaggcgag cgcgcccgcg aggatggcgt cgctctggtc   1380
ccctgcggcg acgcgagggg ctccgacgag gccttcgctg cccgcgtggc gcagttcgcg   1440
gggttcctga gctacgacgg cctcgggaag ctggtgtacc tccacgcgtg cgtgacggag   1500
acgctgcgcc tgtacccggc ggtgccgcag gaccccaagg gcatcgcgga ggacgacgtg   1560
ctccccggacg gcaccaaggt gcgcgccggc gggatggtga cgtacgtgcc ctactccatg   1620
gggcggatgg agtacaactg gggcccccgac gccgccagct ccggccggga gcggtggatc   1680
ggcgacgacg gcgccttccg caacgcgtcg ccgttcaagt tcacggcgtt ccaggcgggg   1740
ccgcggattt gcctcggcaa ggactcggcg tacctgcaga tgaagatggc gctggcaatc   1800
ctgtgcaggt tcttcaggtt cgagctcgtg gagggccacc ccgtcaagta ccgcatgatg   1860
accatcctct ccatggcgca cggcctcaag gtccgcgtct ccagggcgcc gctcgcctga   1920
```

<210> SEQ ID NO 33
<211> LENGTH: 551
<212> TYPE: PRT
<213> ORGANISM: triticum aestivum

<400> SEQUENCE: 33

Met Ser Ser Pro Met Glu Glu Ala His Gly Gly Met Pro Ser Thr Thr
1               5                   10                  15

Ala Phe Phe Pro Leu Ala Gly Leu His Lys Phe Met Ala Ile Phe Leu
            20                  25                  30

Val Phe Leu Ser Trp Ile Leu Val His Trp Ser Leu Arg Lys Gln
        35                  40                  45

Lys Gly Pro Arg Ser Trp Pro Val Ile Gly Ala Thr Leu Glu Gln Leu
    50                  55                  60

Arg Asn Tyr Tyr Arg Met His Asp Trp Leu Val Glu Tyr Leu Ser Lys
65                  70                  75                  80

His Arg Thr Val Thr Val Asp Met Pro Phe Thr Ser Tyr Thr Tyr Ile
                85                  90                  95

Ala Asp Pro Val Asn Val Glu His Val Leu Lys Thr Asn Phe Asn Asn
            100                 105                 110

Tyr Pro Lys Gly Glu Val Tyr Arg Ser Tyr Met Asp Val Leu Leu Gly
        115                 120                 125

Asp Gly Ile Phe Asn Ala Asp Gly Glu Leu Trp Arg Lys Gln Arg Lys
    130                 135                 140

Thr Ala Ser Phe Glu Phe Ala Ser Lys Asn Leu Arg Asp Phe Ser Thr
145                 150                 155                 160

Ile Val Phe Arg Glu Tyr Ser Leu Lys Leu Ser Ser Ile Leu Ser Gln
                165                 170                 175

Ala Cys Lys Ala Gly Lys Val Val Asp Met Gln Glu Leu Tyr Met Arg
            180                 185                 190

Met Thr Leu Asp Ser Ile Cys Lys Val Gly Phe Gly Val Glu Ile Gly
            195                 200                 205

Thr Leu Ser Pro Glu Leu Pro Glu Asn Ser Phe Ala Gln Ala Phe Asp
            210                 215                 220

Ala Ala Asn Ile Ile Val Thr Leu Arg Phe Ile Asp Pro Leu Trp Arg
225                 230                 235                 240

Val Lys Lys Phe Leu His Val Gly Ser Glu Ala Leu Leu Glu Gln Ser
            245                 250                 255

Ile Lys Leu Val Asp Glu Phe Thr Tyr Ser Val Ile Arg Arg Arg Lys
            260                 265                 270

Ala Glu Ile Val Gln Ala Arg Ala Ser Gly Lys Gln Glu Lys Ile Lys
            275                 280                 285

His Asp Ile Leu Ser Arg Phe Ile Glu Leu Gly Glu Ala Gly Gly Asp
            290                 295                 300

Asp Gly Gly Ser Leu Phe Gly Asp Lys Gly Leu Arg Asp Val Val
305                 310                 315                 320

Leu Asn Phe Val Ile Ala Gly Arg Asp Thr Thr Ala Thr Thr Leu Ser
            325                 330                 335

Trp Phe Thr Tyr Met Ala Met Thr His Pro Asp Val Ala Glu Lys Leu
            340                 345                 350

Arg Arg Glu Leu Ala Ala Phe Glu Ala Glu Arg Ala Arg Glu Asp Gly
            355                 360                 365

Val Ala Leu Val Pro Cys Gly Asp Gly Glu Ser Asp Glu Ala Phe
370                 375                 380

Ala Ala Arg Val Ala Gln Phe Ala Gly Phe Leu Ser Tyr Asp Gly Leu
385                 390                 395                 400

Gly Lys Leu Val Tyr Leu His Ala Cys Val Thr Glu Thr Leu Arg Leu
            405                 410                 415

Tyr Pro Ala Val Pro Gln Asp Pro Lys Gly Ile Ala Glu Asp Val
            420                 425                 430

Leu Pro Asp Gly Thr Lys Val Arg Ala Gly Gly Met Val Thr Tyr Val
            435                 440                 445

Pro Tyr Ser Met Gly Arg Met Glu Tyr Asn Trp Gly Pro Asp Ala Ala
            450                 455                 460

Ser Phe Arg Pro Glu Arg Trp Ile Gly Asp Asp Gly Ala Phe Arg Asn
465                 470                 475                 480

Ala Ser Pro Phe Lys Phe Thr Ala Phe Gln Ala Gly Pro Arg Ile Cys
            485                 490                 495

Leu Gly Lys Asp Ser Ala Tyr Leu Gln Met Lys Met Ala Leu Ala Ile
            500                 505                 510

Leu Cys Arg Phe Phe Arg Phe Glu Leu Val Glu Gly His Pro Val Lys
            515                 520                 525

Tyr Arg Met Met Thr Ile Leu Ser Met Ala His Gly Leu Lys Val Arg
            530                 535                 540

Val Ser Arg Ala Pro Leu Ala
545                 550

<210> SEQ ID NO 34
<211> LENGTH: 1483
<212> TYPE: DNA
<213> ORGANISM: triticum aestivum

<400> SEQUENCE: 34

```
atggaagaga agaagccgcg gcggcaggga gccgcaggac gcgatggcat cgtgcagtac      60
ccgcacctct tcatcgcggc cctggcgctg gccctggtcc tcatggaccc cttccacctc     120
ggcccgctgg ccgggatcga ctaccggccg gtgaagcacg agctggcgcc gtacagggag     180
gtcatgcagc gctggccgag ggacaacggc agccgcctca ggctcggcag gctcgagttc     240
gtcaacgagg tgttcgggcc agagtccatc gagttcgacc gccagggccg cgggccctac     300
gccgggctcg ccgacggccg cgtcgtgcgg tggatggggg acaaggccgg gtgggagacg     360
ttcgccgtca tgaatcctga ctggtattgg cttactgcag aaaaaccata gcttacctgt     420
gtgtgtgcaa actaaaatag tttttcgga aaaaaaagg tcggagaaag tttgtgctaa     480
cggagtggag tcgacgacga agaagcagca cgggaaggag aagtggtgcg gccggcctct     540
cgggctgagg ttccacaggg agaccggcga gctcttcatc gccgacgcgt actatgggct     600
catggccgtt ggcgaaagcg gcggcgtggc gacctccctg gcgagggagg ccggcgggga     660
cccggtccac ttcgccaacg acctcgacat ccacatgaac ggctcgatat tcttcaccga     720
cacgagcacg agatacagca gaaagtgagc ggagtactgc tgccgatctc ctttttctgt     780
tcttgagatt tgtgtttgac aaatgactga tcatgcaggg accatttgaa cattttgctg     840
gaaggagaag gcacggggag gctgctgaga tatgaccgag aaaccggtgc cgttcatgtc     900
gtgctcaacg gctggtcttc ccaaacggc gtgcagatct cacaggacca gcaatttctc     960
ctcttctccg agacaacaaa ctgcaggtga gataaactca ggttttcagt atgatccggc    1020
tcgagagatc caggaactga tgacgccttt attaatcggc tcatgcatgc acactaggat    1080
catgaggtac tggctggaag gtccaagagc gggccaggtg gaggtgttcg cgaacctgcc    1140
ggggttcccc gacaacgtgc gcttgaacag caagggcag ttctgggtgg cgatcgactg    1200
ctgccggacg ccgacgcagg aggtgttcgc gcggtggccg tggctgcgga ccgcctactt    1260
caagatcccg gtgtcgatga agacgctggg gaagatggtg agcatgaaga tgtacacgct    1320
tctcgcgctc ctcgacggcg aggggaacgt ggtcgaggta ctcgaggacc ggggcggcga    1380
ggtgatgaag ctggtgagcg aggtgaggga ggtggaccgg aggctgtgga tcgggaccgt    1440
tgcgcacaac cacatcgcca cgatccctta tccgttggac tag                      1483
```

<210> SEQ ID NO 35
<211> LENGTH: 413
<212> TYPE: PRT
<213> ORGANISM: triticum aestivum

<400> SEQUENCE: 35

```
Met Glu Glu Lys Lys Pro Arg Arg Gln Gly Ala Ala Gly Arg Asp Gly
1               5                   10                  15

Ile Val Gln Tyr Pro His Leu Phe Ile Ala Ala Leu Ala Leu Ala Leu
            20                  25                  30

Val Leu Met Asp Pro Phe His Leu Gly Pro Leu Ala Gly Ile Asp Tyr
        35                  40                  45

Arg Pro Val Lys His Glu Leu Ala Pro Tyr Arg Glu Val Met Gln Arg
    50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Arg Gln Gly
                85                  90                  95

Arg Gly Pro Tyr Ala Gly Leu Ala Asp Gly Arg Val Val Arg Trp Met
            100                 105                 110
```

Gly Asp Lys Ala Gly Trp Glu Thr Phe Ala Val Met Asn Pro Asp Trp
            115                 120                 125

Ser Glu Lys Val Cys Ala Asn Gly Val Glu Ser Thr Thr Lys Lys Gln
        130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Ser Gly Val Ala Thr Ser Leu Ala Arg Glu Ala
            180                 185                 190

Gly Gly Asp Pro Val His Phe Ala Asn Asp Leu Asp Ile His Met Asn
            195                 200                 205

Gly Ser Ile Phe Phe Thr Asp Thr Ser Thr Arg Tyr Ser Arg Lys Asp
210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Leu Asn Gly Leu Val
                245                 250                 255

Phe Pro Asn Gly Val Gln Ile Ser Gln Asp Gln Gln Phe Leu Leu Phe
            260                 265                 270

Ser Glu Thr Thr Asn Cys Arg Ile Met Arg Tyr Trp Leu Glu Gly Pro
        275                 280                 285

Arg Ala Gly Gln Val Glu Val Phe Ala Asn Leu Pro Gly Phe Pro Asp
290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                325                 330                 335

Thr Ala Tyr Phe Lys Ile Pro Val Ser Met Lys Thr Leu Gly Lys Met
            340                 345                 350

Val Ser Met Lys Met Tyr Thr Leu Leu Ala Leu Leu Asp Gly Glu Gly
        355                 360                 365

Asn Val Val Glu Val Leu Glu Asp Arg Gly Gly Glu Val Met Lys Leu
370                 375                 380

Val Ser Glu Val Arg Glu Val Asp Arg Arg Leu Trp Ile Gly Thr Val
385                 390                 395                 400

Ala His Asn His Ile Ala Thr Ile Pro Tyr Pro Leu Asp
                405                 410

<210> SEQ ID NO 36
<211> LENGTH: 1481
<212> TYPE: DNA
<213> ORGANISM: triticum aestivum

<400> SEQUENCE: 36
atggaagaga agaagccgcg gcggcaggga gccgcagtac gcgatggcat cgtgcagtac    60
ccgcacctct tcatcgcggc cctggcgctg ccctggtcg tcatggaccc cttccacctc   120
ggcccgctgg ctgggatcga ctaccggccg gtgaagcacg agctggcgcc atacagggag   180
gtcatgcagc gctggccgag ggacaacggc agccgcctca ggctcggcag gctcgagttc   240
gtcaacgagg tgttcgggcc ggagtccatc gagttcgaca gccagggccg cgggccctac   300
gccgggctcg ccgacggccg cgtcgtgcgg tggatggggg acaagaccgg gtgggagacg   360
ttcgccgtca tgaatcctga ctggtaattg gcttactgca gataaatcca tagcttacct   420

```
gtgtgtttgc aaactaaaat gatttcttgg gaaaaaaaaa ggtcggagaa agtttgtgct      480
aacggagtgg agtcaacgac gaagaagcag cacgggaagg agaagtggtg cggccggcct      540
ctcgggctga ggttccacag ggagaccggc gagctcttca tcgccgacgc gtactatggg      600
ctcatggccg tcggcgaaag cggcggcgtg gcgacctccc tggcagggga ggtcggcggg      660
gacccggtcc acttcgccaa cgacctcgac atccacatga acggctcgat attcttcacc      720
gacacgagca cgagatacag cagaaagtga gcggagtact gtcgctgatc tccatttttg      780
ttcttgagat gttgtgtttg agtgtctgac accatgactg atcatgcagg gatcatttga      840 acatttttgct agaaggagaa ggcacgggga ggctgctgag atatgaccga gaaaccggtg      900
ccgttcatgt cgtgctcaac gggctggtct cccaaacgg cgtgcagatt tcacaggacc       960 agcaattttct cctcttctcc gagacaacca actgcaggtg agataaactc aggttttcag     1020
tatgatccgg ctcgagagat ccaggaactg atgacggatc atgcatgcac gctaggatca     1080
tgaggtactg gctggaaggt ccaagagcgg gccaggtgga ggtgttcgcg aacctgccgg     1140
ggttccccga caacgtgcgc ctgaacagca aggggcagtt ctgggtggcg atcgactgct     1200
gccggacgcc gacgcaggag gtgttcgcga ggtggccgtg gctgcggacc gcctacttca     1260
agatcccggt gtcgatgaag acgctgggga agatggtgag catgaagatg tacacgcttc     1320
tcgcgctcct cgacggcgag gggaacgtgg tggaggtgct cgaggaccgg ggcggcgagg     1380
tgatgaagct ggtgagcgag gtgagggagg tggaccggag gctgtggatc gggaccgttg     1440
cgcacaacca catcgccacg atcccttacc cgctggacta g                          1481
```

<210> SEQ ID NO 37
<211> LENGTH: 413
<212> TYPE: PRT
<213> ORGANISM: triticum aestivum

<400> SEQUENCE: 37

```
Met Glu Glu Lys Lys Pro Arg Arg Gln Gly Ala Ala Val Arg Asp Gly
1               5                   10                  15

Ile Val Gln Tyr Pro His Leu Phe Ile Ala Ala Leu Ala Leu Ala Leu
            20                  25                  30

Val Val Met Asp Pro Phe His Leu Gly Pro Leu Ala Gly Ile Asp Tyr
        35                  40                  45

Arg Pro Val Lys His Glu Leu Ala Pro Tyr Arg Glu Val Met Gln Arg
    50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Ser Gln Gly
                85                  90                  95

Arg Gly Pro Tyr Ala Gly Leu Ala Asp Gly Arg Val Val Arg Trp Met
            100                 105                 110

Gly Asp Lys Thr Gly Trp Glu Thr Phe Ala Val Met Asn Pro Asp Trp
        115                 120                 125

Ser Glu Lys Val Cys Ala Asn Gly Val Glu Ser Thr Thr Lys Lys Gln
    130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Ser Gly Gly Val Ala Thr Ser Leu Ala Arg Glu Val
```

```
            180              185              190
Gly Gly Asp Pro Val His Phe Ala Asn Asp Leu Asp Ile His Met Asn
            195              200              205
Gly Ser Ile Phe Phe Thr Asp Thr Ser Thr Arg Tyr Ser Arg Lys Asp
        210              215              220
His Leu Asn Ile Leu Leu Glu Gly Glu Gly Thr Gly Arg Leu Leu Arg
225              230              235              240
Tyr Asp Arg Glu Thr Gly Ala Val His Val Val Leu Asn Gly Leu Val
                245              250              255
Phe Pro Asn Gly Val Gln Ile Ser Gln Asp Gln Gln Phe Leu Leu Phe
            260              265              270
Ser Glu Thr Thr Asn Cys Arg Ile Met Arg Tyr Trp Leu Glu Gly Pro
        275              280              285
Arg Ala Gly Gln Val Glu Val Phe Ala Asn Leu Pro Gly Phe Pro Asp
        290              295              300
Asn Val Arg Leu Asn Ser Lys Gly Gln Phe Trp Val Ala Ile Asp Cys
305              310              315              320
Cys Arg Thr Pro Thr Gln Glu Val Phe Ala Arg Trp Pro Trp Leu Arg
                325              330              335
Thr Ala Tyr Phe Lys Ile Pro Val Ser Met Lys Thr Leu Gly Lys Met
                340              345              350
Val Ser Met Lys Met Tyr Thr Leu Leu Ala Leu Leu Asp Gly Glu Gly
            355              360              365
Asn Val Val Glu Val Leu Glu Asp Arg Gly Gly Glu Val Met Lys Leu
        370              375              380
Val Ser Glu Val Arg Glu Val Asp Arg Arg Leu Trp Ile Gly Thr Val
385              390              395              400
Ala His Asn His Ile Ala Thr Ile Pro Tyr Pro Leu Asp
                405              410

<210> SEQ ID NO 38
<211> LENGTH: 1471
<212> TYPE: DNA
<213> ORGANISM: triticum aestivum

<400> SEQUENCE: 38
atggaagaga agaaaccgcg gcggcaggga gccgcagtac gcgatggcat cgtgcagtac      60
ccgcacctct tcatcgcggc cctggcgctg gccctggtcc tcatggaccc gttccacctc     120
ggcccgctgg ccgggatcga ctaccgaccg gtgaagcacg agctggcgcc gtacagggag     180
gtcatgcagc gctggccgag ggacaacggc agccgcctca ggctcggcag gctcgagttc     240
gtcaacgagg tgttcgggcc ggagtccatc gagttcgacc gccagggccg cgggccttac     300
gccgggctcg ccgacggccg cgtcgtgcgg tggatggggg acaaggccgg gtgggagacg     360
ttcgccgtca tgaatcctga ctggtactgg cttactgcag aaaaacccat agcttacctg     420
tgtgtgtgca gactaaaata gtttctttca taaaaaaaag gtcggagaaa gtttgtgcta     480
acggagtgga gtcgacgacg aagaagcagc acgggaagga gaagtggtgc ggccggcctc     540
tcggcctgag gttccacagg gagaccggcg agctcttcat cgccgacgcg tactatgggc     600
tcatggccgt cggcgaaagg ggcggcgtgg cgacctccct ggcgagggag ccggcggggg     660
acccggtcca cttcgccaac gaccttgaca tccacatgaa cggctcgata ttcttcaccg     720
acacgagcac gagatacagc agaaagtgag cggagtactg ctgccgatct ccttttttctg     780
ttcttgagat ttgtgtttga caaatgactg atcatgcagg gaccatttga acatttttgct     840
```

```
ggaaggagaa ggcacgggga ggctgctgag atatgaccga gaaaccggtg ccgttcatgt    900
cgtgctcaac gggctggtct tcccaaacgg cgtgcagata tcacaggacc agcaatttct    960
cctcttctcc gagacaacaa actgcaggtg agataaactc aggttttcag tatgatccgg   1020
ctcgagagat ccaggaactg atgacggctc atgcatgcac actaggatca tgaggtactg   1080
gctggaaggt ccaagagcgg gccaggtgga ggtgttcgcg aacctgccgg ggttccccga   1140
caatgtgcgc ctgaacagca aggggcagtt ctgggtggcc atcgactgct gccgtacgcc   1200
gacgcaggag gtgttcgcgc ggtggccgtg gctgcggacc gcctacttca agatcccggt   1260
gtcgatgaag acgctgggga agatggtgag catgaagatg tacacgcttc tcgcgctcct   1320
cgacggcgag gggaacgtcg tggaggtgct cgaggaccgg ggcggcgagg tgatgaagct   1380
ggtgagcgag gtgagggagg tggaccggag gctgtggatc gggaccgttg cgcacaacca   1440
catcgccacg atcccttacc cgctggacta g                                 1471
```

<210> SEQ ID NO 39
<211> LENGTH: 413
<212> TYPE: PRT
<213> ORGANISM: triticum aestivum

<400> SEQUENCE: 39

```
Met Glu Glu Lys Lys Pro Arg Arg Gln Gly Ala Ala Val Arg Asp Gly
1               5                   10                  15

Ile Val Gln Tyr Pro His Leu Phe Ile Ala Ala Leu Ala Leu Ala Leu
            20                  25                  30

Val Leu Met Asp Pro Phe His Leu Gly Pro Leu Ala Gly Ile Asp Tyr
        35                  40                  45

Arg Pro Val Lys His Glu Leu Ala Pro Tyr Arg Glu Val Met Gln Arg
    50                  55                  60

Trp Pro Arg Asp Asn Gly Ser Arg Leu Arg Leu Gly Arg Leu Glu Phe
65                  70                  75                  80

Val Asn Glu Val Phe Gly Pro Glu Ser Ile Glu Phe Asp Arg Gln Gly
                85                  90                  95

Arg Gly Pro Tyr Ala Gly Leu Ala Asp Gly Arg Val Val Arg Trp Met
            100                 105                 110

Gly Asp Lys Ala Gly Trp Glu Thr Phe Ala Val Met Asn Pro Asp Trp
        115                 120                 125

Ser Glu Lys Val Cys Ala Asn Gly Val Glu Ser Thr Thr Lys Lys Gln
    130                 135                 140

His Gly Lys Glu Lys Trp Cys Gly Arg Pro Leu Gly Leu Arg Phe His
145                 150                 155                 160

Arg Glu Thr Gly Glu Leu Phe Ile Ala Asp Ala Tyr Tyr Gly Leu Met
                165                 170                 175

Ala Val Gly Glu Arg Gly Gly Val Ala Thr Ser Leu Ala Arg Glu Ala
            180                 185                 190

Gly Gly Asp Pro Val His Phe Ala Asn Asp Leu Asp Ile His Met Asn
        195                 200                 205

Gly Ser Ile Phe Phe Thr Asp Thr Ser Thr Arg Tyr Ser Arg Lys Asp
    210                 215                 220

His Leu Asn Ile Leu Leu Glu Gly Glu Gly Thr Gly Arg Leu Leu Arg
225                 230                 235                 240

Tyr Asp Arg Glu Thr Gly Ala Val His Val Val Leu Asn Gly Leu Val
                245                 250                 255
```

```
Phe Pro Asn Gly Val Gln Ile Ser Gln Asp Gln Gln Phe Leu Leu Phe
            260                 265                 270

Ser Glu Thr Thr Asn Cys Arg Ile Met Arg Tyr Trp Leu Glu Gly Pro
        275                 280                 285

Arg Ala Gly Gln Val Glu Val Phe Ala Asn Leu Pro Gly Phe Pro Asp
    290                 295                 300

Asn Val Arg Leu Asn Ser Lys Gly Gln Phe Trp Val Ala Ile Asp Cys
305                 310                 315                 320

Cys Arg Thr Pro Thr Gln Glu Val Phe Ala Arg Trp Pro Trp Leu Arg
                325                 330                 335

Thr Ala Tyr Phe Lys Ile Pro Val Ser Met Lys Thr Leu Gly Lys Met
            340                 345                 350

Val Ser Met Lys Met Tyr Thr Leu Leu Ala Leu Leu Asp Gly Glu Gly
        355                 360                 365

Asn Val Val Glu Val Leu Glu Asp Arg Gly Gly Glu Val Met Lys Leu
    370                 375                 380

Val Ser Glu Val Arg Val Asp Arg Arg Leu Trp Ile Gly Thr Val
385                 390                 395                 400

Ala His Asn His Ile Ala Thr Ile Pro Tyr Pro Leu Asp
            405                 410
```

<210> SEQ ID NO 40
<211> LENGTH: 20
<212> TYPE: DNA
<213> ORGANISM: Artificial Sequence
<220> FEATURE:
<223> OTHER INFORMATION: synthesized

<400> SEQUENCE: 40
ggaggtacac caactacctg                                              20

<210> SEQ ID NO 41
<211> LENGTH: 568
<212> TYPE: PRT
<213> ORGANISM: Thinopyrum ponticum

<400> SEQUENCE: 41

```
Met Arg Glu Ile Ala Thr Gln Arg Cys Gly Asn Arg Ser Met Ala Leu
1               5                   10                  15

Ser Ala Pro Pro Ser Gln Glu Gln Pro Ser Gly Lys Gln Phe Gly Tyr
            20                  25                  30

Gln Leu Ala Ala Ala Val Arg Ser Ile Asn Trp Thr Tyr Gly Ile Phe
        35                  40                  45

Trp Ser Ile Ser Ala Ser Pro Arg Pro Gly His Ser Ser Val Leu Ala
50                  55                  60

Trp Lys Asp Gly Phe Tyr Asn Gly Glu Ile Lys Thr Arg Lys Ile Thr
65                  70                  75                  80

Gly Ser Thr Thr Thr Glu Leu Thr Ala Asp Glu Arg Val Met His Arg
                85                  90                  95

Ser Lys Gln Leu Arg Glu Leu Tyr Glu Ser Leu Leu Pro Gly Asn Ser
            100                 105                 110

Asn Asn Arg Ala Arg Arg Pro Thr Ala Ser Leu Ser Pro Glu Asp Leu
        115                 120                 125

Gly Asp Gly Glu Trp Tyr Tyr Thr Ile Ser Met Thr Tyr Thr Phe His
    130                 135                 140

Pro Asn Gln Gly Leu Pro Gly Lys Ser Phe Ala Ser Asn Gln His Val
145                 150                 155                 160
```

```
Trp Leu Tyr Asn Ala Gln Tyr Ala Asn Thr Arg Val Phe Pro Arg Ala
                165                 170                 175

Leu Leu Ala Lys Thr Ile Val Cys Ile Pro Phe Met Gly Gly Val Leu
            180                 185                 190

Glu Leu Gly Thr Ser Asp Gln Val Leu Glu Asp Pro Ser Met Val Lys
        195                 200                 205

Arg Ile Ser Thr Ser Phe Trp Glu Leu His Leu Pro Ser Ser Leu Glu
    210                 215                 220

Ser Lys Asp Pro Ser Ser Thr Ser Ala Asn Asp Thr Arg Glu Ala
225                 230                 235                 240

Thr Asp Ile Ile Leu Phe Glu Asp Phe Asp His Asn Asp Thr Val Glu
                245                 250                 255

Gly Val Ile Ser Glu Gln Arg Glu Val Gln Cys Pro Ser Asn Val Asn
            260                 265                 270

Leu Glu Arg Leu Thr Lys Gln Met Asp Glu Phe His Ser Leu Leu Gly
        275                 280                 285

Gly Leu Asp Val His Pro Leu Glu Asp Arg Trp Ile Met Asp Glu Pro
    290                 295                 300

Phe Glu Phe Thr Phe Ser Pro Glu Val Ala Pro Ala Met Asp Met Pro
305                 310                 315                 320

Ser Thr Asp Asp Val Ile Val Thr Leu Ser Arg Ser Glu Gly Ser Arg
                325                 330                 335

Pro Ser Cys Phe Thr Ala Trp Lys Gly Ser Ser Glu Ser Lys Tyr Val
            340                 345                 350

Ala Gly Gln Val Val Gly Glu Ser Gln Lys Leu Leu Asn Lys Val Val
        355                 360                 365

Ala Gly Gly Ala Trp Ala Ser Asn Tyr Gly Gly Arg Thr Met Val Arg
    370                 375                 380

Ala Gln Gly Ile Asn Ser Asn Thr His Val Met Thr Glu Arg Arg Arg
385                 390                 395                 400

Arg Glu Lys Leu Asn Glu Met Phe Leu Val Leu Lys Ser Leu Val Pro
                405                 410                 415

Ser Ile His Lys Val Asp Lys Ala Ser Ile Leu Thr Glu Thr Ile Gly
            420                 425                 430

Tyr Leu Arg Glu Leu Lys Gln Arg Val Asp Gln Leu Glu Ser Ser Arg
        435                 440                 445

Ser Pro Ser His Pro Lys Glu Thr Thr Gly Pro Ser Arg Ser His Val
    450                 455                 460

Val Gly Ala Arg Lys Lys Ile Val Ser Ala Gly Ser Lys Arg Lys Ala
465                 470                 475                 480

Pro Gly Leu Glu Ser Pro Ser Asn Val Val Asn Val Thr Met Leu Asp
                485                 490                 495

Lys Val Leu Leu Glu Val Gln Cys Pro Trp Lys Glu Leu Leu Met
            500                 505                 510

Thr Gln Val Phe Asp Ala Ile Lys Ser Leu Cys Leu Asp Val Val Ser
        515                 520                 525

Val Gln Ala Ser Thr Ser Gly Gly Arg Leu Asp Leu Lys Ile Arg Ala
    530                 535                 540

Asn Gln Gln Leu Ala Val Gly Ser Ala Met Val Ala Pro Gly Ala Ile
545                 550                 555                 560

Thr Glu Thr Leu Gln Lys Ala Ile
                565
```

<210> SEQ ID NO 42
<211> LENGTH: 573
<212> TYPE: PRT
<213> ORGANISM: Thinopyrum ponticum

<400> SEQUENCE: 42

```
Met Arg Glu Ile Ala Thr Gln Arg Cys Gly Asn Arg Ser Met Ala Leu
1               5                   10                  15

Ser Ala Pro Pro Ser Gln Glu Gln Pro Ser Gly Lys Gln Phe Gly Tyr
            20                  25                  30

Gln Leu Ala Ala Ala Val Arg Ser Ile Asn Trp Thr Tyr Gly Ile Phe
        35                  40                  45

Trp Ser Ile Ser Ala Ser Pro Arg Pro Gly His Ser Ser Val Leu Ala
    50                  55                  60

Trp Lys Asp Gly Phe Tyr Asn Gly Glu Ile Lys Thr Arg Lys Ile Thr
65                  70                  75                  80

Gly Ser Thr Thr Thr Glu Leu Thr Ala Asp Glu Arg Val Met His Arg
                85                  90                  95

Ser Lys Gln Leu Arg Glu Leu Tyr Glu Ser Leu Leu Pro Gly Asn Ser
            100                 105                 110

Asn Asn Arg Ala Arg Arg Pro Thr Ala Ser Leu Ser Pro Glu Asp Leu
        115                 120                 125

Gly Asp Gly Glu Trp Tyr Tyr Thr Ile Ser Met Thr Tyr Thr Phe His
    130                 135                 140

Pro Asn Gln Gly Leu Pro Gly Lys Ser Phe Ala Ser Asn Gln His Val
145                 150                 155                 160

Trp Leu Tyr Asn Ala Gln Tyr Ala Asn Thr Arg Val Phe Pro Arg Ala
                165                 170                 175

Leu Leu Ala Lys Thr Ala Ser Ile Gln Thr Ile Val Cys Ile Pro Phe
            180                 185                 190

Met Gly Gly Val Leu Glu Leu Gly Thr Ser Asp Gln Val Leu Glu Asp
        195                 200                 205

Pro Ser Met Val Lys Arg Ile Asn Thr Ser Phe Trp Glu Leu His Leu
    210                 215                 220

Pro Ser Ser Leu Glu Ser Lys Asp Pro Ser Ser Thr Ser Ala Asn
225                 230                 235                 240

Asp Thr Arg Glu Ala Thr Asp Ile Ile Leu Phe Glu Asp Phe Asp His
                245                 250                 255

Asn Asp Thr Val Glu Gly Val Ile Ser Glu Gln Arg Glu Val Gln Cys
            260                 265                 270

Thr Ser Asn Val Asn Leu Glu Arg Leu Thr Lys Gln Met Asp Glu Phe
        275                 280                 285

His Ser Leu Leu Gly Gly Leu Asp Val His Pro Leu Lys Asp Arg Trp
    290                 295                 300

Ile Met Asp Glu Pro Phe Glu Phe Thr Phe Ser Pro Glu Val Ala Pro
305                 310                 315                 320

Ala Met Asp Met Pro Ser Thr Asp Asp Val Ile Val Thr Leu Ser Arg
                325                 330                 335

Ser Glu Gly Ser Arg Pro Ser Cys Phe Thr Ala Trp Lys Gly Ser Ser
            340                 345                 350

Glu Ser Lys Tyr Val Ala Gly Gln Val Val Gly Glu Ser Gln Lys Leu
        355                 360                 365

Leu Asn Lys Val Val Ala Gly Gly Ala Trp Ala Ser Asn Tyr Gly Gly
    370                 375                 380
```

-continued

```
Arg Thr Met Val Arg Ala Gln Gly Ile Asn Ser Asn Thr His Val Met
385                 390                 395                 400

Thr Glu Arg Arg Arg Glu Lys Leu Asn Glu Met Phe Leu Val Leu
            405                 410                 415

Lys Ser Leu Val Pro Ser Ile His Lys Val Asp Lys Ala Ser Ile Leu
            420                 425                 430

Thr Glu Thr Ile Gly Tyr Leu Arg Glu Leu Lys Gln Arg Val Asp Gln
        435                 440                 445

Leu Glu Ser Ser Arg Ser Pro Ser His Pro Lys Glu Thr Thr Gly Pro
    450                 455                 460

Ser Arg Ser His Val Val Gly Ala Arg Lys Lys Ile Val Ser Ala Gly
465                 470                 475                 480

Ser Lys Arg Lys Ala Pro Gly Leu Glu Ser Pro Ser Asn Val Val Asn
            485                 490                 495

Val Thr Met Leu Asp Lys Val Val Leu Leu Glu Val Gln Cys Pro Trp
            500                 505                 510

Lys Glu Leu Leu Met Thr Gln Val Phe Asp Ala Ile Lys Ser Leu Cys
        515                 520                 525

Leu Asp Val Val Ser Val Gln Ala Ser Thr Ser Gly Gly Arg Leu Asp
    530                 535                 540

Leu Lys Ile Arg Ala Asn Gln Gln Leu Ala Val Gly Ser Ala Met Val
545                 550                 555                 560

Ala Pro Gly Ala Ile Thr Glu Thr Leu Gln Lys Ala Ile
                565                 570
```

FERTILITY RESTORATION IN PLANTS

CROSS REFERENCE TO RELATED APPLICATIONS

This application is a 371 national stage entry of PCT patent application PCT/US2019/51019, filed Sep. 13, 2019, which claims benefit of and priority to U.S. Provisional Application No. 62/832,716, filed Apr. 11, 2019; U.S. Provisional Application No. 62/815,261, filed Mar. 7, 2019; and U.S. Provisional Application No. 62/731,252, filed Sep. 14, 2018; the entire contents of each is herein incorporated by reference.

FIELD

The present invention relates to the field of plant molecular biology, more particularly to impacting male fertility.

REFERENCE TO SEQUENCE LISTING SUBMITTED ELECTRONICALLY

The official copy of the sequence listing is submitted electronically via EFS-Web as an ASCII formatted sequence listing with a file named 7795WOPCT_seqlisting_ST25.txt, produced on Sep. 8, 2019, and having a size of 97 kilobytes and is filed concurrently with the specification. The sequence listing contained in this ASCII formatted document is part of the specification and is herein incorporated by reference in its entirety.

BACKGROUND

Development of hybrid plant breeding has made possible considerable advances in quality and quantity of crops produced. Increased yield and combination of desirable characteristics, such as resistance to disease and insects, heat and drought tolerance, along with variations in plant composition are all possible because of hybridization procedures. These procedures frequently rely heavily on providing for a male parent contributing pollen to a female parent to produce the resulting hybrid.

Field crops are bred through techniques that take advantage of the plant's method of pollination. A plant is self-pollinating if pollen from one flower is transferred to the same or another flower of the same plant or a genetically identical plant. A plant is cross-pollinated if the pollen comes from a flower on a different plant.

In certain species, such as *Brassica campestris*, the plant is normally self-sterile and can only be cross-pollinated. In self-pollinating species, such as soybeans, cotton and wheat, the male and female plants are anatomically juxtaposed. During natural pollination, the male reproductive organs of a given flower pollinate the female reproductive organs of the same flower. Maize has male flowers, located on the tassel, and female flowers, located on the ear, on the same plant and can be bred by both self-pollination and cross-pollination techniques.

During hybrid seed production, it is desirable to prevent self-pollination of the female inbred to avoid production and harvesting of female inbred seeds, since they exhibit less vigor than the hybrid seeds. To increase commercial quantities of the resulting hybrid seed, hybrid seed is often obtained using male-sterile female parents and male parents.

SUMMARY

Provided herein are compositions and methods of restoring male fertility in a male-sterile plant. Male-fertility may be restored to the male-sterile plant by providing a plant restoration donor chromosomal component from a different species or plant than the male-sterile plant. The plant restoration donor chromosomal component contains a male-fertility restoration locus that functionally complements the male-sterility phenotype of a plant rendered male-sterile due to one or more homozygous recessive mutations in a male-fertility polynucleotide. The male-fertility restoration locus is linked to a plant-derived polynucleotide that confers a plant phenotypic marker. Also provided herein are plants, plant cells, and seeds that have one or more homozygous mutations in a male-fertility polynucleotide and contain the plant restoration donor chromosomal component. In some examples, the plant restoration donor chromosomal component plant substitutes for a chromosome native to the male-sterile plant so that the plant produces euploid seed.

In some embodiments disclosed herein, plant restoration donor chromosomal components are modified with respect to one or more plant-derived polynucleotides that confer a plant phenotypic marker and/or one or more male-fertility restoration loci. For example, a modified plant-derived polynucleotides and/or male-fertility restoration locus may be modified in its polynucleotide sequence, copy number, expression level, or location within the plant restoration donor chromosomal component as compared to a native, non-modified plant-derived polynucleotide that confers a plant phenotypic marker or male-fertility restoration locus. Also disclosed herein are plants, plant cells, and seeds having these plant restoration donor chromosomal components.

Accordingly, described herein are methods for making and using such plants. Maintainer plants having any of the plant restoration donor chromosomal components described herein may be used to produce seed by allowing them to self-fertilize. The seeds, plants, or parts thereof containing the plant restoration donor chromosomal component may be identified using the plant phenotypic marker, for example, in seed sorting. Absence of the plant phenotypic marker's expression in the seeds indicates that the seeds do not contain the plant restoration donor chromosomal component and, when planted, will give rise to male-sterile female plants. Conversely, the presence of the plant phenotypic marker in seeds indicates that the seeds contain the plant restoration donor chromosomal component and, when planted, will give rise to male-fertile plants. Such seeds and plants may be used in the maintenance of male-sterility, male-sterile female inbreds for hybrid and seed increase production.

DETAILED DESCRIPTION

Figure 1:
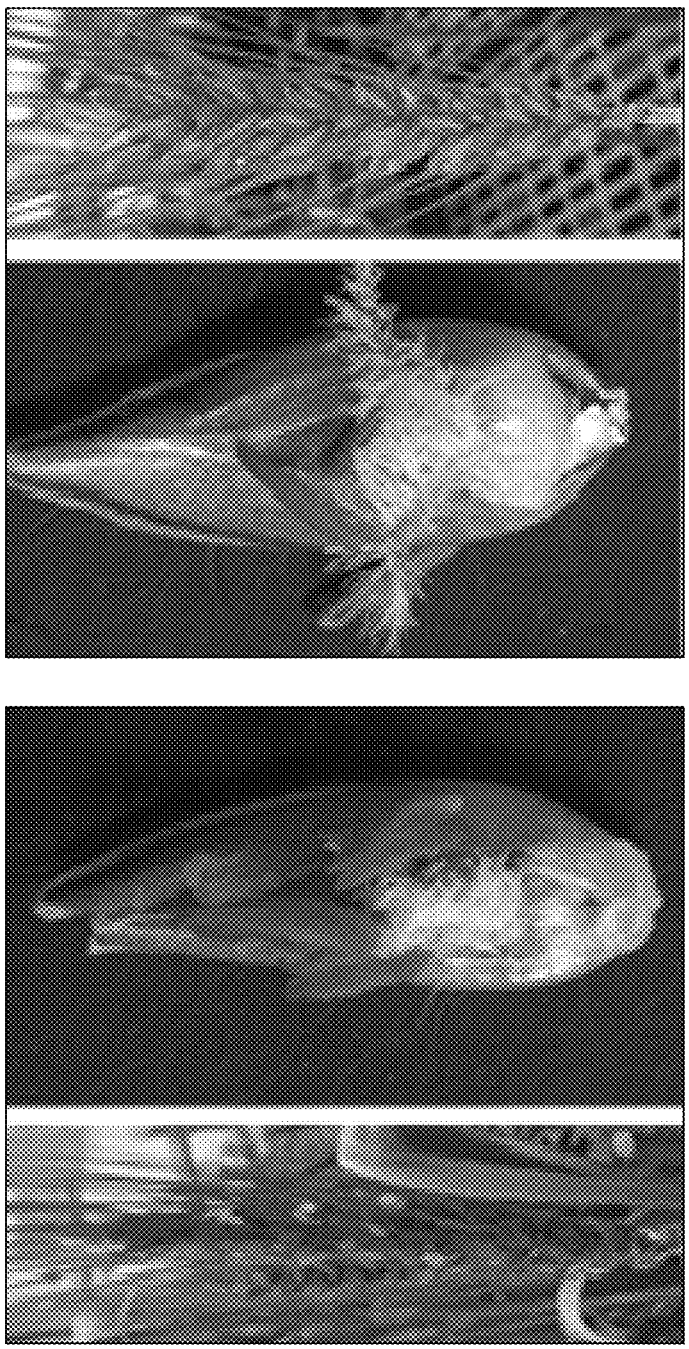
FIG. 1 shows examples of phenotypes in F3 generation in wheat. Part A) shows blue-colored wheat seed that will give rise to male-fertile wheat plants and part B) shows white-colored (non-blue colored) seed that will give rise to male-sterile female wheat plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Provided herein are plants, plant parts, plant cells or seeds having a plant restoration donor chromosomal component that can be used to restore male-fertility to male-sterile plants and facilitate the identification of plant parts, plant cells or seeds having the plant restoration donor chromosomal component. As used herein, a "plant restoration donor chromosomal component" is a chromosome or fragment thereof that includes a plant-derived polynucleotide that confers a plant phenotypic marker linked to a male-fertility restoration locus. As used herein, the term "plant-derived" indicates that the polynucleotide that confers the plant phenotypic marker is from a plant. In some examples, the plant-derived polynucleotide that confers the plant phenotypic marker is endogenous with respect to the plant restoration donor chromosomal component and male-fertility restoration locus. As used herein, the term "endogenous" or "native" or "natively" means normally present in the specified plant, present in its normal state or location in the chromosome (non-modified), plant cell, or plant.

In some examples, the plant-derived polynucleotide is exogenous with respect to the plant restoration donor chromosomal component, plant, or plant cell into which it is being introduced. The term "exogenous" means not normally present in the chromosomal component, plant, plant cell; not present in its normal state or location in the chromosomal component, plant, or plant cell, is introduced into the chromosomal component, plant cell or plant, or originates from a different chromosome, type of plant, plant species, or, if from the same chromosome, type of plant, plant species, is in a different location, modified from its native form in composition and/or genomic locus by deliberate human intervention. In some examples, the plant restoration donor chromosomal component includes one or more plant-derived polynucleotides that confer the plant phenotypic marker including, but not limited to, one or more native, edited, repositioned, replaced, or inserted plant-derived polynucleotides that confer the plant phenotypic marker or combinations thereof. In embodiments where there are two or more plant-derived polynucleotides, the polynucleotides may be the same or different from one another, for example, with respect to their sequences, such as their origin, e.g. plant type or species, polynucleotide or amino acid sequence or location in the plant restoration donor chromosomal component. In some examples, the one or more plant-derived polynucleotides that confer the plant phenotypic marker is exogenous with respect to the plant, plant cell, or plant restoration donor chromosomal component into which it is being introduced or combinations thereof.

Expression of the plant phenotypic marker in seed allows for the seed to be identified, selected, and/or sorted from seeds that do not contain the plant restoration donor chromosomal component, i.e. not having the plant-derived polynucleotide that confers the plant phenotypic marker. In some aspects, the plant phenotypic marker is a non-destructive marker.

The plant phenotypic marker may relate to the color, physiology, or morphology of the plant or seed. Examples of seed phenotypes that are suitable markers include but are not limed to seed color, seed color intensity or pattern, seed shape, seed surface texture, seed size including seed size width and/or length, seed density, or other seed characteristics. Examples of seed phenotypic color markers include but are not limited to blue aleurone, P gene that regulates flavonoid synthesis in maize, anthocyanin, Kala 4, and other endosperm coloring traits. In some examples, the plant-derived polynucleotide is ThMYC4E and confers a blue aleurone phenotype. See, Li, Na et al. "ThMYC4E, Candidate Blue Aleurone 1 Gene Controlling the Associated Trait in *Triticum Aestivum*." Ed. Harsh Raman. *PLoS ONE* 12.7 (2017): e0181116. *PMC*. Web. 13 September 2018, herein incorporated by reference in its entirety. See, published PCT patent application, WO2019090496, herein incorporated by reference in its entirety and in the instant sequence listing. In some embodiments where there are two or more plant-derived polynucleotides, the two plant-derived polynucleotides are polynucleotides encoding blue alerone color markers that confer a blue aleurone phenotype to the seed and may be used for seed identification, selection, and sorting. The color markers be the same or different from one another, for example, with respect to their sequences, such as their origin, e.g. plant type or species, polynucleotide or amino acid sequence or location in the plant restoration donor chromosomal component.

As desired, the plant-derived polynucleotides that confer the plant phenotypic marker may be modified to increase its expression in the plant, for example, to increase the expression of the plant phenotypic marker in a plant, plant part thereof, or seed. In some aspects, the regulatory region of the plant-derived polynucleotide may be modified to increase expression of the plant phenotypic marker, for example, by editing the existing regulatory region to replace, delete, and/or insert nucleotides for improved expression. See, for example, PCT Patent publication WO2018183878, published Oct. 4, 2018, incorporated herein by reference in its entirety Alternatively, or in addition to, nucleotides in the plant phenotypic marker on the plant restoration donor chromosomal component may be modified to change the polynucleotide so it uses codons preferred by the host plant.

In some embodiments, the blue aleurone gene in the plant restoration chromosomal component has a nucleic acid sequence encoding an amino acid sequence with at least 80%, at least 85%, at least 90%, at least 95%), at least 96%, at least 97%, at least 98%, or at least 99% sequence identity to the amino acid sequence of SEQ ID NO: 41 or 42, variants, or fragments thereof. The nucleic acid sequence encoding the polypeptide that confers the blue aleurone phenotype may be synthesized, isolated, or obtained from any number of sources, including but not limited to, *Agropyron, Thinopyrum*, or *Triticum*, such as *Agropyron elongatum, Agropyron trichophorum, Triticum thaoudar, Triticum Aestivum, Triticum monococcum*, and *Thinopyrum ponticum*. The source of blue aleurone and the plant restoration donor chromosomal component may be from Sebesta Blue, Blue Sando, Blue Baart, Blue Onas, Blue 1, PBB, or Blue Norco, or other addition line that comprises a polynucleotide encoding blue aleurone. The presence of blue aleurone in the seed may be indicated by the appearance of a blue color in the aleurone layer of the seed, confirmed using PCR, or any other suitable assays. The examples of plant phenotypic markers included herein are not meant to be limiting. Any desired plant phenotypic marker may be used in the methods and compositions described herein.

Seeds may be sorted into various populations using any suitable seed phenotypic marker. For example, the absence of the plant phenotypic marker in the seed, e.g. seed lacking the plant restoration donor chromosomal component, indicates the seed, when planted, will give rise to a male-sterile female plant. Plants from this seed may be used as male-sterile female inbreds for hybrid and seed increase production. The presence of the plant phenotypic marker in the seed, e.g. seed having the plant restoration donor chromosomal component, indicates that the seed will give rise to a male-fertile plant that may be used as a maintainer for the male-sterile female plant. As discussed elsewhere herein, the seeds may be sorted using any suitable approach or instrument so long as it has sufficient sensitivity to detect the difference between phenotypic marker expressing and non-expressing seeds.

In addition to the plant-derived polynucleotide that confers the plant phenotypic marker, the plant restoration donor chromosomal component includes a male-fertility restoration locus that is able to functionally complement the male-sterility phenotype of a plant. As used herein, a "male-fertility restoration locus" refers to one or more male-fertility polynucleotides that, when expressed in a male-sterile female plant, restores the plant to male-fertility by complementing the female plant's male sterile condition caused by one or more homozygous mutations in a male-fertility polynucleotide. Such mutations may be a substitution, a deletion, and/or an insertion of one or more nucleotides that results in conferring male-sterility to a plant. As used herein, the term "male-fertility polynucleotide" means one of the polynucleotides critical to a specific step in microsporogenesis, the term applied to the entire process of pollen formation. In some examples, the one or more male-fertility polynucleotides include but are not limited to Ms1, Ms5, Ms9, Ms22, Ms26, or Ms45. In some embodiments, the male-fertility restoration locus utilizes without limitation two or more male-fertility polynucleotides of Ms1, Ms5, Ms9, Ms22, Ms26, or Ms45 to complement a female plant's male sterile condition caused by one or more homozygous mutations in the Ms1, Ms5, Ms9, Ms22, Ms26, or Ms45 male-fertility polynucleotide, respectively.

As desired, the male-fertility restoration locus may be modified to increase expression of the male-fertility polynucleotide in the plant, for example, to complement male-sterility or restore male-fertility to a male-sterile plant. In some aspects, the regulatory region may be modified to increase expression of the male-fertility restoration locus or male-fertility polynucleotide, for example, by editing the existing regulatory region to replace, delete, and/or insert nucleotides for improved expression. See, for example, PCT Patent publication WO2018183878, published Oct. 4, 2018, incorporated herein by reference in its entirety. Alternatively, or in addition to, nucleotides in the male-fertility restoration locus or male-fertility polynucleotide on the plant restoration donor chromosomal component may be modified to change the polynucleotide so it uses codons preferred by the host plant.

In some examples, the male-fertility restoration locus is associated with increased male-fertile phenotype in a plant. The plant's male-fertility condition can be assessed by any suitable technique, for example, by observation of the plant's male tissue development, such as phenotyping of anthers and seed set on individual plants. See, for example, Example 1 herein.

In some examples, the male-fertility restoration locus includes, but is not limited to, one or more native, edited, replaced, repositioned, or inserted male-fertility polynucleotides or combinations thereof. In embodiments where there are two or more male-fertility polynucleotides in the male-fertility restoration loci, the male-fertility restoration loci may be the same or different from one another, for example, with respect to their sequences, such as their origin, e.g. plant type or species, polynucleotide or amino acid sequence or location in the plant restoration donor chromosomal component. In some aspects, the one or more male-fertility restoration locus is endogenous with respect to the plant, plant cell, or plant restoration donor chromosomal component into which it is being introduced or combinations thereof. In some aspects, the one or more male-fertility restoration locus is exogenous with respect to the plant, plant cell, or plant restoration donor chromosomal component into which it is being introduced or combinations thereof. The male-fertility restoration may include one or more male-fertility polynucleotides known to one skilled in the art, described herein, including homologs and orthologs of any the foregoing.

In one example, the male-fertility restoration locus functionally complements the male-sterility phenotype from one or more homozygous mutations in an endogenous male-fertility polynucleotide that confers male-sterility to the plant. This includes but is not limited to one or more homozygous recessive alleles for Ms1, Ms5, Ms9, Ms22, Ms26, or Ms45. Since Ms1 in wheat behaves as a single gene recessive, in some embodiments, only the ms/male-fertility polynucleotide or allele located on chromosome 4BS may need to be mutated to confer male-sterility to a wheat plant.

There are a number of known male-fertility polynucleotides and male-fertility mutants from wheat and other species, including but not limited to Ms1, Ms5, Ms9, Ms22, Ms26, or Ms45.

PCT Patent publication WO2016048891, published Mar. 31, 2016, describes a male fertility gene referred to as "MS1" that is located on wheat chromosome 4BS and encodes a glycosylphosphatidylinositol (GPI)-anchored nsLTP (LTPG) polypeptide (also referred to as TaLTPGI) important to male fertility. Examples of DNA and polypeptide sequences of wheat Ms1 sequences are disclosed in WO2016048891, published Mar. 31, 2016, and WO2019118342, published Jun. 20, 2019, each of which are incorporated herein in its entirety, and in the instant sequence listing.

Wheat Ms5 is a glycosylphosphatidylinositol-anchored lipid transfer protein required for normal pollen exine development and the gene is located on wheat chromosome 3A. Examples of DNA and polypeptide sequences of wheat Ms5 are disclosed in WO2019118342, published Jun. 20, 2019, each of which are incorporated herein in its entirety, and in the instant sequence listing.

U.S. Patent publication US20150191743 A1, published Jul. 9, 2015, describes a male fertility gene referred to as "MS9" that is located on maize chromosome 1 and encodes a myb transcription factor critical to male fertility. The Ms9 phenotype was first identified in maize in 1932. Beadle, (1932) Genetics 17:413-431. It was found to be linked to the P1 gene on Chromosome 1. Breakdown of male reproductive tissue development occurs very early in premeiosis;

tapetal cells may be affected as well. Greyson, et al., (1980) Can. J. Genet. Cytol. 22:153-166. Examples of genomic DNA and polypeptide sequences of maize Ms9 are disclosed in US patent publication 20150191743, published on Jul. 9, 2015, incorporated herein in its entirety. Wheat Ms9 is located on the long arm of wheat chromosome 4. Examples of genomic DNA and polypeptide sequences of wheat Ms9 are disclosed in US patent publication US20190177722A1, published on Jun. 13, 2019, incorporated herein in its entirety, and in the instant sequence listing.

U.S. Patent publication US20090038026A1, published Feb. 5, 2009, describes a male fertile gene referred to as "Msca1" or "MS22" that is located on maize chromosome 7 and encodes a protein critical to male fertility. Mutations referred to as ms22 or msca1 were first noted as phenotypically male sterile with anthers which did not extrude from the tassel and lacked sporogenous tissue. West and Albertsen (1985) *Maize Newsletter* 59:87; Neuffer et al. (1977) Mutants of maize. Cold Spring Harbor Laboratory Press, Cold Spring Harbor, N.Y. The mutant locus was originally referred to as ms22 but was later changed to msca1, or male sterile converted anther. See Chaubal et al. "The transformation of anthers in the msca1 mutant of maize" *Planta* (2003)216:778-788. Wheat Ms22 is located on the long arm of wheat chromosome 2. Examples of genomic DNA and polypeptide sequences of wheat Ms22 are disclosed in US patent publication US20190177722A1, published on Jun. 13, 2019, incorporated herein in its entirety, and in the instant sequence listing.

U.S. Pat. No. 7,517,975, issued Apr. 14, 2009, describes a male fertility gene referred to as "MS26" (also known as SB200 or SBMu200) that is located on maize chromosome 1. Ms26 sequences in maize or rice, e.g. as disclosed in U.S. Pat. No. 7,919,676 or 8,293,970. In wheat, the Ms26 gene is located on wheat chromosome 4AS. Examples of genomic DNA and polypeptide sequences of wheat Ms26 are disclosed in US patent publication US20190177722A1, published on Jun. 13, 2019, incorporated herein in its entirety, and in the instant sequence listing.

U.S. Pat. No. 5,478,369 issued Dec. 26, 1995 describes a male fertile gene referred to as "MS45" cloned on maize chromosome 9. In wheat, the Ms45 gene is located on the long arm of wheat chromosome 4. Examples of genomic DNA and polypeptide sequences of wheat Ms45 are disclosed in US patent publication US20190177722A1, published on Jun. 13, 2019, incorporated herein in its entirety, and in the instant sequence listing.

Male-sterile female plants for use in the methods and compositions described herein can be generated using any number of methods recognized in the art, including but not limited to mutagenesis, suppression, and genome editing. Mutations that cause male sterility in crop plants such as maize, wheat and rice have been produced by a variety of methods such as X-rays or UV-irradiations, chemical treatments, or transposable element insertions (Chaubal et al. 2000) Am J Bot 87:1193-1201). Suppression technology such as antisense, co-suppression, RNAi, hairpin formations may be used to disrupt or prevent expression of the fertility gene alleles to create a male-sterile female plant, e.g. to create homozygous recessive alleles that confer male-sterility to the plant. In some instances, male-sterility results from using genome editing technology to introduce a genetic modification (mutation) near or into an endogenous male-fertility gene, e.g. a male-fertility polynucleotide, to cause sterility. See, WO2015026883, published on Feb. 26, 2015, and Singh, M., Kumar, M., Albertsen, M. C. et al. Plant Mol Biol (2018) 97: 371-383. Accordingly, the methods may employ CRISPR technology using a guide RNA/Cas endonuclease system, where the Cas endonuclease is guided by the guide RNA to recognize and optionally introduce a double strand break at a specific target site into the plant genome of a cell. In some examples, the wheat genomes (A, B, and D) contain homologous genes that have similar gene structure and function, requiring triple mutants to result in a male-sterile phenotype, e.g. one, two, or three homozygous mutations in a male-fertility polynucleotide. In some embodiments, the male-sterile phenotype is caused by the introduction of genetic modification (mutation) of a target site located in or near one or more endogenous male fertility gene locus of Ms1, Ms5, Ms9, Ms22, Ms26 or Ms45 in a plant cell's genome. See, for example, US20190177722A1, published on Jun. 13, 2019, and WO2019118342, published Jun. 20, 2019, each of which are incorporated herein in its entirety.

Accordingly, known or created ms1/ms1/; ms5/ms5; ms9/ms9/; ms22/ms22/; ms26/ms26/; or ms45/ms45 male-sterile edited or mutant plants may be used in the methods and compositions described herein, for example, for use as male-sterile female plants in hybrid and hybrid seed production. Since Ms1 in wheat behaves as a single gene recessive, in some embodiments only the ms/male-fertility polynucleotide or allele located on chromosome 4BS may need to be mutated to confer male-sterility to a wheat plant.

In some embodiments, provided herein are compositions and methods to complement and restore male fertility to male-sterile female wheat plants containing one or more homozygous mutations in a Ms1, Ms5, Ms9, Ms22, Ms26 or Ms45 male-fertility polynucleotide which confer male-sterility to the wheat plant. In some examples, the male-sterile plant contains one or more homozygous mutations in a recessive sporophytic male fertility polynucleotide. In some examples, these male-sterile wheat plants may be restored to male fertility when a plant restoration donor chromosomal component from a non-wheat species is used to functionally complement the one or more homozygous Ms1, Ms5, Ms9, Ms22, Ms26 or Ms45 mutations that confer male-sterility to the wheat plant.

In some embodiments, the wheat Ms1 male-fertility polynucleotide sequences include (a) a polynucleotide comprising the sequence set forth in SEQ ID NO:1, 3, or 5; (b) a polynucleotide having at least 85%, 90% or 95% sequence identity to SEQ ID NO: 1, 3, or 5; (c) a polynucleotide that encodes a polypeptide having at least 85%, 90% or 95% sequence identity to SEQ ID NO:2, 4, or 6; and (d) a polynucleotide that encodes a polypeptide of SEQ ID NO: 2, 4, or 6.

In some embodiments, the wheat Ms5 male-fertility polynucleotide sequences include (a) a polynucleotide comprising the sequence set forth in SEQ ID NO:7, 9, 12, or 14; (b) a polynucleotide having at least 85%, 90% or 95% sequence identity to SEQ ID NO: 7, 9, 12, or 14; (c) a polynucleotide that encodes a polypeptide having at least 85%, 90% or 95% sequence identity to SEQ ID NO: 8, 10, 11, 13, or 15; and (d) a polynucleotide that encodes a polypeptide of SEQ ID NO: 8, 10, 11, 13, or 15.

In some embodiments, the wheat Ms9 male-fertility polynucleotide sequences include (a) a polynucleotide comprising the sequence set forth in SEQ ID NO:16, 18, or 20; (b) a polynucleotide having at least 85%, 90% or 95% sequence identity to SEQ ID NO: 16, 18, or 20; (c) a polynucleotide that encodes a polypeptide having at least 85%, 90% or 95% sequence identity to SEQ ID NO:17, 19, or 21; and (d) a polynucleotide that encodes a polypeptide of SEQ ID NO: 17, 19, or 21.

In some embodiments, the wheat Ms22 male-fertility polynucleotide sequences include (a) a polynucleotide comprising the sequence set forth in SEQ ID NO:22, 24, or 26; (b) a polynucleotide having at least 85%, 90% or 95% sequence identity to SEQ ID NO: 22, 24, or 26; (c) a polynucleotide that encodes a polypeptide having at least 85%, 90% or 95% sequence identity to SEQ ID NO: 23, 25, or 27; and (d) a polynucleotide that encodes a polypeptide of SEQ ID NO: 23, 25, or 27.

In some embodiments, the wheat Ms26 male-fertility polynucleotide sequences include (a) a polynucleotide comprising the sequence set forth in SEQ ID NO:28, 30, or 32; (b) a polynucleotide having at least 85%, 90% or 95% sequence identity to SEQ ID NO: 28, 30, or 32; (c) a polynucleotide that encodes a polypeptide having at least 85%, 90% or 95% sequence identity to SEQ ID NO: 29, 31, or 33; and (d) a polynucleotide that encodes a polypeptide of SEQ ID NO: 29, 31, or 33.

In some embodiments, the wheat Ms45 male-fertility polynucleotide sequences include (a) a polynucleotide comprising the sequence set forth in SEQ ID NO:34, 36, or 38; (b) a polynucleotide having at least 85%, 90% or 95% sequence identity to SEQ ID NO: 34, 36, or 38; (c) a polynucleotide that encodes a polypeptide having at least 85%, 90% or 95% sequence identity to SEQ ID NO: 35, 37, or 39; and (d) a polynucleotide that encodes a polypeptide of SEQ ID NO: 35, 37, or 39.

TABLE 1

Summary of SEQ ID NOS:

| SEQ ID NO: | Description |
|---|---|
| 1 | Wheat Ms1 A genomic (exon-intron) |
| 2 | Wheat Ms1 A amino acid |
| 3 | Wheat Ms1 B genomic (exon-intron) |
| 4 | Wheat Ms1 B amino acid |
| 5 | Wheat Ms1 D genomic (exon-intron) |
| 6 | Wheat Ms1 D amino acid |
| 7 | Wheat Ms5 3A genomic (exon-intron) |
| 8 | Wheat Ms5 3A amino acid |
| 9 | Wheat Ms5 3B genomic (exon-intron) |
| 10 | Wheat Ms5 3B amino acid |
| 11 | Wheat Ms5 3B amino acid |
| 12 | Wheat Ms5 3D genomic (exon-intron) |
| 13 | Wheat Ms5 3D amino acid |
| 14 | Wheat Ms5 3D genomic (exon-intron) |
| 15 | Wheat Ms5 3D amino acid |
| 16 | Wheat Ms9 4AS genomic (exon/intron) |
| 17 | Wheat Ms9 4AS amino acid |
| 18 | Wheat Ms9 4BL genomic (exon/intron) |
| 19 | Wheat Ms9 4BL amino acid |
| 20 | Wheat Ms9 4DL genomic (exon/intron) |
| 21 | Wheat Ms9 4DL amino acid |
| 22 | Wheat Ms22 AL genomic (exon/intron) |
| 23 | Wheat Ms22 AL amino acid |
| 24 | Wheat Ms22 BL genomic (exon/intron) |
| 25 | Wheat Ms22 BL amino acid |
| 26 | Wheat Ms22 DL genomic (exon/intron) |
| 27 | Wheat Ms22 DL amino acid |
| 28 | Wheat Ms26 4AS genomic (exon/intron) |
| 29 | Wheat Ms26 4AS amino acid |
| 30 | Wheat Ms26 4BL genomic (exon/intron) |
| 31 | Wheat Ms26 4BL amino acid |
| 32 | Wheat Ms26 4DL genomic (exon/intron) |
| 33 | Wheat Ms26 4DL amino acid |
| 34 | Wheat Ms45 4AS genomic (exon/intron) |
| 35 | Wheat Ms45 4AS amino acid |
| 36 | Wheat Ms45 4BL genomic (exon/intron) |
| 37 | Wheat Ms45 4BL amino acid |
| 38 | Wheat Ms45 4DL genomic (exon/intron) |
| 39 | Wheat Ms45 4DL amino acid |
| 40 | Guide for gene editing |
| 41 | Thinopyrum ponticum blue aleurone amino acid |
| 42 | Thinopyrum ponticum blue aleurone amino acid |

In some aspects, the plant-derived polynucleotide that confers the plant phenotypic marker and the male-fertility restoration locus are natively linked to each other on the plant restoration donor chromosomal component. In some aspects, the plant-derived polynucleotide that confers the plant phenotypic marker and the male-fertility restoration locus are natively linked to each other and are both located on the same side of the centromere on the plant restoration donor chromosomal component, that is, on the same chromosomal arm. In some embodiments, they are both are linked together and located on the long arm of the plant restoration donor chromosomal component or both located on the short arm of the plant restoration donor chromosomal component and not separated by a centromere. The present disclosure described herein is based, in part, on the discovery that the 4EL chromosome from Blue Norco is able complement Tams45-abd mutations, see, for example, Example 1, herein. In one embodiment, the plant phenotypic marker is blue aleurone and is on the same side of the centromere as a male-fertility restoration locus that functionally complements the male-sterility phenotype in a male-sterile female wheat plant that has homozygous Ms45 mutations.

The plant restoration donor chromosomal component may be from any plant so long as it is able to restore fertility to a male-sterile plant so that the plant produces viable pollen capable of fertilizing a plant, for example, itself. In some aspects, the plant restoration donor chromosomal component is from maize, rice, sorghum, rye, barley, wheat, millet, oats, sugarcane, turfgrass, triticale, switchgrass, wheatgrass, fonio, soybean, canola, alfalfa, sunflower, cotton, tobacco, peanut, potato, tobacco, *Arabidopsis*, safflower, *Thinopyrum, Aegilops, Secale, Haynaldia, Elyymus, Hordeum*, or a related species thereof. In some aspects, the plant restoration donor chromosomal component comprises chromosome 4 from a plant. In some embodiments, the plant restoration donor chromosomal component is a 4E, 4EL, or 4H chromosome from a species of *Triticum, Thinopyrum, Aegilops, Secale, Haynaldia, Elyymus*, or *Hordeum*, or a related species thereof. The orthologous counterpart of the plant restoration donor chromosomal component in other species may be on the same chromosome, e.g. 4, or located on a different chromosome. In some aspects, the plant phenotypic marker and the male-fertility restoration locus are linked together on chromosome 4 which may be used as a plant restoration donor chromosomal component.

In some cases, the male-fertility restoration locus and the plant-derived polynucleotide that confers the plant phenotypic marker are not closely linked or natively linked. Molecular and biological techniques including genome editing technology such as CRISPR, Talons, meganucleases, and the like, can be used to increase their genetic linkage and/or decrease their physical distance on the plant restoration donor chromosomal component.

In some examples, one or more plant-derived polynucleotides conferring the plant phenotypic marker is inserted in, repositioned within, or rearranged on the plant restoration donor chromosomal component to increase the genetic linkage, decrease the recombination frequency, lower the cross-over frequency, and/or decrease the physical distance or combinations thereof with respect to one or more male-fertility restoration locus on the plant restoration donor chromosomal component. One or more of the plant-derived polynucleotide conferring the plant phenotypic marker may be endogenous or exogenous with respect to the plant restoration donor chromosomal component and/or one or more male-fertility restoration locus. One or more of the male-fertility restoration locus may be endogenous or exogenous with respect to the plant restoration donor chromosomal component.

In some examples, one or more male-fertility restoration locus is inserted in, repositioned within, or rearranged on the plant restoration donor chromosomal component to increase the genetic linkage, decrease the recombination frequency, lower the cross-over frequency, and/or decrease the physical distance or combinations thereof with respect to one or more plant-derived polynucleotides conferring the plant phenotypic marker on the plant restoration donor chromosomal component. One or more of the male-fertility restoration locus may be endogenous or exogenous with respect to the plant restoration donor chromosomal component or the one or more plant-derived polynucleotides conferring the plant phenotypic marker. One or more of the plant-derived polynucleotides conferring the plant phenotypic marker may be endogenous or exogenous with respect to the plant restoration donor chromosomal component.

In other embodiments, the male-fertility restoration locus and the plant-derived polynucleotide conferring the plant phenotypic marker have been edited, inserted, repositioned, or rearranged or combinations thereof so that they are both at different locations on the plant restoration donor chromosomal component than their native locations on the plant restoration donor chromosomal component. In some examples, the plant phenotypic marker and male-fertility restoration locus are located on the same side of the centromere of the plant restoration donor chromosomal component. In some embodiments where there is more than one male-fertility restoration locus and/or plant-derived polynucleotide conferring the plant phenotypic marker, at least one male-fertility restoration locus and at least one plant-derived polynucleotide are at different locations on the plant restoration donor chromosomal component than their native locations. In some embodiments, the plant-derived polynucleotide conferring the plant phenotypic marker and the one or more male-fertility restoration locus have less physical distance between them as compared to the physical distance between the original plant-derived polynucleotide and the original male-fertility restoration locus when located at their native locations. In some embodiments, the plant-derived polynucleotide conferring the plant phenotypic marker and the one or more male-fertility restoration locus have increased genetic linkage between them as compared to the genetic linkage between the original plant-derived polynucleotide and the original male-fertility restoration locus when located at their native locations. In some aspects, the plant-derived polynucleotide conferring the plant phenotypic marker and the one or more male-fertility restoration locus have decreased recombination frequency as compared to the recombination frequency between the original plant-derived polynucleotide and the original male-fertility restoration locus when located at their native locations. In some aspects, the plant-derived polynucleotide conferring the plant phenotypic marker and the one or more male-fertility restoration locus have lower cross-over frequency as compared to the cross-over frequency between the original plant-derived polynucleotide and the original male-fertility restoration locus when located at their native locations.

In some embodiments, where one or more male-fertility restoration locus has been inserted into the plant restoration donor chromosomal component, the the native or original male-fertility restoration locus may be disrupted so that it no longer expresses and cannot restore male-fertility in a male-sterile plant. In some aspects, the method may include disrupting the native or original male-fertility restoration locus if it does not reside on the same side of the centromere of the plant restoration donor chromosomal component as the plant-derived polynucleotide conferring the plant phenotypic marker or is not closely linked to the plant-derived polynucleotide from a genetics perspective.

In some embodiments, where one or more plant-derived polynucleotides conferring the plant phenotypic marker has been inserted into the plant restoration donor chromosomal component, the native or original plant-derived polynucleotide conferring the plant phenotypic marker may be disrupted so that it no longer expresses and cannot confer a marker phenotype to a plant or parts thereof. In some aspects, the method may include disrupting the native or original plant-derived polynucleotide conferring the plant phenotypic marker if it does not reside on the same side of the centromere of the plant restoration donor chromosomal component as the male-fertility restoration locus or is not closely linked to the male-fertility restoration locus from a genetics perspective.

In some embodiments, the plant restoration donor chromosomal component has one or more modified plant-derived polynucleotides that confer a plant phenotypic marker linked to one or more male-fertility restoration loci. For example, the modified plant-derived polynucleotides that confer a plant phenotypic marker may be modified in its polynucleotide sequence, copy number, expression level, or location within the plant restoration donor chromosomal component as compared to the polynucleotide sequence, copy number, expression level, or location of a native, non-modified plant-derived polynucleotide that confers a plant phenotypic marker.

In some embodiments, the plant restoration donor chromosomal component has one or more plant-derived polynucleotides that confer a plant phenotypic marker linked to one or more modified male-fertility restoration loci. For example, the modified male-fertility restoration loci may be modified in its polynucleotide sequence, copy number, expression level, or location within the plant restoration donor chromosomal component as compared to the polynucleotide sequence, copy number, expression level, or location of a native, non-modified male-fertility restoration locus.

In some embodiments, the plant restoration donor chromosomal component has one or more modified plant-derived polynucleotides that confer a plant phenotypic marker linked to one or more modified male-fertility restoration loci. For example, the modified male-fertility restoration loci may be modified in its polynucleotide sequence, copy number, expression level, or location within the plant restoration donor chromosomal component as compared to the polynucleotide sequence, copy number, expression level, or location of a native, non-modified male-fertility restoration locus. For example, the modified plant-derived polynucleotides that confer a plant phenotypic marker may be modified in its polynucleotide sequence, copy number, expression level, or location within the plant restoration donor chromosomal component as compared to the polynucleotide sequence, copy number, expression level, or location of a native, non-modified plant-derived polynucleotide that confers a plant phenotypic marker.

In some aspects, the plant-derived polynucleotide that confers the plant phenotypic marker and the male-fertility restoration locus reside on opposite arms of the chromosome. Any suitable technology and technique may be used to bring the plant-derived polynucleotide that confers the plant phenotypic marker and the male-fertility restoration locus to the same arm of the chromosome, for example, translocation, genome editing, pericentric inversions, or combinations thereof.

Figure 3:
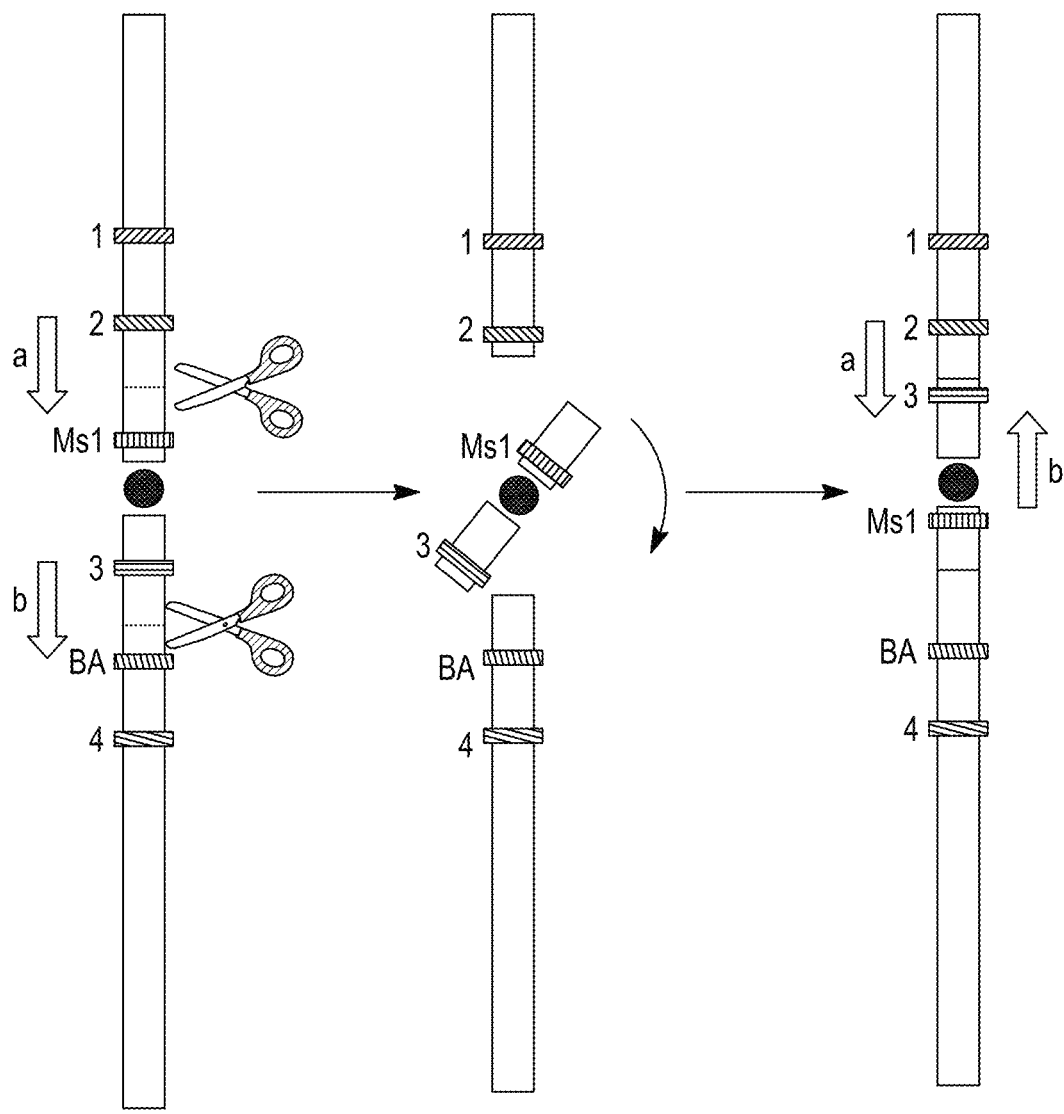
FIG. 3 illustrates one embodiment of a pericentric inversion of Ms1 to increase linkage with BA (blue aleurone) on a chromosome.

In one embodiment, the Ms1 male-fertility restoration locus and the plant-derived polynucleotide encoding the plant phenotypic marker of blue aleurone (Ba1) gene are initially located on different chromosome arms. In some aspects, the Ms1 male-fertility restoration locus resides on chromosome 4ES from *Agropyron elongatum* or 4HS from barley (*Hordeum vulgare*) and the blue aleurone (Ba1) gene on 4EL from Blue Norco. In one embodiment, double-strand breaks in a hybrid (chimeric) plant restoration donor chromosomal component of 4HS-4EL are induced, for example, one double-strand break between the barley Ms1-H gene and the telomere of 4HS, and one double-strand break between the Ba1 gene and the centromere of 4HS-4EL. The chromosome fragment containing the centromere and Ms1-H will be rejoined to the telomeric ends in the opposite orientation, resulting in a pericentric inversion, with Ms1-H and Ba1 now located on the same arm of the new chromosome. See, for example, FIG. 3.

The plant restoration donor chromosomal component may be introduced into a plant cell, plant part, or plant, for example, a male-sterile plant, using any suitable technique known to those in the art. In some approaches, the plant restoration donor chromosomal component is introduced into the plant cell, plant part, or plant using genome editing, transformation, embryo culture, or chromosomal translocation techniques. In some embodiments, the plant cell is a wheat plant cell that has one or more homozygous mutations in a male-fertility polynucleotide, for example, Ms45, and a plant restoration donor chromosomal component that functionally complements the male-sterile homozygous mutations conferring male-sterility to a wheat plant.

The plant restoration donor chromosomal component may be translocated into a plant's genome using any suitable methods. The translocation may be a Robertsonian or non-Robertsonian translocation. In some aspects, the plant restoration donor chromosomal component is translocated and substitutes for an existing plant chromosomal arm, for example, a wheat, barley, or rye plant. In some embodiments, the plant restoration donor chromosomal component may be used to replace the short or long arm of the plant's chromosome, e.g. wheat, barley, or rye.

In some embodiments, the plant restoration donor chromosomal component is introduced using a targeted approach so that the plant restoration donor chromosomal component is introduced into a location in the recipient plant's genome so that any potential undesirable effects on the recipient plant are minimized, avoided or the targeted location provides potential beneficial advantages. For example, the plant restoration donor chromosomal component may be introduced or substituted for a chromosomal arm in a wheat plant where the wheat plant lacking that chromosomal arm or pair of chromosomal arms (monosomic or ditelosomoic) has a normal phenotype. In another example, the plant restoration donor chromosomal component may be introduced or substituted for a chromosomal arm in a wheat plant where the lack of the chromosomal arm would have the effect of reducing transmission rates of the plant restoration donor chromosomal component, for example, reducing male or female transmission rates. In one embodiment, the plant restoration donor chromosomal component is substituted for the long arm of chromosome 5A (5AL) in a wheat plant, so that the result is the plant restoration donor chromosomal component-5AS.

In some examples, having a translocated and/or substituted plant restoration donor chromosomal component may confer advantages over an independent (addition) plant restoration donor chromosomal component. One advantage is reduced gametic transmission of the independent (addition) plant restoration donor chromosomal component, which allows for an increased percentage of seed that contain the one or more homozygous mutations in the male-fertility polynucleotide and do not contain the plant restoration donor chromosomal component to be produced during female seed increase.

Figure 4:
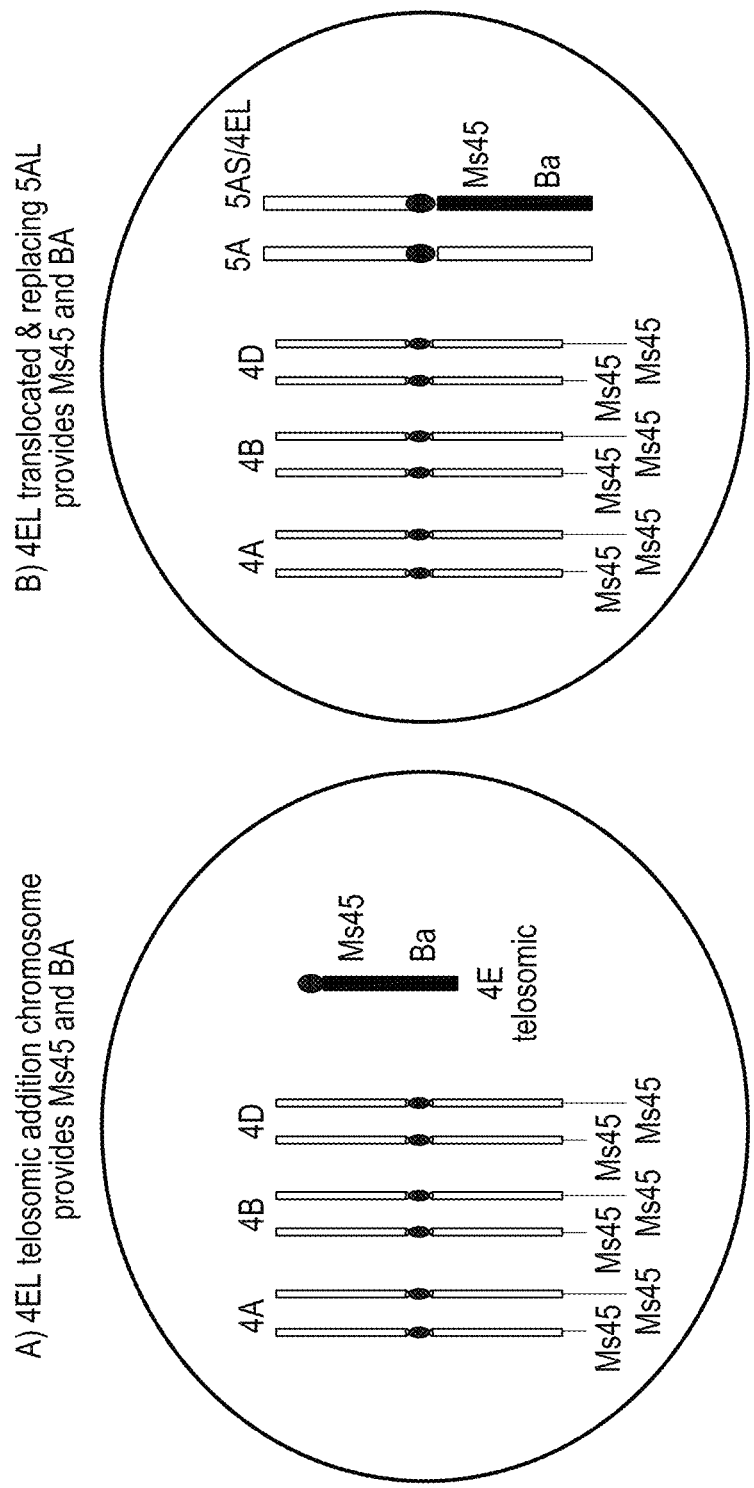
FIG. 4 shows one embodiment of a translocation and replacement of a wheat chromosomal arm with a plant restoration donor chromosomal component of 4E-Ms45. Part A shows a plant restoration chromosomal component of a 4EL telosomic addition chromosome that provides Ms45 and BA. Part B shows a plant restoration donor chromosomal component of 4EL that provides Ms45 and BA and translocates and replaces a 5AL wheat chromosome.

In some embodiments, a translocated, substituted plant restoration donor chromosomal component may be created via a Robertsonian translocation. See, for example, FIG. 4. Aneuploid stocks may be used to create wheat-chromosomal donor Robertsonian translocations in a directed manner by making the appropriate wheat and donor chromosomes in monosomic condition. The translocated, substituted plant restoration donor chromosomal component may be introgressed along with one or more homozygous mutations in the male-fertility polynucleotide or a single fertility gene recessive into various elite female lines to facilitate hybrid seed production. Since Ms1 behaves as a single gene recessive, in some embodiments, only the one mutation in the Ms1 polynucleotide or allele located on chromosome 4BS may need to be introgressed into female wheat lines to produce male-sterility.

In one example, the plant restoration donor chromosomal component is introduced into the male-sterile plant using breeding techniques. In some examples, the male-sterile plant is crossed with a plant comprising the plant restoration donor chromosomal component. The plant restoration donor chromosomal component may be introduced into a plant, for example, a male-sterile plant, using a plant that has the same base number of chromosomes as the recipient (e.g. male-sterile) plant. In some examples, the male-sterile plant is a wheat plant, e.g. diploid, tetraploid, or hexaploid. In some examples, the plant restoration donor chromosomal component may be from or introduced from a wheat plant, e.g. diploid, tetraploid, or hexaploid wheat, an *Aegilops, Secale, Agropyrin, Haynaldia, Hordeum*, or *Elyymus* plant, or any other plant that the male-sterile plant is cross-compatible with and can be fertilized by.

In some aspects, the plant restoration donor chromosomal component may be exogenous with respect to the recipient plant, e.g. a male-sterile plant, or its host plant, e.g. a male-fertile plant. For example, the plant restoration donor chromosomal component may be from a plant that is of a different species or plant than the male-sterile plant, for example, having a plant restoration donor chromosomal component from wheatgrass or barley in a wheat plant. Accordingly, in some examples, the plant restoration donor chromosomal component is from a non-wheat plant or species. In some embodiments, the plant restoration donor chromosomal component does not pair or recombine with any of the male-sterile female plant's chromosomes, e.g. wheat chromosomes.

The plant restoration donor chromosomal component may be from any wild or cultivated plant including but not limited to maize, rice, sorghum, rye, barley, wheat, millet, oats, sugarcane, turfgrass, triticale, switchgrass, wheatgrass, *Thinopyrum, Aegilops, Secale, Haynaldia, Elyymus, Hordeum*, soybean, canola, alfalfa, sunflower, cotton, maize, or a related species thereof. The plant restoration donor chromosomal component may be from any number of plant species, including but not limited to *Thinopyrum, Aegilops, Secale, Haynaldia, Elyymus,* or *Hordeum* species. In some embodiments, the plant restoration donor chromosomal component may be from a wheat line having one or more chromosomes from maize, rice, sorghum, rye, barley, wheat, millet, oats, sugarcane, turfgrass, triticale, switchgrass, wheatgrass, *Thinopyrum, Aegilops, Secale, Haynaldia, Elyymus,* or *Hordeum*, soybean, canola, alfalfa, sunflower, cotton, maize, or a related species thereof. The plant restoration donor chromosomal component may be introduced and/or from a telosomic addition line, such as a monotelosomic or ditelosomic addition line, or a disomic addition line. In some examples, the plant having the plant restoration donor chromosomal component is a from a wheat line, including but not limited to a Blue Sando, Blue Baart, Blue Onas, Blue 1, PBB, or Blue Norco wheat line. Non-limiting examples include but are not limited to the wheat variety Blue Baart, which has a disomic addition of *Thinopyron ponticum* chromosome 4E, Blue Norco, which has ditelosomic addition of *Thinopyron ponticum* chromosome 4E, or a wheat line which has a disomic addition of *Hordeum vulgare* (barley) chromosome 4H. Blue Norco, aneuploid, monosomic, disomic lines, and other wheat lines are publicly available and may be obtained from a number of centers, such as the National Small Grains Collection (United States Department of Agriculture—Agricultural Research Service, National Small Grains Collection, Aberdeen, Id. 83210 USA), or Wheat Genetics Resource Center (Kansas State University, Kansas, USA).

In some embodiments, the plant restoration donor chromosomal component is from two, three, or more of the same or different species to make a hybrid (chimeric) plant restoration donor chromosomal component. In some embodiments, the hybrid (chimeric) plant restoration donor chromosomal component has the plant-derived polynucleotide that confers the plant phenotypic marker from one plant or species and the male-fertility restoration locus from a different plant or species. The plant-derived polynucleotide that confers the plant phenotypic marker in the hybrid (chimeric) plant restoration donor chromosomal component may have one or more chromosomes or chromosomal fragments from maize, rice, sorghum, rye, barley, wheat, millet, oats, sugarcane, turfgrass, triticale, switchgrass, wheatgrass, *Thinopyrum, Aegilops, Secale, Haynaldia, Elyymus, Hordeum*, soybean, canola, alfalfa, sunflower, cotton, maize, or a related species thereof. The male-fertility restoration locus in the hybrid (chimeric) plant restoration donor chromosomal component may have one or more chromosomes or chromosomal fragments from maize, rice, sorghum, rye, barley, wheat, millet, oats, sugarcane, turfgrass, triticale, switchgrass, wheatgrass, *Thinopyrum, Aegilops, Secale, Haynaldia, Elyymus, Hordeum*, soybean, canola, alfalfa, sunflower, cotton, maize, or a related species thereof. In one example, the plant phenotypic marker is from *Thinopyrum ponticum*, for example, chromosome 4E, and the fertility restoration locus from *Hordeum vulgare* (barley), for example, chromosome 4H, to make a hybrid (chimeric) plant restoration donor chromosomal component of 4H-4E. In some embodiments, the hybrid (chimeric) plant restoration donor chromosomal component includes the short arm of chromosome 4 from *Hordeum vulgare* (barley) and the long arm of chromosome 4E from *Thinopyron ponticum*, for example, from Blue Norco to make a hybrid (chimeric) plant restoration donor chromosomal component of 4HS-4EL. The plant phenotypic marker and fertility restoration locus may be from any suitable lines, including but not limited to disomic additions, such as barley 4H, *Thinopyrum ponticum* chromosome 4E, *Agropyron* 4E, or combinations thereof.

Confirmation may be made that the plant, plant part, plant cell, or seed contains the plant restoration donor chromosomal component, including o the phenotypic marker or male-fertility restoration locus or both using routine and well-known methods. Plant restoration donor chromosomal components should retain male-fertility restoration activity in plants, particularly the ability to promote male tissue development. The plant's male-fertility condition can be assessed by any suitable technique, for example, by observation of the plant's male tissue development, such as phenotyping of anthers and seed set on individual plants. See, for example, Example 1 herein.

Absence of the plant restoration donor chromosomal component, for example, lost by crossing or mutation, may be evidenced by plants lacking the male-fertility phenotype or by plants, plant parts, plant cells, or seeds lacking the phenotype conferred by the plant-derived phenotypic marker as compared to a control. Alternatively, or additionally, confirmation of the presence or absence of the plant restoration donor chromosomal component may occur later, for example, after multiple plant crossings or from subsequent generations.

Figure 2:
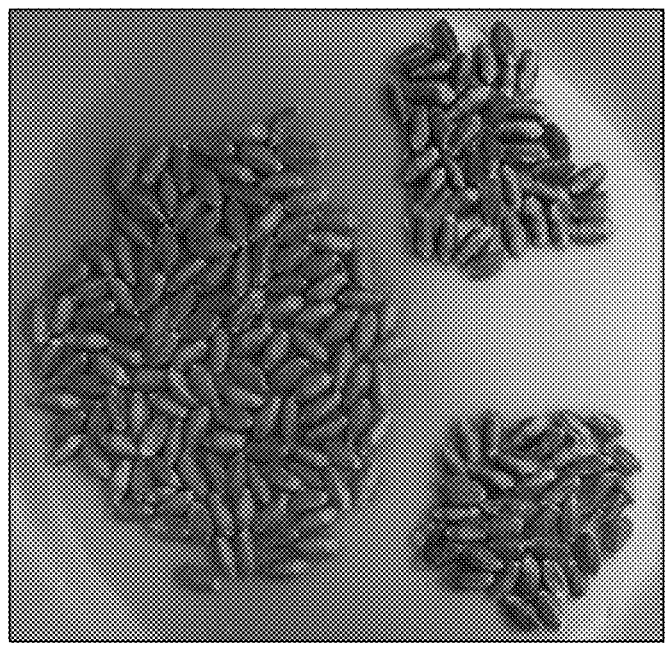
FIG. 2. shows an example of seed from a wheat F3 plant segregating for seed color with a portion of white-colored wheat seeds that will give rise to male-sterile female wheat plants, a portion of light blue-colored wheat seeds (heterozygous for blue aleurone) that will give rise to male-fertile wheat plants; and a portion of dark blue-colored wheat seeds (homozygous for blue aleurone) that will give rise to male-fertile wheat plants.

Seeds produced from the plants or crosses may be harvested together and sorted into separate populations if desired. For example, seeds comprising the plant-derived plant phenotypic seed marker linked to the fertility restoration locus are seeds that may be sorted and separated for use as a maintainer and the seeds lacking the plant-derived plant phenotypic marker linked to the fertility restoration locus (plant restoration donor chromosomal component) may be grown and used as male-sterile female parents in hybrid crosses. The seeds may be manually, mechanically, or optically sorted into these populations. To facilitate high throughput and analysis, the sorting may employ a semi-automated or automated approach. Populations of seeds may be sorted using optical sensing technology including multi or hyper spectral imaging, uv, visible or NIR spectroscopy systems, and/or optical scanning. For example, when the plant phenotypic marker from the plant restoration donor chromosomal component is a color marker such as aleurone, the homozygous blue seed will be more intensely colored than heterozygous blue seed and may sorted on that basis, e.g. the seeds having different concentrations or expression levels of the blue aleurone. See, for example, FIG. 2.

Additionally or alternatively, seeds may be evaluated for the presence of the plant restoration donor chromosomal component, for example, the plant phenotypic marker, using any other suitable technique, including but not limited to flow cytometry or qPCR.

Alternately, the seed may be mixed (unsorted) so that a first portion of seeds contain the one or more homozygous mutations of the male-fertility polynucleotide (seeds that will give rise to male-sterile female plants) and a second portion of seeds contain the one or more homozygous mutations of the male-fertility polynucleotide and the plant restoration donor chromosomal component comprising a plant-derived polynucleotide that confers the plant phenotypic marker linked to the male-fertility restoration locus (seeds that will give rise to male-fertile plants). A plant phenotypic marker that is a seed color marker may be used to sort and separate hybrid wheat or inbred wheat seeds from maintainer wheat seeds. In some examples, the mixture of seeds are planted together to increase the number of male-sterile female seeds produced. The mixture of seeds may be placed in a bag or other appropriate container. The method may include planting the mixture of seeds of male and female parent plants in the same row in a field, rather than in separate rows. The male and female parent plants are grown and the male parent plants fertilize the female parent plants to produce seed. The resulting seed will be a mixture of seeds that, when planted, will give rise to male-sterile or male-fertile plants. The In some examples, the percentage of seeds produced that will give rise to male-fertile plants may be at least about 20%, 25%, 30%, 35%, 40% or 45% of the seeds produced. In some examples, the percentage of seeds produced that will give rise to male-sterile female plants is at least about 55%, 60%, 65%, 70%, 75%, 80%, 85% or 90% of the seeds produced. In some aspects, this method increases the number of seeds produced that will give rise to male-sterile female plants as compared the number of male-sterile female seeds produced in a field where the female-sterile seeds and male-sterile seeds are not planted together in the some row, but are each planted in separate rows of male and female rows.

Also provided herein is a plant cell, plant, or seed obtained or produced from the methods described herein. In some methods, a male-sterile female plant is fertilized with pollen from a plant comprising the plant restoration donor chromosomal component that complements the female plant's male-sterile condition. This method produces seed that may be a mixture of seed that, when planted, gives rise to male-sterile or male-fertile plants. The absence of the plant phenotypic marker in the seeds indicates that the seed lacks the plant restoration donor chromosomal component and, when planted, will give rise to male-sterile female plants. Plants from these seeds may be used as male-sterile female inbreds for hybrid seed production. The presence of the plant phenotypic marker in the seed indicates that the seed contains the plant restoration donor chromosomal component and will give rise to male-fertile plants. Plants grown from this seed may be used as a maintainer if desired. The seed may be unsorted, mixed with other seed, or sorted and separated into populations using routine techniques and instruments as described elsewhere herein and known to one in the art.

Since a male sterile plant, e.g a male sterile wheat plant, cannot be maintained by itself, provided herein are compositions and methods for maintaining the homozygous recessive male sterility condition of the wheat plant that include the use of a plant restoration donor chromosomal component for restoration of male fertility to the wheat plant. For example, a mutation in a gene critical to male fertility can impart a male sterility phenotype to wheat plants when this mutant allele is in the homozygous state, for example, in endogenous wheat Ms1, Ms5, Ms9, Ms22, Ms26, and Ms45 polynucleotides encoding wheat Ms1, Ms5, Ms9, Ms22, Ms26, and Ms45 polypeptides respectively. Since Ms1 in wheat behaves as a single gene recessive, in some embodiments only the ms/male-fertility polynucleotide or allele located on chromosome 4BS may need to be mutated to confer male-sterility to a wheat plant.

When a male-fertility restoration locus that is capable of functionally complementing homozygous recessive alleles that confer male sterility is introduced into and expressed in the male-sterile plant, male-fertility is restored to the plant so that it can produce viable pollen and is capable of fertilizing a cross-compatible female plant.

Maintenance of the homozygous recessive condition or male-sterility condition may include introducing into the wheat plant a plant restoration donor chromosomal component to create a maintainer plant. The plant restoration donor chromosomal component, upon introduction into a plant that has one or more homozygous mutations of a male-fertility polynucleotide, restores the male-fertility to the plant so that the plant produces viable pollen capable of fertilizing itself or a cross-compatible plant. In some embodiments, the plant restoration donor chromosomal component may be present in the maintainer wheat plant as an additional chromosome in the wheat genome, as a translocated chromosome in the wheat genome, or as a substitution chromosome for a wheat chromosome in the wheat genome. Accordingly, provided herein is a wheat plant or cell that has one or more of its wheat chromosomes substituted by a plant restoration donor chromosomal component from a non-wheat plant or species. For example, in some embodiments, the wheat plant or cell has a homoeologous chromosome pair of two chromosomes. The first chromosome is native to the wheat plant and the second chromosome comprises a plant restoration donor chromosomal component. The plant restoration donor chromosomal component may be translocated with or substituted for any wheat chromosomes so long as it does not have a deleterious effect on the wheat plant. In some embodiments, the addition, translocation, or substitution should not interfere with the one or more wheat plant's homozygous mutations that confer the male-sterile phenotype. In some embodiments, the plant restoration donor chromosomal component may be substituted for or translocated into a 5AL wheat chromosome.

Wheat seeds from these plants having chromosomal substitutions are euploid but have one or more of chromosomes substituted by or contain the plant restoration donor chromosomal component. Confirmation of the number of chromosomes in the wheat plant or cell or the plant restoration donor chromosomal component's translocation or substitution may be detected using any appropriate technique, such as genomic in situ hybridization (GISH) or fluorescent in situ hybridization (FISH).

The male-sterility condition of the wheat plant may be maintained by self-fertilizing the maintainer plant comprising the plant restoration donor chromosomal component which will result in the creation of a mixed seed population. A portion of the seed will contain the one or more homozygous male-sterility mutations and a portion of the seed will contain the one or more homozygous male-sterility mutations and the plant restoration donor chromosomal component. The seed resulting from self-fertilization of the maintainer can be planted and the seed from these plants selected and sorted for use in male-sterility maintenance or hybrid seed production. In some examples, the selection process utilizes any suitable seed marker as a plant phenotypic marker to identify such seed. Accordingly, provided herein are methods for producing seed from a wheat plant by self-fertilizing the maintainer plant. In other embodiments, a male-sterile wheat plant homozygous for one or more mutations of a male-fertility polynucleotide may be fertilized by pollen from a male-fertile plant that it is cross-compatible with. In some aspects, the male-fertile plant contains a plant restoration donor chromosomal component.

Also included herein are methods and compositions for restoring male fertility to a plant having one or more homozygous recessive mutations in a male fertility polynucleotide that confers male sterility to the plant. In some aspects, the method includes introducing the plant restoration donor chromosomal component that functionally complements the male-sterility phenotype from the one or more homozygous mutations in the male-sterile wheat plant so that the wheat plant becomes male-fertile. The plant restoration donor chromosomal component may be introduced using any number of approaches as described herein and known to one skilled in the art.

The plants or plant restoration chromosomal component for use in the methods and compositions described herein may be a monocot or a dicot. Monocots include but are not limited to maize, rice, sorghum, rye, barley, wheat, millet, oats, triticale, fonio, sugarcane, turfgrass, switchgrass, *Thinopyrum, Aegilops, Secale, Haynaldia, Elyymus*, or *Hordeum*, or a related species thereof. Dicots include but not limited to soybean, canola, alfalfa, sunflower, cotton, tobacco, peanut, potato, tobacco, *Arabidopsis*, or safflower, or a related species thereof.

Additional Definitions

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

"Expression" generally refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Gamete" refers to a reproductive cell having the 1 n set (haploid number) of chromosomes that can fuse with another gamete of the opposite sex during fertilization in organisms undergoing sexual reproduction. As used herein, a gamete in organisms undergoing asexual reproduction refers to a cell having a 2n number (an unreduced number) of chromosomes.

The term "genome" refers to the entire complement of genetic material (genes and non-coding sequences) that is present in each cell of an organism, or virus or organelle; and/or a complete set of chromosomes inherited as a (haploid) unit from one parent.

As used herein, a "male sterile plant" is a plant that does not produce male gametes that are viable or otherwise capable of fertilization and is female fertile.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollen, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant.

"Polynucleotide", "nucleic acid sequence", "nucleotide sequence", or "nucleic acid fragment" are used interchangeably and is a polymer of RNA or DNA that is single- or double-stranded, optionally containing synthetic, non-natural or altered nucleotide bases.

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

"Polypeptide", "peptide", "amino acid sequence" and "protein" are used interchangeably herein to refer to a polymer of amino acid residues.

"Progeny" comprises any subsequent generation of a plant.

"Promoter functional in a plant" is a promoter capable of controlling transcription in plant cells whether or not its origin is from a plant cell.

As used herein "promoter" includes reference to a region of DNA upstream from the start of transcription and involved in recognition and binding of RNA polymerase and other proteins to initiate transcription.

A "plant promoter" is a promoter capable of initiating transcription in plant cells.

The terms "suppress", "suppressed", "suppression", "suppressing" and "silencing", are used interchangeably herein and include lowering, reducing, declining, decreasing, inhibiting, eliminating or preventing. "Silencing" or "gene silencing" does not specify mechanism and is inclusive, and not limited to, antisense, cosuppression, viral-suppression, hairpin suppression, stem-loop suppression, RNAi-based approaches, and small RNA-based approaches and the like.

As used herein, the term "wheat" refers to any species of the genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. mocha, T. compactum, T. sphaerococcum, T. vavilovii*, and interspecies cross thereof. Tetraploid wheat includes *T. durum* (also referred to as durum wheat or *Triticum turgidum* ssp. durum), *T. dicoccoides, T. dicoccum, T. polonicum*, and interspecies cross thereof. In addition, the term "wheat" includes possible progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. A wheat cultivar for use in the present disclosure may belong to, but is not limited to, any of the above-listed species. Also encompassed are plants that are produced by conventional techniques using *Triticum* sp. as a parent in a sexual cross with a non-*Triticum* species, such as rye (*Secale cereale*), including but not limited to Triticale. In some aspects, the wheat plant is suitable for commercial production of grain, such as commercial varieties of hexaploid wheat or durum wheat, having suitable agronomic characteristics which are known to those skilled in the art.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1: A Mono-Telosomic Chromosome from *Thinopyrum ponticum* can Complement Ms45 Triple Mutations and Restore Fertility As demonstrated herein, the 4EL chromosome from Blue Norco is able complement Tams45-abd mutations. Blue Norco, a blue aleurone wheat, is a ditelosomic addition line which has an extra set of 4EL (2n=42"+2t) that is available from USDA-ARS (PI 54241965). Tams45-abd plants were crossed to Blue Norco as a male parent. The crossed seeds (blue in color) were planted, and F1 progeny screened to confirm the presence TaMS45-A, -B and -D mutations and allowed to self-pollinate.

Light blue F2 seed (monosomic for 4EL, i.e. one copy of 4EL) were planted and progeny were genotyped for TaMs45 mutant alleles and allowed to self-pollinate and set seed. Of the harvested seeds from these plants, 64 light blue seeds (with 4EL) and white seeds (without 4EL) each were planted to obtain F3 plants which were genotyped for TaMs45 mutant alleles. Triple homozygous (Tams45-abd) mutant plants from both white and blue kernels were identified and analyzed for male fertility through phenotyping of anthers and seed set on individual plants. In total, 12 triple homozygous Tams45-abd plants were analyzed, six from white seeds and six from blue seeds (Table 2). The anthers of the Tams45-abd plants from white seeds were shriveled in shape and smaller in size, whereas the anthers of Tams45-abd plants from blue kernels were similar to wild-type plants (FIG. 1). All six Tams45-abd plants that carried 4EL chromosome were male-fertile with seed set comparable to wild-type plants while the six plants without the 4EL chromosome showed negligible seed-set (Table 2; Note: seed observed in these plants was likely to due to open fertilization as these heads were not bagged and these plants were in very close proximity with fertile flowering plants).

To test a working male-sterile maintainer system based on blue white selection, seeds from fertile F3 plants were harvested and 12 visually sorted white and light blue seeds from three F3 plants (total=36 white and blue seeds each) were planted to obtain F4 generation. All the 36 plants from the white seeds were male-sterile while all the 36 plants from blue seeds were male-fertile (Table 2). This data demonstrates that a monosomic 4EL chromosome can complement and restore male-fertility and maintain the triple homozygous Tams45 mutants. Further it is possible to identify from the seeds of a maintainer plant, based on the color, the seed which will produce a male-sterile or a male-fertile plant.

TABLE 2

Complementation of TaMs45 triple homozygous mutants with 4EL chromosome.

| Genotype of TaMs45 homeologs[1] | Plants | Seed Set-Fertility | | Male fertile plants | Male sterile plants |
| --- | --- | --- | --- | --- | --- |
| | | Total Seed | Seed per Plant | | |
| F3 generation | | | | | |
| Tams45-abd + 4EL | 6 | 1635 | 272 | 6 | 0 |
| Tams45-abd | 6 | 68* | 11 | 0 | 6 |
| F4 generation | | | | | |
| Tams45-abd + 4EL | 36 | 4858 | 135 | 36 | 0 |
| Tams45-abd | 36 | 0 | 0 | 0 | 36 |
| TaMs45-ABD | 5 | 855 | 171 | 5 | 0 |

*Note:
heads were not bagged and grew in close proximity of same stage fertile plants Example 2: Production of a 4HS-4EL Hybrid Chromosome In this example, a 4HS-4EL hybrid chromosome is created using a Robertsonian translocation. For example, aneuploid stocks may be used to create Robertsonian translocations in a directed manner by making the appropriate plant restoration donor chromosomal component in monosomic condition. A Chinese Spring wheat line which has a disomic addition (2n=44) of chromosome 4H from Betzes barley was used in this example. (Wheat stock TA #3700, which has a disomic addition (2n=44) of *Hordeum vulgare* (barley) chromosome 4H, was obtained from the Wheat Genetics Resource Center at Kansas State University, USA.) The wheat variety Blue Baart, which has a disomic addition (2n=44) of *Thinopyrum ponticum* chromosome 4E and has blue aleurone was used in this example. (Burešová V, Kopecý D, Bartoš J, Martinek P, Watanabe N, Vyhnánek T and Doležal J. 2015. Variation in genome composition of blue-aleurone wheat. Theor. Appl. Genet. 128:273-282) A cross was made between these two lines, and the resulting $F_1$ seeds were grown and the plants allowed to self-pollinate. The presence of a new 4HS-4EL chromosome in the $F_2$ or $F_3$ generations may be screened using any suitable method, for example, for the presence of blue color, indicative of the presence of 4EL, the absence of markers for 4ES, the presence of a 4HS marker such as Mmag 053, and the absence of a 4HL marker such as HVM40 (Molnár I, Linc G, Dulai S, Nagy ED and Molnár-Láng MM. 2007. Ability of chromosome 4H to compensate for 4D in response to drought stress in a newly developed and identified wheat-barley 4H(4D) disomic substitution line. Plant Breeding 126: 369-374). Candidate lines may be further screened, for example, by using standard cytogenetic techniques such as GISH (genomic in situ hybridization) to confirm the presence of a hybrid 4HS-4EL chromosome.

Example 3: Using a CRISPR-Cas9-Induced Pericentric Inversion to Place Ms1 and Ba1 on the Same Chromosome Arm In this example, pericentric inversions are used in wheat to place the Ms1 and Ba1 genes on the same chromosome arm in those instances where the Ms1 complement (homeologue) and the Ba1 gene are on different chromosome arms, for example, located on 4ES or 4HS and 4EL, respectively. One advantage of this approach is that it would place the Ms/and Ba1 trait genes on the same chromosome arm and avoid their separation due to a breakage of the chromosome at the centromere and possible misclassification of seeds as male-sterile when in fact they are male-fertile.

In this example, the starting material may use the 4HS-4EL chromosome described in Example 2 herein. Two DSBs will be induced: one between the Ms1-H gene and the telomere of 4HS, and one between the Ba1 gene and the centromere of 4HS-4EL. The barley Ms1-H gene is oriented with the 5' end closest to the telomere and the 3' end closest to the centromere. The DNA sequence 5' of the Ms1-H gene (http://plants.ensembl.org/Hordeum_valgare/Tools/Blast) will be analyzed for the NGG sequence of the Protospacer Adjacent Motif (PAM) for cas9. For each site found, the 17 bp upstream sequence will be evaluated to find a unique cutting site which is not present in the wheat genome.

Marker fragments located on the long arm of chromosome 4J (4Eb) and located between the centromere and the BaThb gene will be cloned and sequenced; the resulting sequences will be analyzed for the NGG sequence of the Protospacer Adjacent Motif (PAM) for cas9. For each site, the 17 bp upstream sequence will be evaluated to find a unique cutting site which is not present in the wheat genome.

When suitable site(s) and guide RNAs for the two locations have been identified, the two DSBs will be induced by CRISPR-cas9 using standard methods. At a certain frequency, the chromosome fragment containing the centromere and Ms1-H will be rejoined to the telomeric ends in the opposite orientation, resulting in a pericentric inversion, with Ms1-H and Ba1 now located on the same arm of the new chromosome. PCR primers will be designed that produce a PCR product only when the pericentric inversion has occurred.

Example 4: Alternative Construction for a 4E-Ms45 System

This example describes one embodiment of constructing a hybridization system using 4E-ms45. Rather than the seed color marker (blue aleurone=BA) and functional dominant Ms45 allele being provided by an addition telocentric chromosome such as 4EL, the 4EL chromosome arm will be translocated into the wheat genome, substituting for an existing wheat chromosome arm.

The proper choice of wheat chromosome arm targeted for substitution by 4EL may confer some advantages over an independent (addition) 4EL. One possible advantage is the reduced gametic transmission of the addition telosomic chromosome, for example, a reduced male and/or female transmission rate. This will allow for an increased percentage of non-blue seed to be produced during female seed increase (self-pollination). In this example, 4EL will be substituted for wheat chromosome arm 5AL. Gametes containing a 5AS-4EL chromosome will lack a copy of 5AL. See, for example, FIG. 4.

Even in the case of reduced male and/or female transmission rates, some homozygous 4EL (blue) seed may be produced. The presence of these homozygous blue seeds may be identified and detected using seed sorting. For example, the homozygous blue seed will be more intensely colored than heterozygous blue seed and may be sorted on that basis. It is believed that a 5AS-4EL homozygous plant will likely be male-sterile, so little or no seed sorting would be needed to remove such seeds from the population of blue seeds.

A 5AS-4EL chromosome may be created using a Robertsonian translocation. In this example, aneuploid stocks may be used to create wheat-plant restoration donor chromosomal component Robertsonian translocations in a directed manner by making the appropriate wheat and plant restoration donor chromosomal components in monosomic condition. A Chinese Spring aneuploid wheat line which segregates for monosomy of wheat chromosome 5A was used in this example. (Stock TA #3045, which segregates for monosomy of wheat chromosome 5A, was obtained from the Wheat Genetics Resource Center at Kansas State University, USA.) The wheat variety Blue Baart, which has a disomic addition (2n=44) of *Thinopyron ponticum* chromosome 4E and has blue aleurone was used in this example (Burešová V, Kopecý D, Bartoš J, Martinek P, Watanabe N, Vyhnánek T and Doležal J. 2015. Variation in genome composition of blue-aleurone wheat. Theor. Appl. Genet. 128:273-282). 10 seeds of the Chinese Spring aneuploid wheat line which segregates for monosomy of wheat chromosome 5A were grown, root tips sampled and chromosome counts were done by standard methods to identify monosomic (2n-1=41) plants. Monosomic plants produce ~75% nullisomic (n-1=20) female gametes. The identified monosomic plants were crossed as females with Blue Baart. $F_1$ seeds produced from nullisomic gametes will have the composition of 42 chromosomes, including 1 5A+1 4E, both derived from the male parent Blue Baart and have blue aleurone color. $F_1$ seeds were grown and the plants allowed to self-pollinate.

The presence of a new 5AS-4EL chromosome may be screened by any suitable method, for example, by the presence of blue aleurone seed color, indicative of the presence of 4EL, and the absence of markers for 4ES. This would be indicative of breakage of the 4E chromosome. Candidate lines may be further screened, for example, by using standard cytogenetic techniques such as FISH (fluorescence in situ hybridization) to confirm the presence of a hybrid 5AS/4EL chromosome.

Once established, such lines will be self-pollinated to confirm male-sterility of 5AS/4EL homozygotes as well as reciprocally crossed as male and female to determine pollen and egg transmission frequencies. The 5AS/4E chromosome may be introgressed along with recessive ms45 alleles on 4A, 4B and 4D into various elite female lines to facilitate hybrid seed production.

Example 5: Use of 4E or 4H Addition Chromosomes to Complement Wheat Ms9 Triple Mutations and to Restore Fertility In this example, a wheat CAS9-CRISPR construct has been made targeting the TA-Ms9 gene using a guide, TA-Ms9-CR2 ggaggtacaccaactacctg (SEQ ID NO:40).

Wheat plants will be transformed with this construct and the endogenous wheat Ms9 genes will be assessed for mutations in all three wheat genomes. Crosses and subsequent self-pollinations will be made to combine the Ms9 mutations as homozygous into a single plant. Wheat plants homozygous for Ms9 mutations in all three genomes will be evaluated for male sterility through examination of anthers and seed set on individual plants.

If male sterility is achieved, these wheat plants may be maintained by crossing them with a wheat maintainer line containing a 4EL addition chromosome such as Blue Norco, described in Example 1. The TA-Ms9 gene maps to the long arm of chromosome 4 in wheat which has synteny with the long arm of the 4EL addition chromosome, which should provide a complement function to the TA-ms9 mutation, restoring male fertility. A wheat line containing the barley chromosome 4 as an addition chromosome (*Hordeum vulgare* 4H) may also be evaluated for possible Ta-ms9 restoration. Restoration of male fertility to these male-sterile wheat plants by the 4E, 4EL or 4H addition chromosomes in the wheat maintainer line will be evaluated by the ability to complement the ms9 mutations in these plants, as determined by anther examination and seed set on individual plants.

As described in Example 1, the 4EL addition chromosome also contains the blue aleurone gene (BA) on the long arm, which gives a dominant blue seed phenotype. Therefore, seed from self-pollinated homozygous TA-ms9 mutant and restored with the presence of the 4EL addition chromosome, will segregate for blue and non-blue seed. These resultant seeds can be grown and evaluated for male fertility and sterility. As demonstrated in Example 1, the expectation is that non-blue seed derived plants will be male-sterile and blue seed derived plants will be male fertile, and the latter can act as a maintainer line for the TA-ms9 mutation in a hybrid system.

That which is claimed:

1. A method of restoring male fertility in a Ms45 male-sterile wheat plant, the method comprising:
    (a) introducing into the Ms45 male-sterile wheat plant, wherein the Ms45 male-sterile wheat plant comprises triple homozygous mutations of a Ms45 male-fertility polynucleotide that cause a male sterility phenotype, a plant restoration donor chromosomal component comprising a 4E chromosomal component from *Thinopyrum* or *Agropyron*, the 4E chromosomal component comprising:
        a plant polynucleotide that confers a plant seed phenotype linked to a Ms45 male-fertility restoration locus; and
    (b) restoring male-fertility to the Ms45 male-sterile wheat plant by the 4E chromosomal component, wherein expression of the 4E donor chromosomal component functionally complements the male-sterility phenotype from the triple homozygous Ms45 mutations in the Ms45 male-sterile wheat plant so that the Ms45 male-sterile wheat plant becomes male-fertile.

2. The method of claim 1, wherein expression of the Ms45male-fertility restoration locus functionally complements the male-sterility phenotype from the triple homozygous Ms45 mutations in the male-sterile wheat plant.

3. The method of claim 1, wherein the plant polynucleotide that confers the plant phenotype is located on the same chromosomal arm of the 4E chromosomal component as the Ms45 male-fertility restoration locus and not separated by a centromere.

4. The method of claim 1, comprising introducing the 4E chromosomal component by crossing the Ms45 male-sterile wheat plant with a male-fertile plant comprising the 4E chromosomal component.

5. The method of claim 4, wherein the 4E chromosomal component restores fertility to the plant without recombining with the wheat chromosomes.

6. The method of claim 4, wherein the male-fertile plant is a wheat, barley, oat, wheatgrass, or rye plant or a related species thereof.

7. The method of claim 1, wherein the male-fertile plant is Sebesta Blue, Blue Sando, Blue Baart, Blue Onas, Blue 1, PBB, or Blue Norco, and wherein the donor chromosomal component is derived from a non-wheat plant species.

8. The method of claim 1, wherein the plant seed phenotype is a phenotype for color, physiology, or morphology of the seed.

9. The method of claim 8, wherein the color is blue aleurone, P gene, anthocyanin, or Kala 4.

* * * * *